US012527877B2

(12) United States Patent
Glebocka et al.

(10) Patent No.: US 12,527,877 B2
(45) Date of Patent: Jan. 20, 2026

(54) ANTI-TRANSFERRIN RECEPTOR ANTIBODIES, CONJUGATES THEREOF, AND USES THEREOF

(71) Applicant: Arrowhead Pharmaceuticals, Inc., Pasadena, CA (US)

(72) Inventors: Agnieszka Glebocka, Madison, WI (US); Zhao Xu, San Diego, CA (US); Jeffrey Carlson, Madison, WI (US); Jingdong Ye, Lincolnshire, IL (US); Matthew Fowler-Watters, Madison, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 19/035,354

(22) Filed: Jan. 23, 2025

(65) Prior Publication Data

US 2025/0235549 A1 Jul. 24, 2025

Related U.S. Application Data

(60) Provisional application No. 63/718,062, filed on Nov. 8, 2024, provisional application No. 63/662,243, filed on Jun. 20, 2024, provisional application No. 63/573,151, filed on Apr. 2, 2024, provisional application No. 63/624,417, filed on Jan. 24, 2024.

(51) Int. Cl.
*A61K 47/68* (2017.01)
*C07K 16/28* (2006.01)

(52) U.S. Cl.
CPC ...... *A61K 47/6807* (2017.08); *A61K 47/6849* (2017.08); *C07K 16/2881* (2013.01); *C07K 2317/24* (2013.01); *C07K 2317/55* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 4,704,692 | A | 11/1987 | Ladner |
| 4,946,778 | A | 8/1990 | Ladner et al. |
| 5,565,332 | A | 10/1996 | Hoogenboom et al. |
| 5,580,717 | A | 12/1996 | Dower et al. |
| 5,733,743 | A | 3/1998 | Johnson et al. |
| 6,265,150 | B1 | 7/2001 | Terstappen et al. |
| 6,372,250 | B1 | 4/2002 | Pardridge |
| 6,632,671 | B2 | 10/2003 | Unger |

FOREIGN PATENT DOCUMENTS

| | | | |
|---|---|---|---|
| WO | 1987004462 | A1 | 7/1987 |
| WO | 1999058572 | A1 | 11/1999 |
| WO | 2014189973 | A2 | 11/2014 |
| WO | 2016081640 | A1 | 5/2016 |
| WO | 2016081643 | A1 | 5/2016 |
| WO | 2017214112 | A1 | 12/2017 |
| WO | 2018027106 | A2 | 2/2018 |
| WO | 2020028831 | A1 | 2/2020 |
| WO | 2020028836 | A1 | 2/2020 |
| WO | 2020028840 | A1 | 2/2020 |
| WO | 2020028841 | A1 | 2/2020 |
| WO | 2020028842 | A1 | 2/2020 |
| WO | 2020028844 | A1 | 2/2020 |
| WO | 2020028857 | A1 | 2/2020 |
| WO | 2020028861 | A1 | 2/2020 |
| WO | 2020132584 | A1 | 6/2020 |
| WO | 2021142227 | A1 | 7/2021 |
| WO | 2021142260 | A1 | 7/2021 |
| WO | 2021142275 | A1 | 7/2021 |
| WO | 2021142313 | A1 | 7/2021 |
| WO | 2021142331 | A1 | 7/2021 |
| WO | 2021195469 | A1 | 9/2021 |
| WO | 2022020108 | A1 | 1/2022 |
| WO | 2022051665 | A1 | 3/2022 |
| WO | 2022258841 | A1 | 12/2022 |
| WO | 2023283613 | A1 | 1/2023 |
| WO | 2023043953 | A1 | 3/2023 |
| WO | 2023087017 | A1 | 5/2023 |
| WO | 2023196400 | A2 | 10/2023 |
| WO | 2024006976 | A2 | 1/2024 |

OTHER PUBLICATIONS

Al-Lazikani B, Lesk AM, Chothia C. Standard conformations for the canonical structures of immunoglobulins. J Mol Biol. Nov. 7, 1997;273(4):927-48. doi: 10.1006/jmbi.1997.1354. PMID: 9367782.

Almagro JC. Identification of differences in the specificity-determining residues of antibodies that recognize antigens of different size: implications for the rational design of antibody repertoires. J Mol Recognit. Mar.-Apr. 2004;17(2):132-43. doi: 10.1002/jmr.659. PMID: 15027033.

Altenhofer EF, Lawler MJ, Kumar P, Joyce LA, Fowler-Watters M, Pei T, Li Z. Synthesis of a novel cyclopropyl phosphonate nucleotide as a phosphate mimic. Chem Commun (Camb). Jul. 14, 2021;57(55):6808-6811. doi: 10.1039/d1cc02328d. Epub Jun. 18, 2021. PMID: 34142689.

Altschul SF, Gish W, Miller W, Myers EW, Lipman DJ. Basic local alignment search tool. J Mol Biol. Oct. 5, 1990;215 (3):403-10. doi: 10.1016/S0022-2836(05)80360-2. PMID: 2231712.

Altschul SF, Madden TL, Schäffer AA, Zhang J, Zhang Z, Miller W, Lipman DJ. Gapped BLAST and PSI-BLAST: a new generation of protein database search programs. Nucleic Acids Res. Sep. 1, 1997;25(17):3389-402. doi: 10.1093/nar/25.17.3389. PMID: 9254694; PMCID: PMC146917.

Alvarez-Erviti L, Seow Y, Yin H, Betts C, Lakhal S, Wood MJ. Delivery of siRNA to the mouse brain by systemic injection of targeted exosomes. Nat Biotechnol. Apr. 2011;29(4):341-5. doi: 10.1038/nbt.1807. Epub Mar. 20, 2011. PMID: 21423189.

(Continued)

*Primary Examiner* — Peter J Reddig
*Assistant Examiner* — Estella M. Gustilo
(74) *Attorney, Agent, or Firm* — Paul VanderVelde; Meibo Chen; Mitchell Porter

(57) ABSTRACT

The invention provides a transferrin receptor (TfR1) antibody for conjugation to therapeutic payloads. The TfR1 antibodies may be used for delivering the therapeutic payloads, for instance oligonucleotide-based agents, to CNS tissues, skeletal muscle tissues, or heart tissues in vivo.

18 Claims, 5 Drawing Sheets

Specification includes a Sequence Listing.

(56) References Cited

OTHER PUBLICATIONS

Baca M, Presta LG, O'Connor SJ, Wells JA. Antibody humanization using monovalent phage display. J Biol Chem. Apr. 18, 1997;272(16):10678-84. doi: 10.1074/jbc.272.16.10678. PMID: 9099717.
Bird RE, Hardman KD, Jacobson JW, Johnson S, Kaufman BM, Lee SM, Lee T, Pope SH, Riordan GS, Whitlow M. Single-chain antigen-binding proteins. Science. Oct. 21, 1988;242(4877):423-6. doi: 10.1126/science.3140379. Erratum in: Science Apr. 28, 1989;244(4903):409. PMID: 3140379.
Brown M, Figge J, Hansen U, Wright C, Jeang KT, Khoury G, Livingston DM, Roberts TM. Iac repressor can regulate expression from a hybrid SV40 early promoter containing a lac operator in animal cells. Cell. Jun. 5, 1987;49(5):603-12. doi: 10.1016/0092-8674(87)90536-8. PMID: 3034429.
Carter P, Presta L, Gorman CM, Ridgway JB, Henner D, Wong WL, Rowland AM, Kotts C, Carver ME, Shepard HM. Humanization of an anti-p185HER2 antibody for human cancer therapy. Proc Natl Acad Sci U S A. May 15, 1992;89 (10):4285-9. doi: 10.1073/pnas.89.10.4285. PMID: 1350088; PMCID: PMC49066.
Chothia C, Lesk AM. Canonical structures for the hypervariable regions of immunoglobulins. J Mol Biol. Aug. 20, 1987;196(4):901-17. doi: 10.1016/0022-2836(87)90412-8. PMID: 3681981.
Chothia C, Lesk AM, Tramontano A, Levitt M, Smith-Gill SJ, Air G, Sheriff S, Padlan EA, Davies D, Tulip WR, et al. Conformations of immunoglobulin hypervariable regions. Nature. Dec. 21-28, 1989;342(6252):877-83. doi: 10.1038/342877a0. PMID: 2687698.
Elbashir SM, Lendeckel W, Tuschl T. RNA interference is mediated by 21- and 22-nucleotide RNAs. Genes Dev. Jan. 15, 2001;15(2):188-200. doi: 10.1101/gad.862301. PMID: 11157775; PMCID: PMC312613.
Fire A, Xu S, Montgomery MK, Kostas SA, Driver SE, Mello CC. Potent and specific genetic interference by double-stranded RNA in Caenorhabditis elegans. Nature. Feb. 19, 1998;391(6669):806-11. doi: 10.1038/35888. PMID: 9486653.
Gossen M, Bujard H. Tight control of gene expression in mammalian cells by tetracycline-responsive promoters. Proc Natl Acad Sci U S A. Jun. 15, 1992;89(12):5547-51. doi: 10.1073/pnas.89.12.5547. PMID: 1319065; PMCID: PMC49329.
Huston JS, Levinson D, Mudgett-Hunter M, Tai MS, Novotný J, Margolies MN, Ridge RJ, Bruccoleri RE, Haber E, Crea R, et al. Protein engineering of antibody binding sites: recovery of specific activity in an anti-digoxin single-chain Fv analogue produced in *Escherichia coli*. Proc Natl Acad Sci U S A. Aug. 1988;85(16):5879-83. doi: 10.1073/pnas.85.16.5879. PMID: 3045807; PMCID: PMC281868.
Karlin S, Altschul SF. Methods for assessing the statistical significance of molecular sequence features by using general scoring schemes. Proc Natl Acad Sci U S A. Mar. 1990;87(6):2264-8. doi: 10.1073/pnas.87.6.2264. PMID: 2315319; PMCID: PMC53667.
Karlin S, Altschul SF. Applications and statistics for multiple high-scoring segments in molecular sequences. Proc Natl Acad Sci U S A. Jun. 15, 1993;90(12):5873-7. doi: 10.1073/pnas.90.12.5873. PMID: 8390686; PMCID: PMC46825.
Kunkel TA. Rapid and efficient site-specific mutagenesis without phenotypic selection. Proc Natl Acad Sci U S A. Jan. 1985;82(2):488-92. doi: 10.1073/pnas.82.2.488. PMID: 3881765; PMCID: PMC397064.
Liu R, Guan JQ, Zak O, Aisen P, Chance MR. Structural reorganization of the transferrin C-lobe and transferrin receptor upon complex formation: the C-lobe binds to the receptor helical domain. Biochemistry. Nov. 4, 2003;42 (43):12447-54. doi: 10.1021/bi0352973. PMID: 14580189.
Morrison SL, Johnson MJ, Herzenberg LA, Oi VT. Chimeric human antibody molecules: mouse antigen-binding domains with human constant region domains. Proc Natl Acad Sci U S A. Nov. 1984;81(21):6851-5. doi: 10.1073/pnas.81.21.6851. PMID: 6436822; PMCID: PMC392030.
Presta LG, Lahr SJ, Shields RL, Porter JP, Gorman CM, Fendly BM, Jardieu PM. Humanization of an antibody directed against IgE. J Immunol. Sep. 1, 1993;151(5):2623-32. PMID: 8360482.
Queen C, Schneider WP, Selick HE, Payne PW, Landolfi NF, Duncan JF, Avdalovic NM, Levitt M, Junghans RP, Waldmann TA. A humanized antibody that binds to the interleukin 2 receptor. Proc Natl Acad Sci U S A. Dec. 1989;86 (24):10029-33. doi: 10.1073/pnas.86.24.10029. PMID: 2513570; PMCID: PMC298637.
Khozeimeh Sarbisheh E, Dewaele-Le Roi G, Shannon WE, Tan S, Xu Y, Zeglis BM, Price EW. DiPODS: A Reagent for Site-Specific Bioconjugation via the Irreversible Rebridging of Disulfide Linkages. Bioconjug Chem. Dec. 16, 2020;31 (12):2789-2806. doi: 10.1021/acs.bioconjchem.0c00590. Epub Nov. 19, 2020. PMID: 33210532; PMCID: PMC7983808.
Shockett P, Difilippantonio M, Hellman N, Schatz Dg. A modified tetracycline-regulated system provides autoregulatory, inducible gene expression in cultured cells and transgenic mice. Proc Natl Acad Sci U S A. Jul. 3, 1995;92(14):6522-6. doi: 10.1073/pnas.92.14.6522. PMID: 7604026; PMCID: PMC41550.
Sidhu SS, Lowman HB, Cunningham BC, Wells JA. Phage display for selection of novel binding peptides. Methods Enzymol. 2000;328:333-63. doi: 10.1016/s0076-6879(00)28406-1. PMID: 11075354.
Teh EM, Hewitt J, Ung KC, Griffiths TA, Nguyen V, Briggs SK, Mason AB, MacGillivray RT. Identification of the epitope of a monoclonal antibody that disrupts binding of human transferrin to the human transferrin receptor. FEBS J. Dec. 2005;272(24):6344-53. doi: 10.1111/j.1742-4658.2005.05028.x. PMID: 16336271.
Ward ES, Güssow D, Griffiths AD, Jones PT, Winter G. Binding activities of a repertoire of single immunoglobulin variable domains secreted from *Escherichia coli*. Nature. Oct. 12, 1989;341(6242):544-6. doi: 10.1038/341544a0. PMID: 2677748.
Winter G, Griffiths AD, Hawkins RE, Hoogenboom HR. Making antibodies by phage display technology. Annu Rev Immunol. 1994;12:433-55. doi: 10.1146/annurev.iy.12.040194.002245. PMID: 8011287.
Yang WP, Green K, Pinz-Sweeney S, Briones AT, Burton DR, Barbas CF 3rd. CDR walking mutagenesis for the affinity maturation of a potent human anti-HIV-1 antibody into the picomolar range. J Mol Biol. Dec. 1, 1995;254 (3):392-403. doi: 10.1006/jmbi.1995.0626. PMID: 7490758.
Yao F, Svensjö T, Winkler T, Lu M, Eriksson C, Eriksson E. Tetracycline repressor, tetR, rather than the tetR-mammalian cell transcription factor fusion derivatives, regulates inducible gene expression in mammalian cells. Hum Gene Ther. Sep. 1, 1998;9(13):1939-50. doi: 10.1089/hum.1998.9.13-1939. PMID: 9741432.
Yao MZ, Gu JF, Wang JH, Sun LY, Liu H, Liu XY. Adenovirus-mediated interleukin-2 gene therapy of nociception. Gene Ther. Aug. 2003;10(16):1392-9. doi: 10.1038/sj.gt.3301992. PMID: 12883536.
Ye JD, Tereshko V, Frederiksen JK, Koide A, Fellouse FA, Sidhu SS, Koide S, Kossiakoff AA, Piccirilli JA. Synthetic antibodies for specific recognition and crystallization of structured RNA. Proc Natl Acad Sci U S A. Jan. 8, 2008;105 (1):82-7. doi: 10.1073/pnas.0709082105. Epub Dec. 27, 2007. PMID: 18162543; PMCID: PMC2224236.
GenBank; NM_000942; *Homosapiens* peptidylprolyl isomerase B (PPIB), mRNA; 2020.

ANTI-TRANSFERRIN RECEPTOR ANTIBODIES, CONJUGATES THEREOF, AND USES THEREOF

CROSS REFERENCE TO RELATED APPLICATIONS

This application claims the benefit of priority of U.S. Provisional Patent Application Ser. No. 63/624,417, filed on Jan. 24, 2024, U.S. Provisional Patent Application Ser. No. 63/573,151, filed Apr. 2, 2024, U.S. Provisional Patent Application Ser. No. 63/662,243, filed Jun. 20, 2024, and U.S. Provisional Patent Application Ser. No. 63/718,062, filed Nov. 8, 2024, the contents of each of which are incorporated herein by reference in their entirety.

FIELD OF THE INVENTION

The invention relates to compositions comprising anti-transferrin receptor (TfR1) antibodies conjugated to oligonucleotide-based agents and related methods of treating various diseases in the CNS, skeletal muscle, heart, and other tissues using said conjugates or compositions thereof.

SEQUENCE LISTING

This application contains a Sequence Listing (in compliance with Standard ST26), which has been submitted in xml format and is hereby incorporated by reference in its entirety. The xml sequence listing file is named 30728-WO_SeqListing.xml, created Jan. 22, 2025, and is 906 kb in size.

BACKGROUND OF THE INVENTION

RNA interference (RNAi) is a process by which RNA is degraded to silence gene expression. One type of RNAi molecule is short (i.e., <30 nucleotide) double-stranded RNA ("dsRNA") molecules which are present in the cell (Fire et al., 1998, *Nature* 391:806-811). These short dsRNA molecules, called "short interfering RNA" or "siRNA," cause the destruction of messenger RNAs ("mRNAs") which share sequence homology with the siRNA (Elbashir et al., 2001, *Genes Dev*, 15:188-200). It is believed that one strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. The siRNA is apparently recycled much like a multiple-turnover enzyme, with a single siRNA molecule capable of inducing cleavage of approximately 1000 mRNA molecules. siRNA-mediated RNAi degradation of an mRNA is a safe and effective technology for inhibiting expression of a target gene.

RNAi provides a very exciting approach to treating and/or preventing diseases. Some major benefits of RNAi compared with various traditional therapeutic approaches include: the ability of RNAi to target a very particular gene involved in the disease process with high specificity, thereby reducing or eliminating off target effects; RNAi is a normal cellular process leading to highly specific RNA degradation; and interfering RNA can be modified so it does not trigger a host immune response.

Several interfering RNA delivery methods are being tested/developed for in vivo use. For example, siRNAs can be delivered "naked" in saline solution; complexed with polycations, cationic lipids/lipid transfection reagents, or cationic peptides; as components of defined molecular conjugates (e.g., cholesterol-modified siRNA, TAT-DRBD/siRNA complexes); as components of liposomes; and as components of nanoparticles. These approaches have shown varying degrees of success. However, for RNAi to achieve therapeutic success by gene expression knockdown, it should be delivered to afflicted cell types. Thus, there is a need for new and improved methods for targeting RNAi molecules for in vivo delivery to achieve and enhance the therapeutic potential of RNAi.

SUMMARY OF THE INVENTION

The disclosure provides novel anti-transferrin receptor (TfR1) antibodies exhibiting high binding affinity to the target antigen TfR1, and/or high expression yields. The TfR1 antibodies provided herein are suitable for conjugation to oligonucleotide-based agents, such as small interfering RNA, wherein the antibody binds TfR1 to facilitate crossing of the blood brain barrier (BBB), as well as delivery to desired cell types, including but not limited to cells in the CNS, skeletal muscle, and heart. As such, the TfR1 antibody-conjugated interfering RNA of the present disclosure can be used to deliver an interfering RNA molecule to the central nervous system (CNS) of a patient. The present disclosure also provides methods of treatment using the TfR1 antibodies conjugated to interfering RNAs for delivering an interfering RNA molecules in vivo.

Accordingly, one aspect of the present disclosure features an antibody that binds a transferrin receptor (TfR1), the antibody comprising a heavy chain that comprises a heavy chain variable region (VH) and a light chain that comprises a light chain variable region (VL). The VH comprises: (a) a heavy chain complementarity determining region 1 (HC CDR1) set forth as $GX_1TFX_2SYWX_3H$, in which $X_1$ is F or Y; $X_2$ is K, N, or T, and $X_3$ is M or V; (b) a heavy chain complementarity determining region 2 (HC CDR2) set forth as $EINPTNGRX_4NYIEKFKS$ (SEQ ID NO: 23), in which $X_4$ is F, S, T, or V; and (c) a heavy chain complementarity determining region 3 (HC CDR3) set forth as GTRAYHY (SEQ ID NO: 24). The VL comprises: (a) a light chain complementarity determining region 1 (LC CDR1) set forth as $RASDX_5LYX_6NLA$ (SEQ ID NO: 5), in which $X_5$ is G, K, or N, and $X_6$ is R or S; (b) a light chain complementarity determining region 2 (LC CDR2) set forth as $DAX_7X_8LAS$, in which $X_7$ is F, K, R, or T; and $X_8$ is K, L, N, or R; and (c) a light chain complementarity determining region 3 (LC CDR3) set forth as QHFWGTPLT (SEQ ID NO: 13).

In some embodiments, $X_1$ is F or Y; $X_2$ is T; $X_3$ is M; $X_4$ is T or V; $X_5$ is G or K; $X_6$ is S; $X_7$ is T; and $X_8$ is L or K.

In some examples, the antibody comprises the HC CDR1, HC CDR2, and HC CDR3 set forth in Table 2. Alternatively or in addition, the antibody comprises the LC CDR9, LC CDR2, and LC CDR3 set forth in Table 1.

In some examples, the antibody comprises: the HC CDR1, HC CDR2, and HC CDR3 set forth as SEQ ID NOs: 16, 19, and 24, respectively, and the LC CDR1, LC CDR2, and LC CDR3 set forth as SEQ ID NOs: 4, 11, and 13, respectively (i.e., the same HC and LC CDRs as clone Fab0070).

In other examples, the antibody comprises: the HC CDR1, HC CDR2, and HC CDR3 set forth as SEQ ID NOs: 14, 20, and 24, respectively, and the LC CDR1, LC CDR2, and LC CDR3 set forth as SEQ ID NOs: 2, 7, and 13, respectively (i.e., the same HC and LC CDRs as clone Fab0061).

In some embodiments, the anti-TfR1 antibody disclosed herein is a humanized antibody. Such a humanized antibody may comprise the light chain framework regions shown in Table 3. Alternatively or in addition, the antibody comprises the heavy chain framework regions shown in Table 4. In some examples, the anti-TfR1 antibody provided herein may comprise the VH shown in Table 5; and/or wherein the antibody comprises the VL shown in Table 5.

In some instances, the anti-TfR1 antibody provided herein is a full-length antibody, an antigen binding fragment thereof, or a single chain fragment variable (scFv) antibody.

In specific examples, the antibody a Fab molecule, which comprises (a) a heavy chain comprises a VH (e.g., any of those provided in Table 5) and a CH1 heavy chain constant region fragment; and (b) a light chain comprises a VL (e.g., any of those provided in Table 5) and a light chain constant region (CL). In some instances, the CH1 may be of a human IgG heavy chain, for example, comprising the amino acid sequence of ASTKGPSVFPLAPSSKSTSGGTAAL-GCLVKDYFPEPVTVSWNSGALTSGVHTFPAVLQSS GLYS-LSSVVTVPSSSLGTQTYICNVNHKPSNTKVDKRVE-PKSCDKTH (SEQ ID NO: 34). Alternatively or in addition, the CL may be of a human light chain constant region (e.g., a κ or μ chain), for example, comprising the amino acid sequence of RTVAAPSVFIFPPSDEQLKSG-TASVVCLLNNFYPREAKVQWKVD-NALQSGNSQESVTEQ DSKDSTYSLSSTLTL-SKADYEKHKVYACEVTHQGLSSPVTKSFNRGEC (SEQ ID NO: 29).

In one specific example, the anti-Tf1R antibody provided herein may comprise a heavy chain comprising (e.g., consisting of) the amino acid sequence of SEQ ID NO: 61 and a light chain comprising (e.g., consisting of) the amino acid sequence of SEQ ID NO: 62 (e.g., clone Fab0070). In another specific example, the anti-TfR1 antibody may comprise a heavy chain comprising the amino acid sequence of SEQ ID NO: 45 and a light chain comprising the amino acid sequence of SEQ ID NO: 46 (e.g., clone Fab0061).

In some instances, the anti-Tf1R antibody provided herein may comprise an Fc fragment. For example, the anti-Tf1R antibody may be an Fab-Fc molecule, which comprises a VH-CH1 chain, a VL-CL chain, and an Fc fragment linked to either the VH-CH1 chain or the VL-CL chain. One example (xAb000293) is provided in Table 5.

In another aspect, provided herein is a conjugate comprising an antibody that binds a transferrin receptor (TfR1) (anti-TfR1 antibody) and an oligonucleotide-based agent. In some instances, the anti-TfR1 antibody is any of those provided herein (e.g., those listed in Tables 1, 2, and 5, for example, clone Fab0061 and Fab0070, or functional equivalents thereof, which may comprise the same heavy and light chain CDRs as Fab0061 or Fab0070).

In some embodiments, the oligonucleotide-based agent can be directly conjugated to the anti-TfR1 antibody via a covalent bond or a non-covalent bond (e.g., an ionic bond, a hydrogen bond, or a hydrophobic interaction). In some instances, the oligonucleotide-based agent may be conjugated to the antibody via, e.g., a peptide, a polymer, or a nucleic acid binding protein. In some examples, the oligonucleotide-based agent can be conjugated to the anti-TfR1 antibody via a linker. Examples include, but are not limited to, a chemical linker, a peptide linker, a polymer linker, or a nucleic acid-binding polypeptide. In one example, the linker can be a peptide linker, for example, a glycine spacer of 1-4 glycine residues.

The oligonucleotide-based agent in any of the conjugates disclosed herein may comprises one or more chemically modified nucleotides. In some embodiments, the nucleotides may be chemically modified by substitutions with alkyl, alkoxy, amino, deaza, halo, hydroxyl, and/or thiol groups; sugar modifications, one or more non-nucleotides; one or more deoxyribonucleotides; one or more non-phosphodiester linkages; or a combination thereof. In some examples, the oligonucleotide-based agent may comprise one or more sugar modifications, which may comprise 2' OH groups replaced by 2' amino groups, 2' O-methyl groups, 2' methoxyethyl groups, or a 2'-O, 4'-C methylene bridge. In some examples, the oligonucleotide-based agent may comprise one or more non-nucleotides, which may comprise a xanthine, a hypoxanthine, an azapurine, a methylthioadenine, 7-deaza-adenosine or O- and N-modified nucleotides. Alternatively or in addition, the oligonucleotide-based agent may comprise one or more non-phosphodiester linkages, which may comprise one or more nitrogen or sulfur substitutions for oxygen in the phosphate group.

In some examples, the oligonucleotide-based agent in any of the conjugates provided herein can be an RNAi agent comprising a sense strand and an anti-sense strand, which form a double-strand. In some instances, the sense strand is conjugated to the anti-TfR1 antibody, which may be a Fab molecule.

In some instances, the oligonucleotide-based agent such as the RNAi agent may attenuate expression of a target gene of interest. Examples include, but are not limited to, APP, Ataxin-1, Ataxin-2, Ataxin-3, Ataxin-7, androgen receptor, SOD1, Huntingtin, Chromosome 9 open reading frame 72, Leucine-rich repeat serine/threonine-protein kinase 2, complement C3, microtubule-associated protein tau, alpha-2A adrenergic receptor, sodium channel protein type 9 subunit alpha, Apolipoprotein E, alpha-synuclein, probable G-protein coupled receptor 75, RNA-binding protein FUS, GFAP, KCNT1, PRNP, MSH3, RAGE, SNC9A, SCN10A, SCN11A, SORT1, VCP, PIKFYVE, CHMP7, PDE2A, SARM1, NLRP3, GSDME, and DYRK1A. In specific examples, the target gene is APP, ATXN2, ATXN3, AR, SOD1, HTT, C90RF72, LRRK2, C3, MAPT, ADRA2A, SCN9A, APOE, SNCA, GPR75, or FUS.

In some instances, the anti-TfR1 antibody is a Fab molecule, which is conjugated to a cap moiety. The oligonucleotide-based agent is conjugated to a linker. The oligonucleotide-based agent is conjugated to the Fab molecule via the linker. In some examples, the cap moiety has structure of:

(CP-1113)

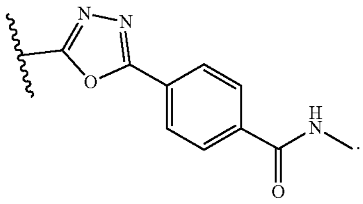

Alternatively or in addition, the linker has a structure of.

L20-p

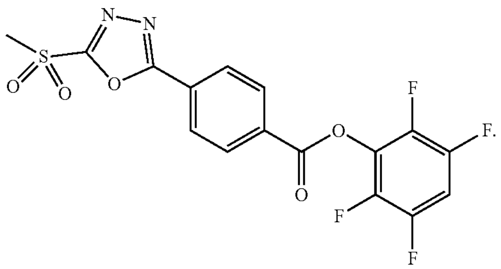

In specific examples, the oligonucleotide-based agent is an RNAi agent comprising a sense strand and an anti-sense strand, which form a double-strand. The sense strand can be conjugated to the linker.

In yet another aspect, the present disclosure provides a pharmaceutical composition comprising an anti-TfR1 antibody or a conjugate thereof (e.g., any of those provided herein) and a pharmaceutically acceptable carrier. The anti-TfR1 antibody may be any of those provided herein, e.g., those listed in Tables 1, 2, and 5, for example, clone Fab0061 and Fab0070, or functional equivalents thereof, which may comprise the same heavy and light chain CDRs as Fab0061 or Fab0070).

Further, provided herein is a method for attenuating expression of a target gene in the brain of a subject, the method comprising administering to a subject in need thereof an effective amount of a conjugate or a pharmaceutical composition comprising such. The conjugate comprises an anti-TfR1 antibody conjugated to an oligonucleotide-based agent. The anti-TfR1 antibody may be any of those provided herein, e.g., those listed in Tables 1, 2, and 5, for example, clone Fab0061 and Fab0070, or functional equivalents thereof, which may comprise the same heavy and light chain CDRs as Fab0061 or Fab0070). The oligonucleotide-based agent (e.g., an RNAi agent) attenuates expression of a target gene of interest, e.g., those provided herein. Any of the conjugates provided herein may be used in the method disclosed herein.

In some embodiments, the subject is a human patient having or suspected of having a central nervous system (CNS) disease. Examples include, but are not limited to, amyotrophic lateral sclerosis (ALS), Alzheimer's disease, Parkinson's disease, Huntington's Disease, dementia, cognitive impairment, frontotemporal dementia, Lewy body disease, cerebral amyloid angiopathy, tauopathies, spinocerebellar ataxia, Alexander's disease, Kennedy's disease, childhood epilepsy, fatal familial insomnia, prion disease, pain, multiple system atrophy, corticobasal degeneration, progressive supranuclear palsy, TDP43 proteinopathies, traumatic brain injury, Down syndrome, neuropathic pain, inherited erythromelalgia, paroxysmal extreme pain disorder, and heritable small fiber neuropathy.

In some embodiments, the conjugate or the pharmaceutical composition comprising such is administered to the subject by intravenous, subcutaneous, intramuscular, intraparenchymal, or intrathecal injection.

Moreover, provided herein is a method for alleviating a CNS disease or disorder, a skeletal muscle disease, a heart disease or disorder, or a disease in other tissues comprising administering to a subject in need thereof an effective amount of any of the conjugates disclosed herein or a pharmaceutical composition comprising such. The conjugate comprises an anti-Tf1R antibody as disclosed herein (e.g., those listed in Tables 1, 2, and 5, for example, clone Fab0061 and Fab0070, or functional equivalents thereof, which may comprise the same heavy and light chain CDRs as Fab0061 or Fab0070) and an oligonucleotide-based agent (e.g., an RNAi agent) that attenuates expression of a target gene of interest, for example, APP, Ataxin-1, Ataxin-2, Ataxin-3, Ataxin-7, androgen receptor, SOD1, Huntingtin, Chromosome 9 open reading frame 72, Leucine-rich repeat serine/threonine-protein kinase 2, complement C3, microtubule-associated protein tau, alpha-2A adrenergic receptor, sodium channel protein type 9 subunit alpha, Apolipoprotein E, alpha-synuclein, probable G-protein coupled receptor 75, RNA-binding protein FUS, GFAP, KCNT1, PRNP, MSH3, RAGE, SNC9A, SCN10A, SCN11A, SORT1, VCP, PIKFYVE, CHMP7, PDE2A, SARM1, NLRP3, GSDME, DYRK1A, DUX4, DM1, ACVR2A, ACVR2B, MSTN, and GYS1. The subject may be a human patient having or suspected of having a CNS disease selected from the group consisting of amyotrophic lateral sclerosis (ALS), Alzheimer's disease, Parkinson's disease, Huntington's Disease, dementia, cognitive impairment, frontotemporal dementia, Lewy body disease, cerebral amyloid angiopathy, tauopathies, spinocerebellar ataxia, Alexander's disease, Kennedy's disease, childhood epilepsy, fatal familial insomnia, prion disease, pain, multiple system atrophy, corticobasal degeneration, progressive supranuclear palsy, TDP43 proteinopathies, traumatic brain injury, Down syndrome, neuropathic pain, inherited erythromelalgia, paroxysmal extreme pain disorder, heritable small fiber neuropathy, or muscular dystrophies or atrophies, including but not limited to Facioscapulohumeral muscular dystrophy (FSHD), Duchenne muscular dystrophy, and myotonic dystrophy type 1, spinal muscular atrophy, or metabolic myopathies, including but not limited to Pompe disease, or neuromuscular junction diseases, including but not limited to Myasthenia gravis (MG), or metabolic syndrome.

Also within the scope of the present disclosure is any of the conjugates provided herein or a pharmaceutical composition comprising such for use in treating a disease such as those disclosed herein or use of the conjugates/pharmaceutical compositions for manufacturing a medicament for use in treating the disease.

In addition, the present disclosure provides a nucleic acid or set of nucleic acids, comprising nucleotide sequences encoding the heavy chain and the light chain of the anti-TfR1 antibody disclosed herein, e.g., those listed in Tables 1, 2, and 5, for example, clone Fab0061 and Fab0070, or functional equivalents thereof, which may comprise the same heavy and light chain CDRs as Fab0061 or Fab0070). In some instances, the nucleic acid or set of nucleic acids is a vector or set of vectors. In some examples, the vector or set of vectors is an expression vector or set of expression vectors. Also provided herein is a host cell comprising the nucleic acid or set of nucleic acids disclosed herein.

Further, the present disclosure features a method for producing an anti-TfR1 antibody, comprising: (i) culturing the host cell that carries coding nucleic acid(s) for any of the anti-TfR1 antibodies provided herein (e.g., those listed in Tables 1, 2, and 5, for example, clone Fab0061 and Fab0070, or functional equivalents thereof, which may comprise the same heavy and light chain CDRs as Fab0061 or Fab0070) under conditions allowing for expression of the anti-TfR1 antibody; and (ii) harvesting the anti-TfR1 antibody thus produced.

Additional embodiments of the present disclosure are provided below.

Embodiment 1. An antibody that binds a transferrin receptor (TfR1), the antibody comprising a heavy chain that comprises a heavy chain variable region (VH) and a light chain that comprises a light chain variable region (VL);

wherein the VH comprises:

a heavy chain complementarity determining region 1 (HC CDR1) set forth as $GX_1TFX_2SYWX_3H$, in which $X_1$ is F or Y; $X_2$ is K, N, or T, and $X_3$ is M or V;

a heavy chain complementarity determining region 2 (HC CDR2) set forth as $EINPTNGRX_4NYIEKFKS$ (SEQ ID NO: 23), in which $X_4$ is F, S, T, or V; and a heavy chain complementarity determining region 3 (HC CDR3) set forth as GTRAYHY (SEQ ID NO: 24); and wherein the VL comprises:

a light chain complementarity determining region 1 (LC CDR1) set forth as $RASDX_5LYX_6NLA$ (SEQ ID NO: 5), in which $X_5$ is G, K, or N, and $X_6$ is R or S;

a light chain complementarity determining region 2 (LC CDR2) set forth as $DAX_7X_8LAS$, in which $X_7$ is F, K, R, or T; and $X_8$ is K, L, N, or R; and a light chain complementarity determining region 3 (LC CDR3) set forth as QHFWGTPLT (SEQ ID NO: 13).

Embodiment 2. The antibody of embodiment 1, wherein $X_1$ is F or Y; $X_2$ is T; $X_3$ is M; $X_4$ is T or V; $X_5$ is G or K; $X_6$ is S; $X_7$ is T; and $X_8$ is L or K.

Embodiment 3. The antibody of embodiment 1, wherein the antibody comprises the HC CDR1, HC CDR2, and HC CDR3 of any one of Fab0070, Fab0061, Fab0060, Fab0062, Fab0063, Fab0064, Fab0065, Fab0066, Fab0067, Fab0068, Fab0069, Fab0071, Fab0072, Fab0073, Fab0074, Fab0165, Fab0166, Fab0167, or Fab0168 as set forth in Table 2; and/or wherein the antibody comprises the LC CDR1, LC CDR2, and LC CDR3 of any one of Fab0070, Fab0061, Fab0060, Fab0062, Fab0063, Fab0064, Fab0065, Fab0066, Fab0067, Fab0068, Fab0069, Fab0071, Fab0072, Fab0073, Fab0074, Fab0165, Fab0166, Fab0167, or Fab0168, set forth in Table 1.

Embodiment 4. The antibody of embodiment 3, wherein the antibody comprises:

(a) the HC CDR1, HC CDR2, and HC CDR3 set forth as SEQ ID NOs: 16, 19, and 24, respectively, and the LC CDR1, LC CDR2, and LC CDR3 set forth as SEQ ID NOs: 4, 11, and 13, respectively; or (b) the HC CDR1, HC CDR2, and HC CDR3 set forth as SEQ ID NOs: 14, 20, and 24, respectively, and the LC CDR1, LC CDR2, and LC CDR3 set forth as SEQ ID NOs: 2, 7, and 13, respectively.

Embodiment 5. The antibody of any one of embodiments 1-4, wherein the antibody is a humanized antibody; optionally wherein the antibody comprises the light chain framework regions shown in Table 3 and/or the heavy chain framework regions shown in Table 4.

Embodiment 6. The antibody of embodiment 5, wherein the antibody comprises any one of the VH sequences shown in Table 5; and/or wherein the antibody comprises any one of the VL sequences shown in Table 5.

Embodiment 7. The antibody of any one of embodiments 1-6, wherein the antibody is a full-length antibody, an antigen binding fragment thereof, or a single chain fragment variable (scFv) antibody.

Embodiment 8. The antibody of any one of embodiments 1-7, wherein the antibody is a Fab molecule; wherein the heavy chain comprises the VH and a CH1 heavy chain constant region fragment; and wherein the light chain comprises the VL and a light chain constant region (CL).

Embodiment 9. The antibody of embodiment 8, wherein the CH1 comprises the amino acid sequence of ASTKGPSVFPLAPSSKSTSGGTAALGCLVKDYF-PEPVTVSWNSGALTSGVHTFPAVLQSS GLYS-LSSVVTVPSSSLGTQTYICNVNHKPSNTKVDKRVE-PKSCDKTH (SEQ ID NO: 34);

and/or wherein the CL comprises the amino acid sequence of RTVAAPSVFIFPPSDEQLKSGTASVVCLLNNFY-PREAKVQWKVDNALQSGNSQESVTEQ DSKDS-TYSLSSTLTLSKADYEKHKVYACE-VTHQGLSSPVTKSFNRGEC (SEQ ID NO: 29).

Embodiment 10. The antibody of embodiment 8 or 9, wherein the VH comprises the amino acid sequence of EVQLVESGGGLVQPGGSLRLSCATSGFTFT-SYWMHWVRQAPGKGLEWVAEINPTNGRT NYIEKFKSRITLSVDKSKSTVYLQMNSLRAED-TAVYYCARGTRAYHYWGQGTLVTVSS (SEQ ID NO: 59), and/or wherein the VL comprises the amino acid sequence of DIQLTQSPSSLSASVGDRVTITCRASDK-LYSNLAWYQQKPGKAPKLLIYDATLLASGVPS RFSGSGSGTDYTLTISSLQPEDFA-TYYCQHFWGTPLTFGQGTKVEIK (SEQ ID NO: 60).

Embodiment 11. The antibody of embodiment 8 or 9, wherein:

(a) the heavy chain comprises the amino acid sequence of SEQ ID NO: 61 and the light chain comprises the amino acid sequence of SEQ ID NO: 62; or (b) the heavy chain comprises the amino acid sequence of SEQ ID NO: 45 and the light chain comprises the amino acid sequence of SEQ ID NO: 46.

Embodiment 12. The antibody of any one of embodiments 1-11, wherein the antibody comprises an Fe fragment, optionally wherein the antibody is a Fab-Fc molecule.

Embodiment 13. A conjugate comprising an antibody that binds a transferrin receptor (TfR1) (anti-TfR1 antibody) and an oligonucleotide-based agent, wherein the anti-TfR1 antibody is set forth in any one of embodiments 1-12.

Embodiment 14. The conjugate of embodiment 13, wherein the oligonucleotide-based agent is directly conjugated to the anti-TfR1 antibody via a covalent bond or a non-covalent bond.

Embodiment 15. The conjugate of embodiment 13, wherein the oligonucleotide-based agent is conjugated to the anti-TfR1 antibody via a linker, which optionally is a chemical linker, a peptide linker, a polymer linker, or a nucleic acid-binding polypeptide.

Embodiment 16. The conjugate of embodiment 13, wherein the linker is a peptide linker, which is a glycine spacer of 1-4 glycine residues.

Embodiment 17. The conjugate of any one of embodiments 13-16, wherein the oligonucleotide-based agent comprises one or more chemically modified nucleotides.

Embodiment 18. The conjugate of embodiment 17, wherein the nucleotides are chemically modified by substitutions with alkyl, alkoxy, amino, deaza, halo, hydroxyl, and/or thiol groups; sugar modifications, one or more non-nucleotides; one or more deoxyribonucleotides; one or more non-phosphodiester linkages; or a combination thereof.

Embodiment 19. The conjugate of embodiment 18, wherein:

the sugar modifications comprise 2' OH groups replaced by 2' amino groups, 2' O-methyl groups, 2' fluoro groups, 2' methoxyethyl groups, or a 2'-O, 4'-C methylene bridge;

the one or more non-nucleotides comprise a xanthine, a hypoxanthine, an azapurine, a methylthioadenine, 7-deaza-adenosine or O- and N-modified nucleotides; and/or the one or more non-phosphodiester linkages comprise one or more nitrogen or sulfur substitutions for oxygen in the phosphate group.

Embodiment 20. The conjugate of any one of embodiments 13-19, wherein the oligonucleotide-based agent is an RNAi agent comprising a sense strand and an anti-sense strand, which form a double-strand.

Embodiment 21. The conjugate of embodiment 20, wherein the RNAi agent attenuates expression of a target gene selected from the group consisting of APP, Ataxin-1, Ataxin-2, Ataxin-3, Ataxin-7, androgen receptor, SOD1, Huntingtin, Chromosome 9 open reading frame 72, Leucine-rich repeat serine/threonine-protein kinase 2, complement C3, microtubule-associated protein tau, alpha-2A adrenergic receptor, sodium channel protein type 9 subunit alpha, Apolipoprotein E, alpha-synuclein, probable G-protein coupled receptor 75, RNA-binding protein FUS, GFAP, KCNT1, PRNP, MSH3, RAGE, SNC9A, SCN10A, SCN11A, SORT1, VCP, PIKFYVE, CHMP7, PDE2A, SARM1, NLRP3, GSDME, and DYRK1A.

Embodiment 22. The conjugate of embodiment 21, wherein the target gene is selected from the group consisting of APP, ATXN2, ATXN3, AR, SOD1, HTT, C90RF72, LRRK2, C3, MAPT, ADRA2A, SCN9A, APOE, SNCA, GPR75, and FUS.

Embodiment 23. The conjugate of any one of embodiments 20-22, wherein the sense strand is conjugated to the anti-TfR1 antibody, wherein the anti-TfR1 antibody is a Fab molecule.

Embodiment 24. The conjugate of any one of embodiments 13-23, wherein the anti-TfR1 antibody is a Fab molecule; wherein the oligonucleotide-based agent is conjugated to a linker of the formula:

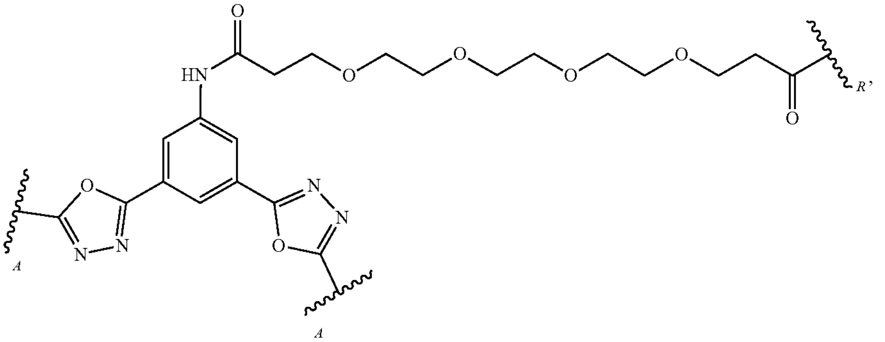

wherein ⌇$_A$ represents a point of attachment to the Fab molecule, and ⌇$_R$ represents a point of attachment of the linker to the oligonucleotide-based agent portion of the conjugate.

Embodiment 25. The conjugate of any one of embodiments 13-23, wherein the anti-TfR1 antibody is a Fab molecule, which comprises a cap moiety; wherein the oligonucleotide-based agent is conjugated to a linker, and wherein the oligonucleotide-based agent is conjugated to the Fab molecule via the linker.

Embodiment 26. The conjugate of embodiment 25, wherein the cap moiety is of the formula:

(CP-1113)

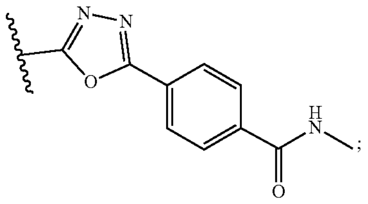

and/or wherein the linker has a structure of

L20

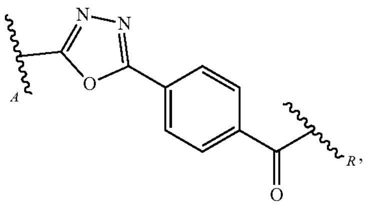

wherein ⌇$_A$ represents a point of attachment to the Fab molecule, and ⌇$_R$ represents a point of attachment of the linker to the oligonucleotide-based agent portion of the conjugate.

Embodiment 27. The conjugate of embodiment 25 or embodiment 26, wherein the oligonucleotide-based agent is an RNAi agent comprising a sense strand and an anti-sense strand, which form a double-strand; and wherein the sense strand is conjugated to the linker.

Embodiment 28. A pharmaceutical composition comprising an anti-TfR1 antibody or a conjugate thereof and a pharmaceutically acceptable carrier, wherein the anti-TfR1 antibody is set forth in any one of embodiments 1-12.

Embodiment 29. The pharmaceutical composition of embodiment 27, which comprises a conjugate of the anti-TfR1 antibody, wherein the conjugate is set forth in any one of embodiments 13-27.

Embodiment 30. A method for attenuating expression of a target gene in the brain of a subject, comprising administering to a subject in need thereof an effective amount of a conjugate or a pharmaceutical composition comprising such, wherein the conjugate comprises an anti-TfR1 antibody conjugated to an oligonucleotide-based agent, wherein the anti-TfR1 antibody is set forth in any one of embodiments 1-12; and wherein the oligonucleotide-based agent attenuates expression of the target gene.

Embodiment 31. The method of embodiment 30, wherein the conjugate is set forth in any one of embodiments 12-27.

Embodiment 32. The method of embodiment 30 or embodiment 31, wherein the subject is a human patient having or suspected of having a central nervous system (CNS) disease.

Embodiment 33. The method of embodiment 32, wherein the CNS disease is selected from the group consisting of amyotrophic lateral sclerosis (ALS), Alzheimer's disease, Parkinson's disease, Huntington's Disease, dementia, cognitive impairment, frontotemporal dementia, Lewy body disease, cerebral amyloid angiopathy, tauopathies, spinocerebellar ataxia, Alexander's disease, Kennedy's disease, childhood epilepsy, fatal familial insomnia, prion disease, pain, multiple system atrophy, corticobasal degeneration, progressive supranuclear palsy, TDP43 proteinopathies, traumatic brain injury, Down syndrome, neuropathic pain, inherited erythromelalgia, paroxysmal extreme pain disorder, and heritable small fiber neuropathy.

Embodiment 34. The method of any one of embodiments 30-33, wherein the conjugate or the pharmaceutical composition comprising such is administered to the subject by intravenous, subcutaneous, intramuscular, intraparenchymal, or intrathecal injection.

Embodiment 35. A method for alleviating a CNS disease, comprising administering to a subject in need thereof an effective amount of a conjugate set forth in any one of embodiments 12-26 or a pharmaceutical composition comprising such;

wherein the conjugate comprises an oligonucleotide-based agent that attenuates expression of a target gene selected from the group consisting of APP, Ataxin-1, Ataxin-2, Ataxin-3, Ataxin-7, androgen receptor, SOD1, Huntingtin, Chromosome 9 open reading frame 72, Leucine-rich repeat serine/threonine-protein kinase 2, complement C3, microtubule-associated protein tau, alpha-2A adrenergic receptor, sodium channel protein type 9 subunit alpha, Apolipoprotein E, alpha-synuclein, probable G-protein coupled receptor 75, RNA-binding protein FUS, GFAP, KCNT1, PRNP, MSH3, RAGE, SNC9A, SCN10A, SCN11A, SORT1, VCP, PIKFYVE, CHMP7, PDE2A, SARM1, NLRP3, GSDME, and DYRK1A; and wherein the subject has or is suspected of having a CNS disease selected from the group consisting of amyotrophic lateral sclerosis (ALS), Alzheimer's disease, Parkinson's disease, Huntington's Disease, dementia, cognitive impairment, frontotemporal dementia, Lewy body disease, cerebral amyloid angiopathy, tauopathies, spinocerebellar ataxia, Alexander's disease, Kennedy's disease, childhood epilepsy, fatal familial insomnia, prion disease, pain, multiple system atrophy, corticobasal degeneration, progressive supranuclear palsy, TDP43 proteinopathies, traumatic brain injury, Down syndrome, neuropathic pain, inherited erythromelalgia, paroxysmal extreme pain disorder, and heritable small fiber neuropathy.

Embodiment 36. A method for attenuating expression of a target gene in the skeletal muscle of a subject, comprising administering to a subject in need thereof an effective amount of a conjugate or a pharmaceutical composition comprising such, wherein the conjugate comprises an anti-TfR1 antibody conjugated to an oligonucleotide-based agent, wherein the anti-TfR1 antibody is set forth in any one of embodiments 1-12; and wherein the oligonucleotide-based agent attenuates expression of the target gene.

Embodiment 37. The method of embodiment 36, wherein the target gene is selected from the group consisting of DUX4, DM1, ACVR2A, ACVR2B, MSTN, and GYS1.

Embodiment 38. The method of embodiment 36 or 37, wherein the subject is a human patient having or suspected of having a skeletal muscle disease.

Embodiment 39. The method of embodiment 38, wherein the skeletal muscle disease is selected from the group consisting of Facioscapulohumeral muscular dystrophy (FSHD), Duchenne muscular dystrophy, and myotonic dystrophy type 1, spinal muscular atrophy, or metabolic myopathies, including but not limited to Pompe disease, or neuromuscular junction diseases, including but not limited to Myasthenia gravis (MG), or metabolic syndrome.

Embodiment 40. A nucleic acid or set of nucleic acids, comprising nucleotide sequences encoding the heavy chain and the light chain of the anti-TfR1 antibody set forth in any one of embodiments 1-12.

Embodiment 41. The nucleic acid or set of nucleic acids of embodiment 40, which is a vector or set of vectors.

Embodiment 42. The nucleic acid or set of nucleic acids of embodiment 41, wherein the vector or set of vectors is an expression vector or set of expression vectors.

Embodiment 43. A host cell comprising the nucleic acid or set of nucleic acids set forth in any one of embodiments 40-42.

Embodiment 44. A method for producing an anti-TfR1 antibody, comprising:

(i) culturing the host cell of embodiment 43 under conditions allowing for expression of the anti-TfR1 antibody; and (ii) harvesting the anti-TfR1 antibody thus produced.

Specific preferred embodiments of the invention will become evident from the following more detailed description of certain preferred embodiments and the claims.

BRIEF DESCRIPTION OF THE DRAWINGS

These and other features, aspects, and advantages of the present disclosure may be better understood when the following detailed description is read with reference to the accompanying drawings.

DETAILED DESCRIPTION OF THE INVENTION

Figure 1:
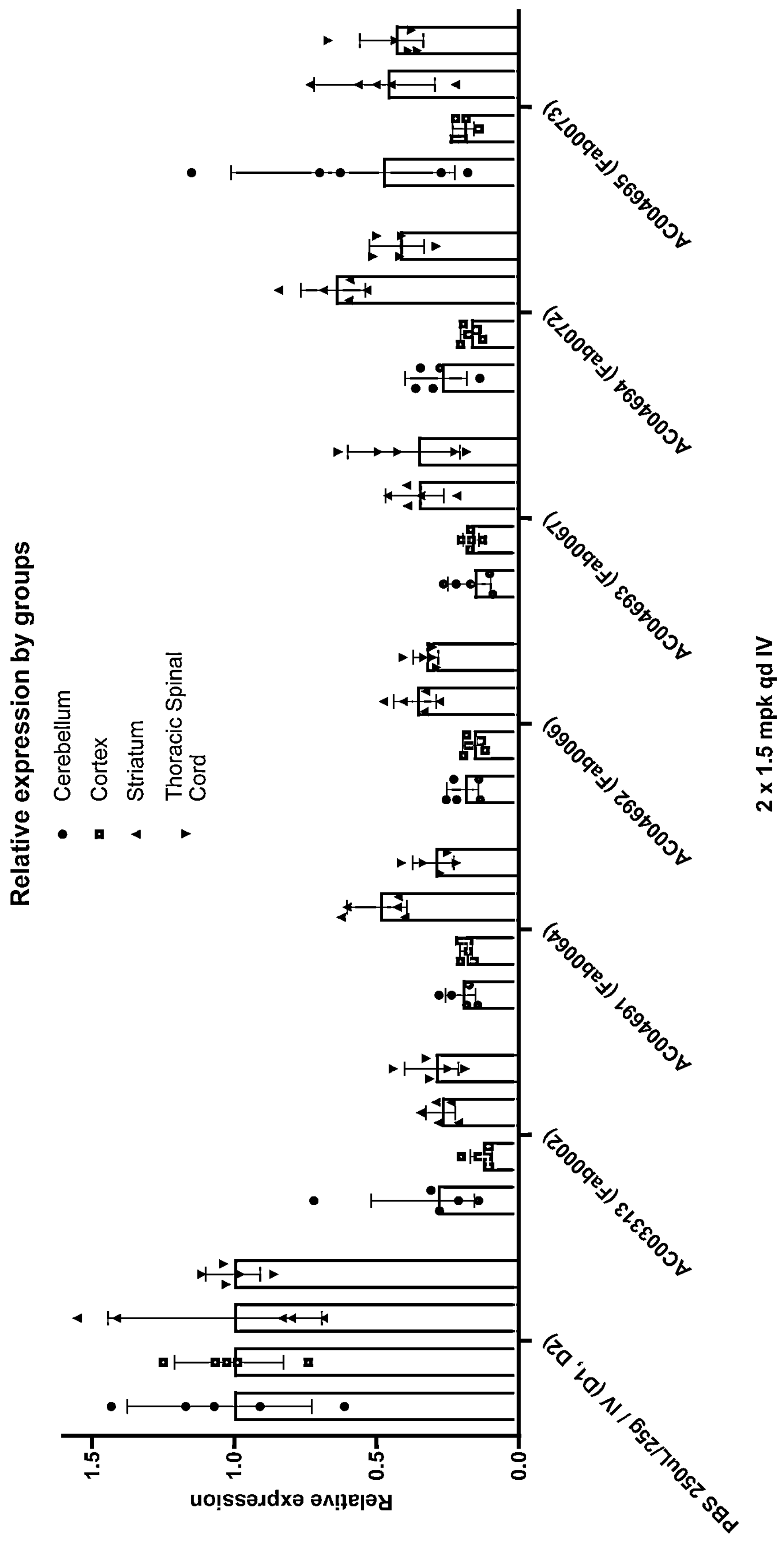
FIG. 1 shows relative androgen receptor (AR) mRNA expression knockdown after the delivery of select TfR1-targeting Fabs conjugated to siRNA with the antisense strand complementary to androgen receptor mRNA relative to control siRNA in different brain regions.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3.sup.rd Edition or a dictionary known to those of skill in the art, such as the Oxford Dictionary of Biochemistry and Molecular Biology (Ed. Anthony Smith, Oxford University Press, Oxford, 2004).

As used herein, all percentages are percentages by weight, unless stated otherwise. As used herein and unless otherwise indicated, the terms "a" and "an" are taken to mean "one", "at least one" or "one or more". Unless otherwise required by context, singular terms used herein shall include pluralities and plural terms shall include the singular.

The term "receptor" as used herein is intended to encompass the entire receptor or ligand-binding portions thereof. These portions of the receptor particularly include those regions sufficient for specific binding of the ligand to occur, including those regions capable of being recognized by an antibody or antibody fragments.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody", e.g., anti-TfR1 antibody, encompasses not only intact (e.g., full-length) polyclonal or monoclonal antibodies, but also antigen-binding fragments thereof (such as Fab, Fab', F(ab')2, Fv), single-chain antibody (scFv), fusion proteins comprising an antibody portion, humanized antibodies, chimeric antibodies, diabodies, single domain antibody (e.g., nanobody), single domain antibodies (e.g., a VH only antibody), multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody, e.g., anti-TfR1 antibody, includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The term "Fab" as used herein refers to the fragment antigen-binding (Fab) region that binds to the TfR1 antigen, and includes 6 complementary determining regions (CDRs), wherein 3 CDRs are on the variable light chain (VL), and 3 CDRs are on the variable heavy chain (VII).

The term "ligand" is defined as any molecule or atom that binds to a receiving molecule for example binding to proteins, nucleotides, or fragments, binding domains, or complements thereof.

The term "protein" as used herein includes peptides, polypeptides, consensus molecules, fusion proteins, purified naturally occurring proteins, artificially synthesized proteins, recombinant proteins, antibodies, antibody fragments, and analogs, derivatives or combinations thereof.

The term "antigen binding fragment" (e.g., Fab) is further intended to encompass fully humanized and chimeric antibody fragments comprising portions from more than one species, bifunctional antibody fragments, etc.

The term "HA2 peptide" means a peptide comprising the N-terminal 20 amino acids of influenza virus hemagglutinin protein.

The term "conjugate" is defined as consisting of two or more molecules; or two or more entities that are coupled together. Preferably, the two molecules or entities are conjugated by non-specific or specific protein-protein interaction, by covalent bonding, by non-covalent bonding or by coordinating chemical bonding. In the context of the present invention, the first molecule may be an interfering RNA molecule, whereas the second molecule may be a ligand for a receptor on a target cell as defined herein. In some embodiments, the term conjugate includes TfR1 Fab coupled to an oligonucleotide-based agent, such as an siRNA, which may also include a linker and/or peptide or protein for release of the oligonucleotide-based agent from the endosome as described herein.

As used herein, the terms "interfering RNA" and "interfering RNA molecule" refer to all RNA or RNA-like molecules that can interact with RISC and participate in RISC-mediated changes in gene expression.

The term "siRNA" as used herein refers to a double-stranded interfering RNA unless otherwise noted.

As used herein, the term "therapeutically effective amount" refers to the amount of interfering RNA or a pharmaceutical composition comprising an interfering RNA determined to produce a therapeutic response in a mammal. Such therapeutically effective amounts are readily ascertained by one of ordinary skill in the art and using methods as described herein.

The phrase "attenuating expression" with reference to a gene or an mRNA as used herein means administering or expressing an amount of interfering RNA (e.g., an siRNA)

to reduce translation of a target mRNA into protein, either through mRNA cleavage or through direct inhibition of translation.

The terms "inhibit," "silencing," and "attenuating" as used herein refer to a measurable reduction in expression of a target mRNA or the corresponding protein as compared with the expression of the target mRNA or the corresponding protein in the absence of an interfering RNA of the invention.

The term "knockdown" refers to the reduction in expression of the target mRNA or the corresponding protein.

The phrases "target sequence" and "target mRNA" as used herein refer to the mRNA or the portion of the mRNA sequence that can be recognized by an interfering RNA used in a method of the invention, whereby the interfering RNA can silence gene expression as discussed herein.

The term "CNS disorder" as used herein includes conditions or disorders associated with the central nervous system (CNS) including but not limited to the brain and spinal cord of a patient. In some embodiments, the CNS disorder is selected from amyotrophic lateral sclerosis (ALS), Alzheimer's disease, Parkinson's disease, Huntington's Disease, dementia, cognitive impairment, frontotemporal dementia, Lewy body disease, cerebral amyloid angiopathy, tauopathies, spinocerebellar ataxia, Alexander's disease, Kennedy's disease, childhood epilepsy, fatal familial insomnia, prion disease, pain, multiple system atrophy, corticobasal degeneration, progressive supranuclear palsy, TDP43 proteinopathies, traumatic brain injury, Down syndrome, neuropathic pain, inherited erythromelalgia, paroxysmal extreme pain disorder, and heritable small fiber neuropathy.

The term "skeletal muscle disorder" as used herein includes conditions or disorders associated with skeletal muscle tissue, including but not limited to muscular dystrophies, including but not limited to FSHD, myotonic dystrophy type 1, and Duchenne muscular dystrophy.

The term "patient" as used herein means a human or other mammal having a CNS disorder or at risk of having a CNS disorder.

As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

The transferrin receptor (TfR1) is an integral membrane glycoprotein that mediates the uptake of iron by individual cells. A correlation exists between the number of receptors on the surface of a cell and cellular proliferation, with the highest number of receptors being on actively growing cells and the lowest number being on resting and terminally differentiated cells. Monoclonal antibody binding (Teh et al. *FEBS J.* 272:6344-635[3], 2005) and hydroxyl radical-mediated protein footprinting (Liu et al. *Biochemistry* 42:12447-12454, 2003) suggest that the TfR1-binding domain of Tf is located within the C-lobe, residues 334-679 of human Tf. Residues 365-401 (especially 381-401), 415-433, and 457-470 appear to be particularly important for receptor binding.

Targeting the TfR1 receptor is a promising approach to facilitate delivery of drug across the blood-brain-barrier (BBB) to brain. Provided herein are anti-TfR1 antibodies having high binding affinity to TfR1 and other superior features also provided herein, e.g., high expression yields. It is reported herein that such anti-TfR1 antibodies successfully facilitated delivery of exemplary siRNA molecules conjugated thereto to brain cells, thereby attenuating expression of the genes targeted by the siRNAs. Accordingly, the anti-TfR1 antibodies provided herein can be used to obtain efficient drug delivery to the brain, thereby solving the biggest challenge associated with developing therapeutic agents for treating central nervous system (CNS) diseases.

I. Anti-TfR1 Fabs and Anti-TfR1 Antibodies

The present disclosure provides antibodies binding to TfR1, for example, human TfR1 In some embodiments, the anti-TfR1 antibodies disclosed herein are capable of binding to TfR1 expressed on cell surface, for example, on brain endothelial cells. As such, the antibodies disclosed herein may be used for facilitating delivery of therapeutic or diagnostic agents conjugated to the antibody to brain. In some instances, the anti-TfR1 antibodies provided herein may also be used for detecting present of the TfR1 receptor, either in vitro or in vivo. As used herein, the term "anti-TfR1 antibody" refers to any antibody capable of binding to a TfR1 polypeptide (e.g., a TfR11 polypeptide expressed on cell surface such as on brain endothelial cells), which can be of a suitable source, for example, human or a non-human mammal (e.g., mouse, rat, rabbit, primate such as monkey, etc.).

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Imnmunological Interest, Fifth Edition*, U.S. Department of Health and Human Services, NIH Publication No. 91-3242, Chothia et al., (1989) Nature 342:877; Chothia, C. et al.

(1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs).

The anti-TfR1 antibody described herein may be a full-length antibody, which contains two heavy chains and two light chains, each including a variable domain and a constant domain. Alternatively, the anti-TfR1 antibody can be an antigen-binding fragment of a full-length antibody. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883.

In some embodiments, the anti-TfR1 antibody provided here is a TfR1 fragment antigen-binding region (Fab) that binds with specificity to the TfR1. In some examples, the TfR1-specific Fab binds to TfR1 on brain endothelial cells. In some embodiments, the TfR1-specific Fab are capable of recognizing and binding with specificity to one or more epitopes on the TfR1.

The anti-TfR1 antibody discloses herein such as the TfR1-specific Fab may bind competitively to TfR1 with transferrin (Tf), the physiological TfR1 ligand. Upon binding of the Fab to TfR1 on a cell surface, transfer of the Fab and the attached interfering RNA enters the cell through constitutive clathrin-mediated endocytosis.

The antibodies described herein can be of a suitable origin, for example, murine, rat, or human. Such antibodies are non-naturally occurring, i.e., would not be produced in an animal without human act (e.g., immunizing such an animal with a desired antigen or fragment thereof or isolated from antibody libraries). Any of the antibodies described herein, e.g., anti-TfR1antibody, can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In some embodiments, the anti-TfR1 antibodies are human antibodies, which may be isolated from a human antibody library or generated in transgenic mice. For example, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Amgen, Inc. (Fremont, Calif.) and HuMAb-Mouse™ and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the antibody library display technology, such as phage, yeast display, mammalian cell display, or mRNA display technology as known in the art can be used to produce human antibodies and antibody fragments in vitro, from immunoglobulin variable (V) domain gene repertoires from unimmunized donors.

In other embodiments, the anti-TfR1 antibodies may be humanized antibodies. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. In general, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, one or more Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In some instances, the humanized antibody may comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation. Methods for constructing humanized antibodies are also well known in the art. See, e.g., Queen et al., Proc. Natl. Acad. Sci. USA, 86:10029-10033 (1989).

In some embodiments, the anti-TfR1 antibodies described herein specifically bind to the corresponding target antigen (here TfR1) or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (TfR1) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (i.e., only baseline binding activity can be detected in a conventional method).

In some embodiments, an anti-TfR1 antibody as described herein has a suitable binding affinity for the target antigen (e.g., TfR1) or antigenic epitopes thereof. As used herein, "binding affinity" refers to the apparent association constant or $K_A$. The $K_A$ is the reciprocal of the dissociation constant ($K_D$). The anti-TfR1 antibody described herein may have a binding affinity ($K_D$) of at least 2 nM, 1 nM, 0.5 nM, 0.1 nM, or lower for TfR1. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 90, 100, 500, 1000, 10,000 or 105 fold. In some embodiments, any of the anti-TfR1 antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM IIEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation: [Bound]=[Free]/(Kd+[Free]).

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

A. Exemplary Anti-TfR1 Antibodies

In some embodiments, the anti-TfR1 antibodies provided herein are humanized antibodies derived from a mouse monoclonal antibody clone. Briefly, the heavy chain and light chain complementarity determining domains of the mouse parent are grafted to human consensus VH and VL frameworks to produce a parent humanized antibody. A humanized library was generated using Kunkel mutagenesis to introduce variations at certain framework regions positions and CDR-FR junction positions was constructed and screened for clones exhibiting high binding affinity to human TfR1. mab1G derived from the screening showed the highest binding affinities and thus was selected for further affinity maturation. See Examples below. Exemplary anti-TfR1 antibodies derived from affinity maturation, comprising variations in certain CDRs relative to the mab1G parent, exhibited further enhanced binding affinity. Certain clones, e.g., Fab0061 and Fab0070, showed superior rodent and cyno cross-activity over the mouse parent (Fab version). Further, certain clones such as Fab0061 and Fab0070 showed about 4 folds increase in expression yields compared to the mouse parent in Fab format.

Accordingly, the anti-TfR1 antibodies provided herein (e.g., in Fab format) may comprise a heavy chain that comprises a heavy chain variable region (VH) and a light chain that comprises a light chain variable region (VL), each of which comprise three complementarity determining regions (CDRs), CDR1, CDR2, and CDR3. In some instances, the anti-TfR1 antibody contains a heavy chain CDR3 set forth as GTRAY-HY (SEQ ID NO: 24) and a light chain CDR3 set forth as QHFWGTPLT (SEQ ID NO: 13). The anti-TfR1 antibody may further comprise a heavy chain CDR1 having a consensus motif of $GX_1TFX_2SYWX_3H$, in which $X_1$ is F or Y; $X_2$ is K, N, or T, and $X_3$ is M or V and a heavy chain CDR2 having a consensus motif of EINPTNGRX4NYIEKFKS (SEQ ID NO: 23), in which $X_4$ is F, S, T, or V. Alternatively or in addition, the anti-TfR1 antibody may further comprise a light chain CDR1 having a consensus motif of $RASDX_5LYX_6NLA$ (SEQ ID NO: 5), in which $X_5$ is G, K, or N, and $X_6$ is R or S; and a light chain CDR2 having a consensus motif of $DAX_7X_8LAS$, in which $X_7$ is F, K, R, or T; and $X_8$ is K, L, N, or R. In some examples, $X_1$ is F or Y; $X_2$ is T; $X_3$ is M; $X_4$ is T or V; $X_5$ is G or K; $X_6$ is S; $X_7$ is T; and $X_8$ is L or K in the consensus motifs. In some embodiments, $X_1$ is F; $X_2$ is T; $X_3$ is M; and $X_4$ is T in the consensus motifs. In some embodiments, $X_5$ is K; $X_6$ is S; $X_7$ is T; and $X_8$ is L in the consensus motifs. In some embodiments, $X_1$ is F; $X_2$ is T; $X_3$ is M; $X_4$ is T; $X_5$ is K; $X_6$ is S; $X_7$ is T; and $X_8$ is L in the consensus motifs.

In some embodiments, $X_1$ is F. In some embodiments, $X_1$ is Y.

In some embodiments, $X_2$ is K. In some embodiments, $X_2$ is N. In some embodiments, $X_2$ is T.

In some embodiments, $X_3$ is M. In some embodiments, $X_3$ is V.

In some embodiments, $X_4$ is F. In some embodiments, $X_4$ is S. In some embodiments, $X_4$ is T. In some embodiments, $X_4$ is V.

In some embodiments, $X_5$ is G. In some embodiments, $X_5$ is K. In some embodiments, $X_5$ is N.

In some embodiments, $X_6$ is R. In some embodiments, $X_6$ is S.

In some embodiments, $X_7$ is F. In some embodiments, $X_7$ is K. In some embodiments, $X_7$ is R. In some embodiments, $X_7$ is T.

In some embodiments, $X_8$ is K. In some embodiments, $X_8$ is L. In some embodiments, $X_8$ is N. In some embodiments, $X_8$ is R.

Exemplary combinations of light chain CDRs of the anti-TfR1 antibodies provided herein are provided in Table 1 below. Exemplary combinations of heavy chain CDRs of the anti-TfR1 antibodies provided herein are provided in Table 2 below. In some instances, the anti-TfR1 antibodies may comprise one or more of the heavy chain and light chain framework regions provided in Tables 3 and 4 below.

In some embodiments, the anti-TfR1 antibodies described herein bind to the same epitope of a TfR1 polypeptide as any of the exemplary antibodies described herein (for example, those disclosed in Table 5, e.g., clone Fab0061 or Fab0070) or compete against the exemplary antibody from binding to the TfR1 antigen. In some examples, the exemplary antibody is Fab0061. In other examples, the exemplary antibody is Fab0070. An "epitope" refers to the site on a target antigen that is recognized and bound by an antibody. The site can be entirely composed of amino acid components, entirely composed of chemical modifications of amino acids of the protein (e.g., glycosyl moieties), or composed of combinations thereof. Overlapping epitopes include at least one common amino acid residue. An epitope can be linear, which is typically 6-15 amino acids in length. Alternatively, the epitope can be conformational. The epitope to which an antibody binds can be determined by routine technology, for example, the epitope mapping method (see, e.g., descriptions below). An antibody that binds the same epitope as an exemplary antibody described herein may bind to exactly the same epitope or a substantially overlapping epitope (e.g., containing less than 3 non-overlapping amino acid residues, less than 2 non-overlapping amino acid residues, or only 1 non-overlapping amino acid residue) as the exemplary antibody. Whether two antibodies compete against each other from binding to the cognate antigen can be determined by a competition assay, which is well known in the art.

In some examples, the anti-TfR1 antibody comprises the same $V_H$ and/or $V_L$ CDRs as an exemplary antibody described herein (e.g., those provided in Table 5 such as Fab0061 or Fab0070). Two antibodies having the same $V_H$ and/or $V_L$ CDRs means that their CDRs are identical when determined by the same approach (e.g., the Kabat approach, the Chothia approach, the AbM approach, the Contact approach, or the IMGT approach as known in the art. See, e.g., bioinf.org.uk/abs/). Such anti-TfR1 antibodies may have the same $V_H$, the same VL, or both as compared to an exemplary antibody described herein.

Also within the scope of the present disclosure are functional variants of any of the exemplary anti-TfR1 antibodies as disclosed herein. Such functional variants are substantially similar to the exemplary antibody, both structurally and functionally. A functional variant comprises substantially the same $V_H$ and $V_L$ CDRs as the exemplary antibody. For example, it may comprise only up to 8 (e.g., 8, 7, 6, 5, 4, 3, 2, or 1) amino acid residue variations in the total CDR regions of the antibody and binds the same epitope of TfR1 with substantially similar affinity (e.g., having a $K_D$ value in the same order). In some instances, the functional variants may have the same heavy chain CDR3 as the exemplary antibody, and optionally the same light chain CDR3 as the exemplary antibody. Alternatively or in addition, the functional variants may have the same heavy chain CDR2 as the exemplary antibody. Such an anti-TfR1 antibody may comprise a $V_H$ fragment having CDR amino acid residue variations in only the heavy chain CDR1 as compared with the $V_H$ of the exemplary antibody. In some examples, the anti-TfR1 antibody may further comprise a $V_L$ fragment having the same $V_L$ CDR3, and optionally same $V_L$ CDR1 or VL CDR2 as the exemplary antibody.

Alternatively or in addition, the amino acid residue variations can be conservative amino acid residue substitutions.

In some embodiments, the anti-TfR1 antibody may comprise heavy chain CDRs that are at least 80% (e.g., 85%, 90%, 95%, or 98%) sequence identity, individually or collectively, as compared with the $V_H$ CDRs of an exemplary antibody described herein. Alternatively or in addition, the anti-TfR1 antibody may comprise light chain CDRs that are at least 80% (e.g., 85%, 90%, 95%, or 98%) sequence identity, individually or collectively, as compared with the $V_L$ CDRs as an exemplary antibody described herein. As used herein, "individually" means that one CDR of an antibody shares the indicated sequence identity relative to the corresponding CDR of the exemplary antibody. "Collectively" means that three $V_H$ or $V_L$ CDRs of an antiody in combination share the indicated sequence identity relative the corresponding three $V_H$ or $V_L$ CDRs of the exemplary antibody in combination.

In some embodiments, the anti-TfR1 antibody may comprise a VH that is at least 80% (e.g., 85%, 90%, 95%, or 98%) sequence identity as the VH of one of the exemplary antibodies provided in Table 5 (e.g., the VH of Fab0061 or Fab0070). Alternatively or in addition, the anti-TfR1 antibody may comprise a VH that is at least 80% (e.g., 85%, 90%, 95%, or 98%) sequence identity as the VL of one of the exemplary antibodies provided in Table 5 (e.g., the VL of Fab0061 or Fab0070). Such a variant may comprise the same heavy chain and light chain CDRs as the exemplary antibody with variations only in one or more of the FR regions.

In some embodiments, the heavy chain of any of the anti-TfR1 antibodies as described herein may further comprise a heavy chain constant region (CH) or a portion thereof (e.g., CH1, CH2, CH3, or a combination thereof). The heavy chain constant region can of any suitable origin, e.g., human, mouse, rat, or rabbit. Alternatively or in addition, the light chain of the anti-TfRu antibody may further comprise a light chain constant region (CL), which can be any CL known in the art. In some examples, the CL is a kappa light chain. In other examples, the CL is a lambda light chain. Antibody heavy and light chain constant regions are well known in the art, e.g., those provided in the IMGT database (www.imgt.org) or at www.vbase2.org/vbstat.php., both of which are incorporated by reference herein.

In some instances, the anti-TfR1 antibodies are in Fab format, which comprises a heavy chain comprising any of the VH regions disclosed herein and a CH1 fragment and a light chain comprising any of the VL regions disclosed herein and a light chain constant region (LC). The CH1 fragment may be of any immunoglobin (Ig) heavy chain constant region (e.g., a human Ig heavy chain constant region). In some instances, the CH-1 may be of an IgG (e.g., IgG1, IgG2, or IgG4) heavy chain. The LC may be of human original in some instances. It can be a kappa chain. Alternatively, it can be a lambda chain. Examples of the anti-TfR1 Fab antibodies disclosed herein are provided in Table 5.

In some embodiments, the anti-TfR1 antibody disclosed herein may be a single chain antibody (scFv). A scFv antibody may comprise a VH fragment and a VL fragment, which may be linked via a flexible peptide linker. In some instances, the scFv antibody may be in the VH→VL orientation (from N-terminus to C-terminus). In other instances, the scFv antibody may be in the VL→VH orientation (from N-terminus to C-terminus).

Any of the anti-TfR1 antibodies disclosed herein may further comprise an Fc fragment, for example, an Fc fragment from a human immunoglobulin (e.g., a human IgG molecule). In some examples, such an anti-TfR1 antibody may be a Fab-Fc molecule, in which the Fc fragment can be fused with either the VH-CH1 chain or the VL-LC chain. One example of such a Fab-Fc molecule is provided in Table 5.

B. Preparation of Anti-TfR1 Antibodies

Antibodies capable of binding TfR1 as described herein can be made by any method known in the art, for example, via recombinant technology. See, for example, Harlow and Lane, (1998) Antibodies: A Laboratory Manual, Cold Spring Harbor Laboratory, New York.

If desired, an antibody (monoclonal or polyclonal) of interest (e.g., produced by a hybridoma cell line or isolated from an antibody library) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to, e.g., humanize the antibody or to improve the affinity (affinity maturation), or other characteristics of the antibody. For example, the constant region may be engineered to more resemble human constant regions to avoid immune response if the antibody is from a non-human source and is to be used in clinical trials and treatments in humans. Alternatively or in addition, it may be desirable to genetically manipulate the antibody sequence to obtain greater affinity and/or specificity to the target antigen and greater efficacy in enhancing the activity of TfR1. It will be apparent to one of skill in the art that one or more polynucleotide changes can be made to the antibody and still maintain its binding specificity to the target antigen.

Alternatively, antibodies capable of binding to the target antigens as described herein (a TfR1 molecule) may be isolated from a suitable antibody library via routine practice. Antibody libraries can be used to identify proteins that bind to a target antigen (e.g., human TfR1 such as cell surface TfR1) via routine screening processes. In the selection process, the polypeptide component is probed with the target antigen or a fragment thereof and, if the polypeptide component binds to the target, the antibody library member is identified, typically by retention on a support. Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component and purification of the polypeptide component for detailed characterization.

There are a number of routine methods known in the art to identify and isolate antibodies capable of binding to the target antigens described herein, including phage display, yeast display, ribosomal display, or mammalian display technology.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Methods for constructing humanized antibodies are also well known in the art. See, e.g., Queen et al., Proc. Natl. Acad. Sci. USA, 86:10029-1003[3] (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VI-H and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage-display, yeast-display, mammalian cell-display, or mRNA-display scFv library and scFv clones specific to TfR1 can be identified from the library following routine procedures. Positive clones can be subjected to further screening to identify those that enhance CD19 activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence, to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries).

Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of TfR1 have been replaced (swapped) with sequences from a closely related, but antigenically distinct protein (such as another member of the tumor necrosis factor receptor family). By assessing binding of the antibody to the mutant TfR1, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

In some examples, an anti-TfR1 antibody (e.g., in Fab format) is prepared by recombinant technology as exemplified below.

Nucleic acids encoding the heavy and light chain of an anti-TfR1 antibody as described herein can be cloned into one expression vector, each nucleotide sequence being in operable linkage to a suitable promoter. In one example, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, ITLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987); Gossen and Bujard (1992); M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy, 10(16):1392-1399 (2003)). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColEl for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-TfR1 antibody, as also described herein. The recombinant expression vector can be introduced into a suitable host cell (e.g., a dhfr-CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-TfR1 antibody and the other encoding the light chain of the anti-TfR1 antibody. Both of the two recombinant expression vectors can be introduced into a suitable host cell (e.g., dhfr-CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-TfR1 antibody as described herein, vectors (e.g., expression vectors) containing such; and host cells comprising the vectors are within the scope of the present disclosure. Also within the scope of the present disclosure are methods for producing the anti-TfR1 antibodies via expressing such in host cells and harvesting the antibody thus produced from the host cells and/or the culture supernatant.

II. Anti-TfR1 Antibody Conjugates

In some aspects, any of the anti-TfR1 antibodies disclosed herein may be linked to one or more payloads to form anti-TfR1 antibody conjugates. In some embodiments, the anti-TfR1 antibody in any of the conjugates provided herein may be in Fab format. Exemplary anti-TfR1 antibodies (e.g., Fab antibodies) are provided in Table 5 below, any of which can be used to make the conjugates disclosed herein. In some specific examples, the anti-TfR1 antibody is derived from Fab0061 (e.g., Fab0061 or a functional variant thereof). In other specific examples, the anti-TfR1 antibody is derived from Fab0070 (e.g., Fab0070 or a functional variant thereof).

Any of the anti-TfR1 antibody conjugates provided here, e.g., TfR1 Fab-conjugated payload such as interfering RNA, can deliver the payload (e.g., interfering RNA molecules) into the central nervous system (CNS) via the brain endothelial cells of a patient. Without being bound by theory, the conjugates may bind to a transferrin receptor (TfR1) on the surface of a brain endothelial cell. The payload such as the interfering RNA can be attached by any acceptable means for joining the anti-TfR1 antibody (e.g., Fab) to the payload (e.g., the interfering RNA) such that the payload (e.g., the interfering RNA) can be transferred across the cell membrane in a pharmaceutically active form. In some embodiment, the TfR1-specific antibody (e.g., Fab) can be linked to the TfR1-specific antibody using chemical conjugation techniques. In addition to covalent bonding, conjugates can be formed employing non-covalent bonds, such as those formed with bifunctional antibodies, ionic bonds, hydrogen bonds, hydrophobic interactions, etc.

A payload such as an interfering RNA molecule can be covalently linked to a TfR1-specific antibody such as Fab directly. Alternatively, the payload such as the interfering RNA can be linked to the antibody a spacer. In some examples, the spacer may be a glycine spacer (e.g., having 1, 2, 3, or 4 glycines). In some embodiments, the spacer may be a glycine spacer comprises 2 or 3 glycines.

A. Oligonucleotide-Based Agents, Including RNAi Agents

The payload in any of the conjugates may be any types of molecules with a desired bioactivity. In some instances, the payload can be a therapeutic agent. Alternatively, the payload can be a diagnostic agent. In some embodiments, the payload may be an oligonucleotide-based agent.

As used herein, an "oligonucleotide-based agent" is a nucleotide acid containing about 10-50 (e.g., 10 to 48, 10 to 46, 10 to 44, 10 to 42, 10 to 40, 10 to 38, 10 to 36, 10 to 34, 10 to 32, 10 to 30, 10 to 28, 10 to 26, 10 to 24, 10 to 22, 10 to 20, 10 to 18, 10 to 16, 10 to 14, 10 to 12, 12 to 50, 12 to 48, 12 to 46, 12 to 44, 12 to 42, 12 to 40, 12 to 38, 12 to 36, 12 to 34, 12 to 32, 12 to 30, 12 to 28, 12 to 26, 12 to 24, 12 to 22, 12 to 20, 12 to 18, 12 to 16, 12 to 14, 14 to 50, 14 to 48, 14 to 46, 14 to 44, 14 to 42, 14 to 40, 14 to 38, 14 to 36, 14 to 34, 14 to 32, 14 to 30, 14 to 28, 14 to 26, 14 to 24, 14 to 22, 14 to 20, 14 to 18, 14 to 16, 16 to 50, 16 to 48, 16 to 46, 16 to 44, 16 to 42, 16 to 40, 16 to 38, 16 to 36, 16 to 34, 16 to 32, 16 to 30, 16 to 28, 16 to 26, 16 to 24, 16 to 22, 16 to 20, 16 to 18, 18 to 50, 18 to 48, 18 to 46, 18 to 44, 18 to 42, 18 to 40, 18 to 38, 18 to 36, 18 to 34, 18 to 32, 18 to 30, 18 to 28, 18 to 26, 18 to 24, 18 to 22, 18 to 20, 20 to 50, 20 to 48, 20 to 46, 20 to 44, 20 to 42, 20 to 40, 20 to 38, 20 to 36, 20 to 34, 20 to 32, 20 to 30, 20 to 28, 20 to 26, 20 to 24, 20 to 22, 22 to 50, 22 to 48, 22 to 46, 22 to 44, 22 to 42, 22 to 40, 22 to 38, 22 to 36, 22 to 34, 22 to 32, 22 to 30, 22 to 28, 22 to 26, 22 to 24, 24 to 50, 24 to 48, 24 to 46, 24 to 44, 24 to 42, 24 to 40, 24 to 38, 24 to 36, 24 to 34, 24 to 32, 24 to 30, 24 to 28, 24 to 26, 26 to 50, 26 to 48, 26 to 46, 26 to 44, 26 to 42, 26 to 40, 26 to 38, 26 to 36, 26 to 34, 26 to 32, 26 to 30, 26 to 28, 28 to 50, 28 to 48, 28 to 46, 28 to 44, 28 to 42, 28 to 40, 28 to 38, 28 to 36, 28 to 34, 28 to 32, to 28 to 30, 30 to 50, 30 to 48, 30 to 46, 30 to 44, 30 to 42, 30 to 40, 30 to 38, 30 to 36, 30 to 34, 30 to 32, 32 to 50, 32 to 48, 32 to 46, 32 to 44, 32 to 42, 32 to 40, 32 to 38, 32 to 36, 32 to 34, 34 to 50, 34 to 48, 34 to 46, 34 to 44, 34 to 42, 34 to 40, 34 to 38, 34 to 36, 36 to 50, 36 to 48, 36 to 46, 36 to 44, 36 to 42, 36 to 40, 36 to 38, 38 to 50, 38 to 48, 38 to 46, 38 to 44, 38 to 42, 38 to 40, 40 to 50, 40 to 48, 40 to 46, 40 to 44, 40 to 42, 42 to 50, 42 to 48, 42 to 46, 42 to 44, 44 to 50, 44 to 48, 44 to 46, 46 to 50, 46 to 48, or 48 to 50) nucleotides or nucleotide base pairs. In some embodiments, an oligonucleotide-based agent has a nucleobase sequence that is at least partially complementary to a coding sequence in an expressed target nucleic acid or target gene within a cell. In some embodiments, the oligonucleotide-based agents, upon delivery to a cell expressing a target gene, are able to inhibit the expression of the underlying gene, and are referred to herein as "expression-inhibiting oligonucleotide-based agents." The gene expression can be inhibited either in vitro or in vivo.

"Oligonucleotide-based agents" include, but are not limited to, single-stranded oligonucleotides, single-stranded antisense oligonucleotides, short interfering RNAs (siRNAs), double-strand RNAs (dsRNA), micro RNAs (miRNAs), short hairpin RNAs (shRNA), ribozymes, interfering RNA molecules, and dicer substrates. In some embodiments, an oligonucleotide-based agent is a single-stranded oligonucleotide, such as an antisense oligonucleotide (ASO). In some embodiments, an oligonucleotide-based agent is a double-stranded oligonucleotide. In some embodiments, an oligonucleotide-based agent is a double-stranded oligonucleotide that is an RNAi agent.

In some embodiments, the oligonucleotide-based agent can be an "RNAi agent," which as defined herein is a composition that contains an RNA or RNA-like (e.g., chemically modified RNA) oligonucleotide molecule that is capable of degrading or inhibiting translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double-strand RNAs (dsRNA), micro RNAs (miRNAs), short hairpin RNAs (shRNA), and dicer substrates. The antisense strand of the RNAi agents described herein is at least partially complementary to the mRNA being targeted. RNAi agents can include one or more modified nucleotides and/or one or more non-phosphodiester linkages.

Typically, RNAi agents can be comprised of at least a sense strand (also referred to as a passenger strand) that includes a first sequence, and an antisense strand (also referred to as a guide strand) that includes a second sequence. The length of an RNAi agent sense and antisense strands can each be 16 to 49 nucleotides in length. In some embodiments, the sense and antisense strands of an RNAi agent are independently 17 to 26 nucleotides in length. In some embodiments, the sense and antisense strands are independently 19 to 26 nucleotides in length. In some embodiments, the sense and antisense strands are independently 21 to 26 nucleotides in length. In some embodiments, the sense and antisense strands are independently 21 to 24 nucleotides in length. The sense and antisense strands can be either the same length or different lengths. The RNAi agents include an antisense strand sequence that is at least partially complementary to a sequence in the target gene, and upon delivery to a cell expressing the target, an RNAi agent may inhibit the expression of one or more target genes in vivo or in vitro.

It is not necessary for all positions in a given compound to be uniformly modified. Conversely, more than one modification may be incorporated in a single oligonucleotide-based agent or even in a single nucleotide thereof.

The RNAi agent sense strands and antisense strands may be synthesized and/or modified by methods known in the art. Additional disclosures related to RNAi agents may be found, for example, in the disclosure of modifications may be found, for example, in International Patent Application No. PCT/US2017/045446 (WO2018027106) to Arrowhead Pharmaceuticals, Inc., which also is incorporated by reference herein for the subject matter and purpose referenced herein.

B. Modification of Oligonucleotide-Based Agents

Any of the oligonucleotide-based agents such as RNAi agents may contain one or more modifications. Exemplary modifications can include any modification to the sugar, the nucleobase, the internucleoside linkage (e.g., to a linking phosphate/to a phosphodiester linkage/to the phosphodiester backbone), and any combination thereof. Some of the exemplary modifications provided herein are described in detail below.

(a) Modified Nucleotides

In some embodiments, any of the oligonucleotide-based agents provided herein such as RNAi agents, may be comprised of modified nucleotides and/or one or more non-phosphodiester linkages. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides in an oligonucleotide-based agent such as an RNAi agent can be modified nucleotides. As used herein, modified nucleotides include, but are not limited to, deoxyribonucleotides, nucleotide mimics, abasic nucleotides, 2'-modified nucleotides, 3' to 3' linkages (inverted) nucleotides, non-natural base-comprising nucleotides, bridged nucleotides, peptide nucleic acids, 2',3'-seco nucleotide mimics (unlocked nucleobase analogues, locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e. a nucleotide with a group other than a hydroxyl group at the 2' position of the five-membered sugar ring) include, but are not limited to, 2'-O-methyl nucleotides, 2'-deoxy-2'-fluoro nucleotides, 2'-deoxy nucleotides, 2'-methoxyethyl (2'-O-2-methoxylethyl) nucleotides, 2'-amino nucleotides, and 2'-alkyl nucleotides. It is not necessary for all positions in a given compound to be uniformly modified. Conversely, more than one modification can be incorporated in a single target RNAi agent or even in a single nucleotide thereof. The target RNAi agent sense strands and antisense strands can be synthesized and/or modified by methods known in the art. Modification at one nucleotide is independent of modification at another nucleotide.

Moreover, one or more nucleotides of an oligonucleotide-based agent, such as an RNAi agent, may be linked by non-standard linkages or backbones (i.e., modified internucleoside linkages or modified backbones). A modified internucleoside linkage may be a non-phosphate-containing covalent internucleoside linkage. Modified internucleoside linkages or backbones include, but are not limited to, 5'-phosphorothioate groups, chiral phosphorothioates, thiophosphates, phosphorodithioates, phosphotriesters, amino-alkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being unmodified ribonucleotides. As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the sense strand being unmodified ribonucleotides. In some embodiments, one or more nucleotides of an RNAi agent is an unmodified ribonucleotide.

(b) Modified Internucleoside Linkages

In some embodiments, one or more nucleotides of an RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of an RNAi agent can contain 1, 2, 3, 4, 5, or 6 phosphorothioate linkages, an antisense strand of an RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of an RNAi agent can contain 1, 2, 3, or 4 phosphorothioate linkages, an antisense strand of an RNAi agent can contain 1, 2, 3, or 4 phosphorothioate linkages, or both the sense strand and the antisense strand independently can contain 1, 2, 3, or 4 phosphorothioate linkages.

In some embodiments, an RNAi agent sense strand contains at least two phosphorothioate internucleoside linkages. In some embodiments, the at least two phosphorothioate internucleoside linkages are between the nucleotides at positions 1-3 from the 3' end of the sense strand. In some embodiments, one phosphorothioate internucleoside linkage is at the 5' end of the sense strand, and another phosphorothioate linkage is at the 3' end of the sense strand. In some embodiments, two phosphorothioate internucleoside linkage are located at the 5' end of the sense strand, and another phosphorothioate linkage is at the 3' end of the sense strand. In some embodiments, the sense strand does not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, an RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1-4 from the 5' end of the antisense strand, and a fourth phosphorothioate internucleoside linkage is located between positions 20-21 from the 5' end of the antisense strand. In some embodiments, an RNAi agent contains at least three or four phosphorothioate internucleoside linkages in the antisense strand.

In some embodiments, an RNAi agent contains one or more modified nucleotides and one or more modified internucleoside linkages. In some embodiments, a 2'-modified nucleoside is combined with modified internucleoside linkage.

Exemplary modifications of oligonucleotide-based agents such as RNAi agents are provided in Tables 8 and 9 below, each of which is within the scope of the present disclosure.

C. CNS Gene Targets of Oligonucleotide-Based Agent

The oligonucleotide-based agent such as RNAi agents described herein may have targeted complementary antisense sequences to mRNAs that encode the proteins amyloid precursor protein (APP; UniProt: P05067), Ataxin-1, Ataxin-2 (ATXN2; UniProt:Q99700), Ataxin-3 (ATXN3: UniProt: P54252), Ataxin-7, androgen receptor (AR; UniProt:P10275), Superoxide dismutase [Cu—Zn](SOD1; UniProt: P00441), Huntingtin (HTT: UniProt: P42858), Chromosome 9 open reading frame 72 (C90RF72; UniProt: Q96LT7), Leucine-rich repeat serine/threonine-protein kinase 2 (LRRK2; Q5S007), complement C3 (C3; UniProt: P01024), microtubule-associated protein tau (MAPT; UniProt: P10636), alpha-2A adrenergic receptor (ADRA2A; UniProt: P08913), sodium channel protein type 9 subunit alpha (SCN9A; UniProt: Q15858), Apolipoprotein E (APOE; UniProt: P02649), alpha-synuclein (SNCA: UniProt: P37840), probable G-protein coupled receptor 75 (GPR75: UniProt: 095800), and RNA-binding protein FUS (FUS: UniProt: P35637), GFAP, KCNT1, PRNP, MSH3, RAGE, SNC9A, SCN10A, SCN11 A, SORT1, VCP, PIKFYVE, CHMP7, PDE2A, SARM1, NLRP3, GSDME, and DYRK1A. The expression knockdown of these proteins are expected to efficacious in treating or preventing CNS disorders selected from amyotrophic lateral sclerosis (ALS), Alzheimer's disease, Parkinson's disease, Huntington's Disease, dementia, cognitive impairment, frontotemporal dementia, Lewy body disease, cerebral amyloid angiopathy, tauopathies, spinocerebellar ataxia, Alexander's disease, Kennedy's disease, childhood epilepsy, fatal familial insomnia, prion disease, pain, multiple system atrophy, corticobasal degeneration, progressive supranuclear palsy, TDP43 proteinopathies, traumatic brain injury, Down syndrome, neuropathic pain, inherited erythromelalgia, paroxysmal extreme pain disorder, and heritable small fiber neuropathy.

In some embodiments, oligonucleotide-based agents target androgen receptor (AR) mRNAs are selected from as shown in Tables 8 and 9.

The ability of interfering RNA to knock down the levels of endogenous target gene expression in, for example, HeLa cells can be evaluated in vitro as follows. HeLa cells are plated 24 h prior to transfection in standard growth medium (e.g., DMEM supplemented with 10% fetal bovine serum). Transfection is performed using, for example, Dharmafect 1 (Dbarmacon, Lafayette, Colo.) according to the manufacturer's instructions at interfering RNA concentrations ranging from 0.1 nM-100 nM. SiCONTROL™ Non-Targeting siRNA #1 and siCONTROL™ Cyclophilin B siRNA (Dharmacon) are used as negative and positive controls, respectively. Target mRNA levels and cyclophilin B mRNA (PPIB, NM_000942) levels are assessed by qPCR 24 h post-transfection using, for example, a TAQMAN® Gene Expression Assay that preferably overlaps the target site (Applied Biosystems, Foster City, Calif.). The positive control siRNA gives essentially complete knockdown of cyclophilin B mRNA when transfection efficiency is 100%. Therefore, target mRNA knockdown is corrected for transfection efficiency by reference to the cyclophilin B mRNA level in cells transfected with the cyclophilin B siRNA. Target protein levels may be assessed approximately 72 h post-transfection (actual time dependent on protein turnover rate) by western blot, for example. Standard techniques for RNA and/or protein isolation from cultured cells are well known to those skilled in the art. To reduce the chance of non-specific off-target effects, the lowest possible concentration of interfering RNA is used that produces the desired level of knockdown in target gene expression. Cultured human endothelial cells may be used for an evaluation of the ability of interfering RNA to knockdown levels of an endogenous target gene.

D. Preparation of Anti-TfR1 Antibody Conjugates

The anti-TfR1 antibody conjugates provided herein can be prepared by routine technology (e.g., chemical conjugation techniques) or methods disclosed herein (e.g., see Example 6 below). In some instances, the oligonucleotide-based agent such as an RNAi agent may be conjugated to a chemical linker, e.g., L20-p shown in Example 6 via standard amide reaction. The modified oligonucleotide-based agent may be conjugated to an anti-TfR1 antibody (e.g., in Fab format) via routine chemical reactions.

In some embodiments, the anti-TfR1 antibody, before or after conjugating with the oligonucleotide-based agent, may be modified (capped) with a chemical entity, for example, CP-113 or N-ethyl maleimide (see Example 6 below). In some instances, the antibody-oligonucleotide conjugates provided herein may comprise the chemical linker and/or the cap.

III. Pharmaceutical Compositions

Any of the anti-TfR1 antibodies or the anti-TfR1 antibody conjugates may be formulated into pharmaceutical compositions comprising one or more pharmaceutically acceptable carriers. Such pharmaceutical compositions can be used for therapeutic or diagnostic purposes, depending on the payload conjugated to the antibody, for example, for use in the treatment methods disclosed herein.

As used herein, a "pharmaceutical composition" comprises a pharmacologically effective amount of an Active Pharmaceutical Ingredient (API), and optionally one or more pharmaceutically acceptable excipients. Pharmaceutically acceptable excipients (excipients) are substances other than the Active Pharmaceutical ingredient (API, therapeutic product) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

The pharmaceutical compositions described herein can contain other additional components commonly found in pharmaceutical compositions. In some embodiments, the additional component is a pharmaceutically-active material. Pharmaceutically-active materials include, but are not limited to: anti-pruritics, astringents, local anesthetics, or anti-inflammatory agents (e.g., antihistamine, diphenhydramine, etc.), small molecule drug, antibody, antibody fragment, aptamers, and/or vaccines.

The pharmaceutical compositions may also contain preserving agents, solubilizing agents, stabilizing agents, wetting agents, emulsifiers, sweeteners, colorants, odorants, salts for the variation of osmotic pressure, buffers, coating agents, or antioxidants. They may also contain other agents with a known therapeutic benefit.

The pharmaceutical compositions can be administered in a number of ways depending upon whether local or systemic treatment is desired and upon the area to be treated. Administration can be made by any way commonly known in the art, such as, but not limited to, topical (e.g., by a transdermal patch), pulmonary (e.g., by inhalation or insufflation of powders or aerosols, including by nebulizer, intratracheal, intranasal), epidermal, transdermal, oral or parenteral. Parenteral administration includes, but is not limited to, intravenous, intraarterial, subcutaneous, intraperitoneal or intramuscular injection or infusion; subdermal (e.g., via an implanted device), intracranial, intraparenchymal, intrathecal, and intraventricular, administration. In some embodiments, the pharmaceutical compositions described herein are administered by subcutaneous injection. The pharmaceutical compositions may be administered orally, for example in the form of tablets, coated tablets, dragées, hard or soft gelatin capsules, solutions, emulsions or suspensions. Administration can also be carried out rectally, for example using suppositories; locally or percutaneously, for example using ointments, creams, gels, or solutions; or parenterally, for example using injectable solutions.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor® EL (BASF, Parsippany, NJ) or phosphate buffered saline. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of any of the ligands described herein that can be in microcrystalline form, for example, in the form of an aqueous microcrystalline suspension. Liposomal formulations or biodegradable polymer systems can also be used to present any of the ligands described herein for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). As used herein, "pharmacologically effective amount," "therapeutically effective amount," or simply "effective amount" refers to that amount of an the pharmaceutically active agent to produce a pharmacological, therapeutic or preventive result.

Medicaments containing anti-TfR1 antibodies or antibody fragments, conjugated or unconjugated to oligonucleotide-based compounds, are also an object of the present invention, as are processes for the manufacture of such medicaments, which processes comprise bringing one or more anti-TfR1 antibody or antibody fragments disclosed herein, and, if desired, one or more other substances with a known therapeutic benefit, into a pharmaceutically acceptable form.

The described anti-TfR1 antibody and antibody fragments and pharmaceutical compositions comprising anti-TfR1 antibody and antibody fragments disclosed herein may be packaged or included in a kit, container, pack, or dispenser. The described anti-TfR1 antibody and antibody fragments and pharmaceutical compositions comprising the described anti-TfR1 antibody and antibody fragments may be packaged in pre-filled syringes or vials.

The pharmaceutical composition provided herein may encompass more than one TfR1 antibody (e.g., Fab) conjugated to the same oligonucleotide-based agent (e.g., interfering RNA), for example, a cocktail of different antibodies such as Fabs reactive with the TfR1, or more than one oligonucleotide-based agent such as interfering RNA targeting different locations on a single mRNA.

Pharmaceutical compositions are formulations that comprise interfering RNAs, or antibody conjugate thereof up to 99% by weight mixed with a physiologically acceptable carrier medium, including for example, water, buffer, saline, glycine, hyaluronic acid, mannitol, and the like. The pH of the formulation is about pH 4.0 to about pH 9.0, or about pH 4.5 to about pH 7.4. Methods for preparing nanoparticles and their use in delivering pharmaceutical agents have been described in U.S. Pat. No. 6,632,671, the disclosures of which are incorporated by reference in their entirety. Methods for preparing nanoparticle-Fab conjugates and their use in delivering pharmaceutical agents have been described in U.S. Pat. No. 6,372,250, the disclosures of which are incorporated by reference in their entirety.

IV. Methods of Treatment

In some aspects, the present disclosure provides a method of attenuating expression of a target mRNA in the CNS of a patient, comprising (a) providing an anti-TfR1 antibody (e.g., Fab)-conjugated oligonucleotide-based agent such as interfering RNA; and (b) administering the anti-TfR1 antibody conjugate to the CNS of the patient, wherein the oligonucleotide-based agent such as the interfering RNA molecule attenuates expression of the target mRNA in the CNS.

In certain embodiments, the present disclosure provides a method of preventing or treating a CNS disorder in a patient, the method comprising administering to the patient an anti-TfRu antibody conjugate (e.g., comprising anti-TfR1 Fab conjugated to an interfering RNA). The antibody moiety binds to a TfR1 and transports the oligonucleotide-based agent such as interfering RNA into the CNS via the brain endothelial cells of the patient.

Exemplary CNS disorders are selected from amyotrophic lateral sclerosis (ALS), Alzheimer's disease, Parkinson's disease, Huntington's Disease, dementia, cognitive impairment, frontotemporal dementia, Lewy body disease, cerebral amyloid angiopathy, and tauopathy. CNS brain regions for systemic targeting may include cerebellum, cortex, striatum, tuberous sclerosis complex TCS), or thoracic spinal cord.

In certain embodiments, a patient has a CNS disorder associated with endothelial cells, astrocytes, pericytes, microglia, neurons, or oligodendrocytes cells, or another cell type of the CNS.

The methods of the present disclosure are useful for attenuating expression of particular genes in the CNS of patients using RNA interference. In certain embodiments, a TfR1-specific Fab-interfering RNA conjugate comprises an interfering RNA molecule that targets a gene associated with a CNS disorder. Examples of mRNA target genes for which interfering RNAs of the present invention are designed to target include genes associated with CNS disorders.

In certain embodiments, the method of treating a CNS disease involves targeting a specific cell type in the CNS. In some embodiments, the TfR1 Fab-interfering RNA conjugate or TfR1 Fab-conjugated nanoparticles are delivered to the CNS via brain endothelial cells.

Animal models are used to test the activity of systemically delivered interfering RNA molecules. The Examples of the present application demonstrate successful and effective in vivo delivery of interfering RNA molecules to the CNS. For example, targeted RNA interference can be tested in mice as described in Alvarez-Erviti L, Seow Y, Yin H, Betts C, Lakhal S, Wood M J. Delivery of siRNA to the mouse brain by systemic injection of targeted exosomes. *Nat Biotechnol.* 2011 April; 29(4):341-5. doi: 10.1038/nbt.1807. Epub 2011 Mar. 20. PMID: 21423189.

In other embodiments, the method of delivering an interfering RNA molecule comprises administering to the patient an antibody-conjugated to a nanoparticle, wherein the interfering RNA molecule is encapsulated in the nanoparticle and the nanoparticle is linked to a TfR1 antibody, which transports the antisense oligonucleotide molecule into the CNS of the patient via brain endothelial cell transport. Other embodiments of the invention provide a method of preventing or treating a CNS disorder, said method comprising delivering an antisense oligonucleotide molecule to the CNS of a patient via brain endothelial cells using a Fab-conjugated nanoparticle.

The TfR1 antibody (e.g., Fab)-conjugated oligonucleotide-based agent (e.g., interfering RNA) and nanoparticles comprising such can be administered by intravenous injection, oral administration, intramuscular injection, intranasal, intraperitoneal injection, intrathecal injection, inhalation, transdermal application, sublingual, or transmucosal application. The form and concentration in which the TfR1 antibody (e.g., Fab)-conjugated oligonucleotide-based agent (e.g., interfering RNA) and nanoparticles comprising such is administered (e.g., capsule, tablet, solution, emulsion) will depend at least in part on the route by which it is administered.

In certain embodiments, treatment of CNS disorders with interfering RNA molecules is accomplished by administration of a TfR1 antibody (e.g., Fab)-conjugated oligonucleotide-based agent (e.g., interfering RNA) and nanoparticles comprising such encompassing interfering RNA composition directly to the CNS. Therapeutic treatment of patients with interfering RNAs directed against target mRNAs is expected to be beneficial over small molecule treatments by increasing the duration of action, thereby allowing less frequent dosing and greater patient compliance, and by increasing target specificity, thereby reducing side effects.

A therapeutically effective amount of a formulation may depend on factors such as the age, race, and sex of the patient, the severity of the disorder, the rate of target gene transcript/protein turnover, the antibody (e.g., Fab) affinity, the number of oligonucleotide-based agent (e.g., interfering RNA molecules) per antibody (e.g., Fab), the oligonucleotide-based agent (e.g., interfering RNA) potency, and the oligonucleotide-based agent (e.g., interfering RNA) stability, for example. In one embodiment, the interfering RNA is delivered at a therapeutic dose thereby ameliorating target gene-associated disease processes.

In certain embodiments, the invention provides a specific pharmaceutical composition for preventing or treating a CNS disorder in a patient, comprising an interfering RNA-TfR1 Fab conjugate or nanoparticle-TfR1 Fab conjugate of the invention in an acceptable carrier for the CNS and in a therapeutically effective amount. A therapeutically effective amount of the interfering RNAs used in a composition of the invention results in an extracellular concentration at the surface of the target cell of from about 100 pM to 1 μM, or from about 1 nM to 100 nM, or from about 5 nM to about 50 nM, or to about 25 nM. The dose required to achieve this local concentration will vary depending on a number of factors including the delivery method, the site of delivery, the number of cell layers between the delivery site and the target cell or tissue, whether delivery is local via intracranial or systemic, among other factors. For example, compositions can be delivered to the CNS via intravenous injection bi-weekly, monthly, or longer, according to the discretion of a skilled clinician. Interfering RNA-TfR11 Fab conjugates and nanoparticle-TfR1 Fab conjugates of the present invention are administered as solutions, suspensions, or emulsions The TfR1 Fab-conjugated interfering RNA may be delivered in solution, in suspension, or in bioerodible or non-bioerodible delivery devices.

V. Kits

In certain embodiments, the present disclosure also provides a kit that includes reagents for attenuating the expression of an mRNA as cited herein in a cell. The kit contains an oligonucleotide-based agent-antibody conjugate (e.g., an interfering RNA-Fab conjugate) and/or the necessary components for interfering RNA-Fab conjugate production (e.g., an interfering RNA molecule as well as the Fab and necessary materials for linking). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an TfR1 antibody-conjugated interfering RNA composition. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds.(1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Humanization of the TfR1 Fab

Human consensus sequences of heavy chain subgroup III (humIII) and light chain k subgroup I (humkI) (Carter P, Presta et al Proc. Natl. Acad. Sci. USA 89, 4285-4289 (1992); Presta L G, et al J. Immunol 151, 2623-2632 (1993); Kabat, E. A., et al Sequences of Proteins of Immunological Interest. 5th ed. Public Health Service, National Institutes of Health, Bethesda, Md. (1991)) was used for the humanization of the anti-hTfR1 antibodies. To generate a template pAY2 for a future CDR swap, the humIII and humkI genes were inserted into a phagemid designed to display human Fab on the surface of M13 bacteriophage. Two open reading frames were used to encode for two peptide chains separately under the control of phoA promoters. The first open reading frame encoded for the light chain and second one encoded for the heavy chain fused to the C-terminal domain of the M13 minor coat protein P3. Both peptide chains were directed for secretion by N-terminal stII signal sequences.

Single Stranded DNA (ssDNA) Template of pAY2 pAY2 was then transformed into chemical competent CJ236 cells (uracil deglycosidase deficient) with a micropulser electroporator (Bio-Rad). Single colony was used to inoculate 1 ml 2YT starting culture with 100 μg/ml ampicillin and 10 μg/ml chloramphenicol and the resulting culture was shaken at 37° C. for 6 h. M13KO7 helper phage (~$10^{10}$ pfu) was added and after 10 min shaking at 37° C., 300 ml of the mixture was transferred to 30 ml 2YT with 100 μg/ml ampicillin and 0.25 μg/ml uridine. After 18 h growth at 37° C., phages were purified and the uracil-containing ssDNA was isolated with the E.Z.N.A.® M13 DNA Mini Kit (Omega Biotek Inc).

Example 2. Incorporating 6 CDRs into a humIII for VH and humkI for VL to Generate the Humanized hmab1a Kunkel mutagenesis (Kunkel T. A. Proc Natl Acad Sci USA 82, 488-92 (1985); Sidhu S. S et al Methods Enzymol 328, 333-63 (2000)) was employed to construct the CDR swap version of the humanized anti hTfR1 antibody hmab1a. Six primers were designed to swap the six CDRs of mab0039 antibody into pAY2. The primers were phosphorylated individually using T4 Polynucleotide kinase (NEB) at 37° C. for 1 h then annealed to the uracil-containing ssDNA template at 90° C. for 1 min, 50° C. for 3 min and placed on ice. The oligonucleotides were extended with T7 DNA polymerase and ligated with T4 DNA ligase at 37° C. for 1.5 h to form covalently closed circular DNA. The DNA was desalted and affinity purified with Qiagen QIAquick DNA purification kit and transformed into XL-1 blue cells (uracil glycosidase containing strain) by heat shock transformation. Small scale DNA was purified using Qiagen miniprep kit and sent for sequencing to confirm the sequence. Plasmid hmab1a was then used to prepare uracil-containing ssDNA for humanization library construction.

Humanization Library (Lib AY1 Construction

Based on the published work (Baca M, et al J. Biol. Chem. 272, 10678-10684 (1997)) and other therapeutic antibody sequence, the library was designed to include the mouse and frequent human amino acid compositions at the following sites, VL: M4 (MTG), F71 (TWC); VH: A24 (RYC), V37 (RTC), F67 (NYC), 169 (HTT), R71 (SKT), D73 (RAW), K75 (ARM), N76 (ARC), L78 (KYG), A93 (DYG), R94 (ARG). Degenerate codons used for each site are shown in the parentheses. M=A or C, W=A or T, R=A or G, Y=C or T, N=A, C, G, or T, H=A, C, or T, K=G or T, S=G or C, and D=A, G, or T. Two primers in VL and three primers in VH were designed to introduce these degenerate codons in the desired sites via Kunkel mutagenesis. Phosphorylation of the primers and Kunkel mutagenesis were carried out as described (Sidhu S. S et al Methods Enzymol 328, 333-63 (2000)). Covalently closed circular DNA obtained was electroporated into electrocompetent SS320 cells to prepare hmab1 humanization Fab library as described (Sidhu S. S et al Methods Enzymol 328, 333-63 (2000)). The titered apparent diversity was 6.9×108, larger than 4.7×106, the designed theoretical diversity.

Selection of the Humanized Hmab1 Clones

Selection was carried out similar to what has been described previously (Ye J. D., et al Proc Natl Acad Sci USA 105, 82-87 (2008)). Biotinylated ECD domain of hTfR1 (hTfR1-B) was used as the antigen. In the first round, 0.5 nmol of hTfR1-B was immobilized on magnetic beads (Promega) and incubated with 1012-13 cfu of phages for 15 min in 1 ml of PT (1×PBS with 0.05% Tween 20), supplemented with 0.5% BSA and 0.2 mg/ml streptavidin. The solution was then removed, and the beads were washed twice with PT and amplified for later rounds of selection. In the subsequent rounds, purified phage pools were first incubated with streptavidin beads for 15 min, and the supernatant was used in the subsequent selection on a KingFisher magnetic particle processor (Thermo Fisher). Phages (1010-11 cfu) were incubated for 15 min with decreasing concentrations of hTfR1-B (20-0.1 nM). Streptavidin magnetic beads were then added to the solution for 15 min to allow the capture of hTfR1-B together with the bound phages. The beads were washed five times with PT, and resuspended in 100 μl PT. After each round of selection, recovered phages were amplified as described (Sidhu S. S et al Methods Enzymol 328, 333-63 (2000)).

Phage ELISA Screening with Low Antigen Concentration (PESLA)

After four rounds of selection, individual clones were analyzed by phage ELISA (Ye J. D., et al Proc Natl Acad Sci USA 105, 82-87 (2008)). The procedure was modified to screen high affinity binders in a high throughput manner. Ninety-six or more individual colonies were picked from a fresh LB/Amp plate, inoculated in 300 μL of 2YT medium containing 100 g/mL ampicillin and 1010 PFU/mL M13KO7 helper phage in a 96-well deep-well plate, and grown at 37° C. overnight with shaking at 300 rpm. The deep-well plate was then centrifuged for 15 min at 3500 rpm and 4° C. to pellet the cells. The supernatant was diluted 3-fold with phage dilution buffer (PBS, 0.5% BSA, and 0.05% Tween 20) to prepare a phage solution. A 96-well Maxisorp plate was coated with 100 μL of 0.1-0.2 g/mL hTfR1 in 100 mM sodium bicarbonate coating buffer (pH 9.6) overnight at 4° C. The coating solution was removed and the Maxisorp plate was blocked for 1 h with 200 μL/well of 1% (w/v) BSA in PBS. After the blocking solution was removed, the Maxisorp plate was washed 4 times with PBS with 0.05% (v/v) Tween 20 (PT) and incubated with 100 μL/well of phage solution for 1 h at room temperature. After washing with PT Buffer 6 times, the Maxisorp plate was incubated with 100 μL/well anti-M13/horseradish peroxidase conjugate (diluted 3000× in phage dilution buffer) at room temperature for 30 min. After washing 6 times with PT Buffer, the Maxisorp plate was incubated with 100 μL/well Ultra TMB-ELISA Substrates for 5-10 min, quenched with 100 μL/well of 1 M phosphoric acid, and read spectrophotometrically at 450 nm in a microplate reader. As the low antigen concentration serves as the limiting factor, higher signals correlate with the tighter binding clones. These tighter binders were miniprepped and sequenced to identify unique clones.

Characterization of the Unique Clones with Competitive Phage ELISA

Twenty-four unique clones were identified from Library AY1. Competitive phage ELISA was used to characterize the binding affinities of these clones. MaxiSorp ELISA plate was coated with hTfR1 overnight at 4° C. and blocked with BSA for 1 hr at RT. Serial dilutions of hTfR1 were incubated with subsaturating concentrations of phage at RT for 1 hr, and then added to the blocked and washed ELISA plate. After 15 min incubation and washing, anti-M13 antibody/HRP conjugate was added and incubated for 30 min, then developed with TMB for 5-10 min and quenched with 1 M phosphoric acid. Binding signal was analyzed by the plate reader. Mab1G showed best binding affinity (0.78 nM) toward hTfR1

Example 3. General Method for Affinity Maturation of mab1G

Construction of the mab1G Affinity Maturation Library (Lib AY2)

Uracil containing single stranded DNA template of mab1G was generated with a procedure similar to that described in Sidhu S. S et al Methods Enzymol 328, 333-63 (2000). In this library, all six CDRs were screened at the same time. A single amino acid CDR walking strategy (Yang W. P., et al J. Mol. Biol. 254, 392-403 (1995)) was adopted. The randomized positions included 24-25 and 27-34 in CDR-L1, 50-56 in CDR-L2, 90-97 in CDR-L3, 27-35 in CDR-H1, 50 and 52-58 in CDR-H2, and 95-102 in CDR-L3. Each position was randomized individually at a given CDR with the degenerate codon NNS to encode all 20 amino acids. Randomization was incorporated into mab1G ssDNA template via Kunkel mutagenesis (Kunkel T. A. Proc Natl Acad Sci USA 82, 488-92 (1985); Sidhu S. S et al Methods Enzymol 328, 333-63 (2000)). Phosphorylation of the primers and Kunkel mutagenesis were carried out as described (Sidhu S. S et al Methods Enzymol 328, 333-63 (2000)). Covalently closed circular DNA obtained was electroporated into electrocompetent SS320 cells to prepare Lib AY2 as described (Sidhu S. S et al Methods Enzymol 328, 333-63 (2000)). The titered apparent diversity was 1.1×1010.

Selection of the Affinity Maturated Antibodies

Selection was carried out similar to what has been described previously (Ye J. D., et al *Proc Natl Acad Sci USA* 105, 82-87 (2008)). Biotinylated ECD domain of hTfR1 (hTfR1-B) was used as the antigen. In each round except for the first round, purified phage pools were first incubated with streptavidin beads for 15 min, and the supernatant was used in the subsequent selection on a KingFisher magnetic particle processor (Thermo Fisher). Phages ($10^{10-11}$ cfu) were incubated for 15 min-1 hr with hTfR1-B (20, 0.3, 0.05, and 0.05 nM for round 1-4, respectively). Streptavidin magnetic beads were then added to the solution for 1.5-15 min to allow the capture of the hTfR1-B together with the bound phages. In the third round, a separate selection was carried out in addition to the regular selection. After the capture of the antigen/antibody complex on the beads, the beads were washed with PBS supplemented with 0.05% Tween 20 (PT) and >1000 fold of competitive non-biotinylated hTfR1 was incubated with the beads for 2.5 hours at RT. The beads were then washed five times with PT, and resuspended in 100 µl PT. After each round of selection, recovered phages were amplified as described (Sidhu S. S et al *Methods Enzymol* 328, 333-63 (2000)).

Example 4. Combining Beneficial Mutations from Different CDRs

PESLA was applied to the third round output (without hTfR1 competition) and the fourth round output (with hTfR1 competition in the third round). Unique mutations were identified through sequencing. These mutations were combined with two different approaches. In method one, individual clones were prepared with combined mutations through Kunkel mutagenesis. In the second method, a mini library was generated by combining all the identified mutations and selected against hTfR1-B. Together these methods yielded 15 Fab clones (Fab0060-Fab0074)S Tables 1-2 show the CDR1 and CDR2 variants from VL and VH with the combined beneficial mutations of Fabs 0060-0074. The CDR3 is the same sequence in the 15 Fab clones VL (QHFWGTPLT; SEQ ID NO: 13 and V: GTRAYHY; SEQ ID NO: 24).

TABLE 1

| Light Chain Complementarity Determining Regions (CDRs) | | | |
|---|---|---|---|
| Clone Name | LC CDR1 | LC CDR2 | LC CDR3 |
| Fab0060 | RASDGLYSNLA (SEQ ID NO: 2) | DATKLAS (SEQ ID NO: 7) | QHFWGTPLT (SEQ ID NO: 13) |
| Fab0061 | RASDGLYSNLA (SEQ ID NO: 2) | DATKLAS (SEQ ID NO: 7) | QHFWGTPLT (SEQ ID NO: 13) |
| Fab0062 | RASDGLYSNLA (SEQ ID NO: 2) | DAFNLAS (SEQ ID NO: 8) | QHFWGTPLT (SEQ ID NO: 13) |
| Fab0063 | RASDGLYSNLA (SEQ ID NO: 2) | DATRLAS (SEQ ID NO: 9) | QHFWGTPLT (SEQ ID NO: 13) |
| Fab0064 | RASDGLYSNLA (SEQ ID NO: 2) | DAKNLAS (SEQ ID NO: 10) | QHFWGTPLT (SEQ ID NO: 13) |
| Fab0065 | RASDNLYRNLA (SEQ ID NO: 3) | DATKLAS (SEQ ID NO: 7) | QHFWGTPLT (SEQ ID NO: 13) |
| Fab0066 | RASDGLYSNLA (SEQ ID NO: 2) | DAFNLAS (SEQ ID NO: 8) | QHFWGTPLT (SEQ ID NO: 13) |
| Fab0067 | RASDNLYRNLA (SEQ ID NO: 3) | DATKLAS (SEQ ID NO: 7) | QHFWGTPLT (SEQ ID NO: 13) |
| Fab0068 | RASDGLYSNLA (SEQ ID NO: 2) | DATKLAS (SEQ ID NO: 7) | QHFWGTPLT (SEQ ID NO: 13) |
| Fab0069 | RASDGLYSNLA (SEQ ID NO: 2) | DATKLAS (SEQ ID NO: 7) | QHFWGTPLT (SEQ ID NO: 13) |
| Fab0070 | RASDKLYSNLA (SEQ ID NO: 4) | DATLLAS (SEQ ID NO: 11) | QHFWGTPLT (SEQ ID NO: 13) |
| Fab0071 | RASDGLYSNLA (SEQ ID NO: 2) | DARNLAS (SEQ ID NO: 12) | QHFWGTPLT (SEQ ID NO: 13) |
| Fab0072 | RASDNLYRNLA (SEQ ID NO: 3) | DARNLAS (SEQ ID NO: 12) | QHFWGTPLT (SEQ ID NO: 13) |
| Fab0073 | RASDNLYRNLA (SEQ ID NO: 3) | DATKLAS (SEQ ID NO: 7) | QHFWGTPLT (SEQ ID NO: 13) |
| Fab0074 | RASDGLYSNLA (SEQ ID NO: 2) | DAKNLAS (SEQ ID NO: 10) | QHFWGTPLT (SEQ ID NO: 13) |
| Fab0165 | RASDKLYSNLA (SEQ ID NO: 4) | DATLLAS (SEQ ID NO: 11) | QHFWGTPLT (SEQ ID NO: 13) |
| Fab0166 | RASDKLYSNLA (SEQ ID NO: 4) | DATLLAS (SEQ ID NO: 11) | QHFWGTPLT (SEQ ID NO: 13) |
| Fab0167 | RASDKLYSNLA (SEQ ID NO: 4) | DATLLAS (SEQ ID NO: 11) | QHFWGTPLT (SEQ ID NO: 13) |
| Fab0168 | RASDKLYSNLA (SEQ ID NO: 4) | DATLLAS (SEQ ID NO: 11) | QHFWGTPLT (SEQ ID NO: 13) |

TABLE 1-continued

Light Chain Complementarity Determining Regions (CDRs)

| Clone Name | LC CDR1 | LC CDR2 | LC CDR3 |
|---|---|---|---|
| xAb000293 | RASDKLYSNLA (SEQ ID NO: 4) | DATLLAS (SEQ ID NO: 11) | QHFWGTPLT (SEQ ID NO: 13) |
| Consensus Motifs | RASDX$_5$LYX$_6$NLA (SEQ ID NO: 5), in which X$_5$ is G, K, or N, and X$_6$ is R or S | DAX$_7$X$_8$LAS, in which X$_7$ is F, K, R, or T; and X$_8$ is K, L, N, or R | QHFWGTPLT (SEQ ID NO: 13) |

TABLE 2

Heavy Chain Complementarity Determining Regions (CDRs)

| Clone Name | HC CDR1 | HC CDR2 | HC CDR3 |
|---|---|---|---|
| Fab0060 | GYTFTSYWVH (SEQ ID NO: 15) | EINPTNGRTNYIEKFKS (SEQ ID NO: 19) | GTRAYHY (SEQ ID NO: 24) |
| Fab0061 | GYTFTSYWMH (SEQ ID NO: 14) | EINPTNGRVNYIEKFKS (SEQ ID NO: 20) | GTRAYHY (SEQ ID NO: 24) |
| Fab0062 | GYTFTSYWMH (SEQ ID NO: 14) | EINPTNGRVNYIEKFKS (SEQ ID NO: 20) | GTRAYHY (SEQ ID NO: 24) |
| Fab0063 | GYTFTSYWMH (SEQ ID NO: 14) | EINPTNGRVNYIEKFKS (SEQ ID NO: 20) | GTRAYHY (SEQ ID NO: 24) |
| Fab0064 | GYTFTSYWMH (SEQ ID NO: 14) | EINPTNGRVNYIEKFKS (SEQ ID NO: 20) | GTRAYHY (SEQ ID NO: 24) |
| Fab0065 | GYTFTSYWVH (SEQ ID NO: 15) | EINPTNGRSNYIEKFKS (SEQ ID NO: 21) | GTRAYHY (SEQ ID NO: 24) |
| Fab0066 | GYTFTSYWVH (SEQ ID NO: 15) | EINPTNGRVNYIEKFKS (SEQ ID NO: 20) | GTRAYHY (SEQ ID NO: 24) |
| Fab0067 | GYTFTSYWVH (SEQ ID NO: 15) | EINPTNGRTNYIEKFKS (SEQ ID NO: 19) | GTRAYHY (SEQ ID NO: 24) |
| Fab0068 | GYTFTSYWVH (SEQ ID NO: 15) | EINPTNGRVNYIEKFKS (SEQ ID NO: 20) | GTRAYHY (SEQ ID NO: 24) |
| Fab0069 | GYTFTSYWVH (SEQ ID NO: 15) | EINPTNGRSNYIEKFKS (SEQ ID NO: 21) | GTRAYHY (SEQ ID NO: 24) |
| Fab0070 | GFTFTSYWMH (SEQ ID NO: 16) | EINPTNGRTNYIEKFKS (SEQ ID NO: 19) | GTRAYHY (SEQ ID NO: 24) |
| Fab0071 | GYTFNSYWMH (SEQ ID NO: 17) | EINPTNGRTNYIEKFKS (SEQ ID NO: 19) | GTRAYHY (SEQ ID NO: 24) |
| Fab0072 | GYTFNSYWMH (SEQ ID NO: 17) | EINPTNGRFNYIEKFKS (SEQ ID NO: 22) | GTRAYHY (SEQ ID NO: 24) |
| Fab0073 | GYTFKSYWMH (SEQ ID NO: 18) | EINPTNGRTNYIEKFKS (SEQ ID NO: 19) | GTRAYHY (SEQ ID NO: 24) |
| Fab0074 | GYTFKSYWMH (SEQ ID NO: 18) | EINPTNGRTNYIEKFKS (SEQ ID NO: 19) | GTRAYHY (SEQ ID NO: 24) |
| Fab0165 | GFTFTSYWMH (SEQ ID NO: 16) | EINPTNGRTNYIEKFKS (SEQ ID NO: 19) | GTRAYHY (SEQ ID NO: 24) |
| Fab0166 | GFTFTSYWMH (SEQ ID NO: 16) | EINPTNGRTNYIEKFKS (SEQ ID NO: 19) | GTRAYHY (SEQ ID NO: 24) |
| Fab0167 | GFTFTSYWMH (SEQ ID NO: 16) | EINPTNGRTNYIEKFKS (SEQ ID NO: 19) | GTRAYHY (SEQ ID NO: 24) |
| Fab0168 | GFTFTSYWMH (SEQ ID NO: 16) | EINPTNGRTNYIEKFKS (SEQ ID NO: 19) | GTRAYHY (SEQ ID NO: 24) |

TABLE 2-continued

| Heavy Chain Complementarity Determining Regions (CDRs) | | | |
|---|---|---|---|
| Clone Name | HC CDR1 | HC CDR2 | HC CDR3 |
| xAb000293 | GFTFTSYWMH (SEQ ID NO: 16) | EINPTNGRTNYIEKFKS (SEQ ID NO: 19) | GTRAYHY (SEQ ID NO: 24) |
| Consensus Motifs | $GX_1TFX_2SYWX_3H$, in which $X_1$ is F or Y; $X_2$ is K, N, or T, and $X_3$ is M or V | $EINPTNGRX_4NYIEKFKS$ (SEQ ID NO: 23), in which $X_4$ is F, S, T, or V | GTRAYHY (SEQ ID NO: 24) |

Table 3 shows exemplary light chain framework regions used in the exemplary anti-TfR1 antibodies provided herein. An exemplary CH1 sequence for use in the Fab light chain is also provided in Table 3.

TABLE 3

| Exemplary Light Chain Framework Regions and Constant Region | | | |
|---|---|---|---|
| LC FR1 | LC FR2 | LC FR3 | LC FR4 |
| DIQLTQSPSSLSAS VGDRVTITC (SEQ ID NO: 25) | WYQQKPGKAPKLLIY (SEQ ID NO: 26) | GVPSRFSGSGSGTDYTL TISSLQPEDFATYYC (SEQ ID NO: 27) | FGQGTKVEIK (SEQ ID NO: 28) |
| CL | | | |
| RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC (SEQ ID NO: 29) | | | |

Table 4 shows exemplary heavy chain framework regions used in the exemplary anti-TfR1 antibodies provided herein. An exemplary CH1 sequence for use in the Fab heavy chain is also provided in Table 4.

TABLE 4

| Exemplary Heavy Chain Framework Regions and Constant Region Fragment | | | |
|---|---|---|---|
| HC FR1 | HC FR2 | HC FR3 | HC FR4 |
| EVQLVESGGGLV QPGGSLRLSCATS (SEQ ID NO: 30) | WVRQAPGKGLEWVA (SEQ ID NO: 31) | RITLSVDKSKSTVYLQ MNSLRAEDTAVYYCA R (SEQ ID NO: 32) | WGQGTLVTVSS (SEQ ID NO: 33) |
| CH1 | | | |
| ASTKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKRVEPKSCDKTH (SEQ ID NO: 34) | | | |

Table 5 below lists VH and VL sequences of exemplary anti-TfR1 antibodies provided herein and their heavy and light chain sequences when in Fab format.

TABLE 5

| Sequences of Exemplary Anti-TfR1 Fab Antibodies | | | |
|---|---|---|---|
| Clone Name | | Amino Acid Sequences | SEQ ID NO |
| Fab0060 | VH | EVQLVESGGGLVQPGGSLRLSCATSGYTFTSYWVHWVRQ APGKGLEWVAEINPTNGRTNYIEKFKSRITLSVDKSKSTVY LQMNSLRAEDTAVYYCARGTRAYHYWGQGTLVTVSS | 39 |
| | VL | DIQLTQSPSSLSASVGDRVTITCRASDGLYSNLAWYQQKPG KAPKLLIYDATKLASGVPSRFSGSGSGTDYTLTISSLQPEDF ATYYCQHFWGTPLTFGQGTKVEIK | 40 |
| | VH-CH1 | EVQLVESGGGLVQPGGSLRLSCATSGYTFTSYWVHWVRQ APGKGLEWVAEINPTNGRTNYIEKFKSRITLSVDKSKSTVY | 41 |

TABLE 5-continued

Sequences of Exemplary Anti-TfR1 Fab Antibodies

| Clone Name | | Amino Acid Sequences | SEQ ID NO |
|---|---|---|---|
| | | LQMNSLRAEDTAVYYCARGTRAYHYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTH | |
| | VL-CL | DIQLTQSPSSLSASVGDRVTITCRASDGLYSNLAWYQQKPG KAPKLLIYDATKLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC | 42 |
| Fab0061 | VH | EVQLVESGGGLVQPGGSLRLSCATSGYTFTSYWMHWVRQ APGKGLEWVAEINPTNGRVNYIEKFKSRITLSVDKSKSTVY LQMNSLRAEDTAVYYCARGTRAYHYWGQGTLVTVSS | 43 |
| | VL | DIQLTQSPSSLSASVGDRVTITCRASDGLYSNLAWYQQKPG KAPKLLIYDATKLASGVPSRFSGSGSGTDYTLTISSLQPEDF ATYYCQHFWGTPLTFGQGTKVEIK | 44 |
| | VH-CH1 | EVQLVESGGGLVQPGGSLRLSCATSGYTFTSYWMHWVRQ APGKGLEWVAEINPTNGRVNYIEKFKSRITLSVDKSKSTVY LQMNSLRAEDTAVYYCARGTRAYHYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTH | 45 |
| | VL-CL | DIQLTQSPSSLSASVGDRVTITCRASDGLYSNLAWYQQKPG KAPKLLIYDATKLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC | 46 |
| Fab0062 | VH | EVQLVESGGGLVQPGGSLRLSCATSGYTFTSYWMHWVRQ APGKGLEWVAEINPTNGRVNYIEKFKSRITLSVDKSKSTVY LQMNSLRAEDTAVYYCARGTRAYHYWGQGTLVTVSS | 43 |
| | VL | DIQLTQSPSSLSASVGDRVTITCRASDGLYSNLAWYQQKPG KAPKLLIYDAFNLASGVPSRFSGSGSGTDYTLTISSLQPEDF ATYYCQHFWGTPLTFGQGTKVEIK | 47 |
| | VH-CH1 | EVQLVESGGGLVQPGGSLRLSCATSGYTFTSYWMHWVRQ APGKGLEWVAEINPTNGRVNYIEKFKSRITLSVDKSKSTVY LQMNSLRAEDTAVYYCARGTRAYHYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTH | 45 |
| | VL-CL | DIQLTQSPSSLSASVGDRVTITCRASDGLYSNLAWYQQKPG KAPKLLIYDAFNLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC | 48 |
| Fab0063 | VH | EVQLVESGGGLVQPGGSLRLSCATSGYTFTSYWMHWVRQ APGKGLEWVAEINPTNGRVNYIEKFKSRITLSVDKSKSTVY LQMNSLRAEDTAVYYCARGTRAYHYWGQGTLVTVSS | 43 |
| | VL | DIQLTQSPSSLSASVGDRVTITCRASDGLYSNLAWYQQKPG KAPKLLIYDATRLASGVPSRFSGSGSGTDYTLTISSLQPEDF ATYYCQHFWGTPLTFGQGTKVEIK | 49 |
| | VH-CH1 | EVQLVESGGGLVQPGGSLRLSCATSGYTFTSYWMHWVRQ APGKGLEWVAEINPTNGRVNYIEKFKSRITLSVDKSKSTVY LQMNSLRAEDTAVYYCARGTRAYHYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTH | 45 |
| | VL-CL | DIQLTQSPSSLSASVGDRVTITCRASDGLYSNLAWYQQKPG KAPKLLIYDATRLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC | 50 |
| Fab0064 | VH | EVQLVESGGGLVQPGGSLRLSCATSGYTFTSYWMHWVRQ APGKGLEWVAEINPTNGRVNYIEKFKSRITLSVDKSKSTVY LQMNSLRAEDTAVYYCARGTRAYHYWGQGTLVTVSS | 43 |
| | VL | DIQLTQSPSSLSASVGDRVTITCRASDGLYSNLAWYQQKPG KAPKLLIYDAKNLASGVPSRFSGSGSGTDYTLTISSLQPEDF ATYYCQHFWGTPLTFGQGTKVEIK | 51 |

TABLE 5-continued

Sequences of Exemplary Anti-TfR1 Fab Antibodies

| Clone Name | | Amino Acid Sequences | SEQ ID NO |
|---|---|---|---|
| | VH-CH1 | EVQLVESGGGLVQPGGSLRLSCATSGYTFTSYWMHWVRQ APGKGLEWVAEINPTNGRVNYIEKFKSRITLSVDKSKSTVY LQMNSLRAEDTAVYYCARGTRAYHYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTH | 45 |
| | VL-CL | DIQLTQSPSSLSASVGDRVTITCRASDGLYSNLAWYQQKPG KAPKLLIYDAKNLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC | 52 |
| Fab0065 | VH | EVQLVESGGGLVQPGGSLRLSCATSGYTFTSYWVHWVRQ APGKGLEWVAEINPTNGRSNYIEKFKSRITLSVDKSKSTVY LQMNSLRAEDTAVYYCARGTRAYHYWGQGTLVTVSS | 53 |
| | VL | DIQLTQSPSSLSASVGDRVTITCRASDNLYRNLAWYQQKPG KAPKLLIYDATKLASGVPSRFSGSGSGTDYTLTISSLQPEDF ATYYCQHFWGTPLTFGQGTKVEIK | 54 |
| | VH-CH1 | EVQLVESGGGLVQPGGSLRLSCATSGYTFTSYWVHWVRQ APGKGLEWVAEINPTNGRSNYIEKFKSRITLSVDKSKSTVY LQMNSLRAEDTAVYYCARGTRAYHYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTH | 55 |
| | VL-CL | DIQLTQSPSSLSASVGDRVTITCRASDNLYRNLAWYQQKPG KAPKLLIYDATKLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC | 56 |
| Fab0066 | VH | EVQLVESGGGLVQPGGSLRLSCATSGYTFTSYWVHWVRQ APGKGLEWVAEINPTNGRVNYIEKFKSRITLSVDKSKSTVY LQMNSLRAEDTAVYYCARGTRAYHYWGQGTLVTVSS | 57 |
| | VL | DIQLTQSPSSLSASVGDRVTITCRASDGLYSNLAWYQQKPG KAPKLLIYDAFNLASGVPSRFSGSGSGTDYTLTISSLQPEDF ATYYCQHFWGTPLTFGQGTKVEIK | 47 |
| | VH-CH1 | EVQLVESGGGLVQPGGSLRLSCATSGYTFTSYWVHWVRQ APGKGLEWVAEINPTNGRVNYIEKFKSRITLSVDKSKSTVY LQMNSLRAEDTAVYYCARGTRAYHYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTH | 58 |
| | VL-CL | DIQLTQSPSSLSASVGDRVTITCRASDGLYSNLAWYQQKPG KAPKLLIYDAFNLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC | 48 |
| Fab0067 | VH | EVQLVESGGGLVQPGGSLRLSCATSGYTFTSYWVHWVRQ APGKGLEWVAEINPTNGRTNYIEKFKSRITLSVDKSKSTVY LQMNSLRAEDTAVYYCARGTRAYHYWGQGTLVTVSS | 39 |
| | VL | DIQLTQSPSSLSASVGDRVTITCRASDNLYRNLAWYQQKPG KAPKLLIYDATKLASGVPSRFSGSGSGTDYTLTISSLQPEDF ATYYCQHFWGTPLTFGQGTKVEIK | 54 |
| | VH-CH1 | EVQLVESGGGLVQPGGSLRLSCATSGYTFTSYWVHWVRQ APGKGLEWVAEINPTNGRTNYIEKFKSRITLSVDKSKSTVY LQMNSLRAEDTAVYYCARGTRAYHYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTH | 41 |
| | VL-CL | DIQLTQSPSSLSASVGDRVTITCRASDNLYRNLAWYQQKPG KAPKLLIYDATKLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC | 56 |
| Fab0068 | VH | EVQLVESGGGLVQPGGSLRLSCATSGYTFTSYWVHWVRQ APGKGLEWVAEINPTNGRVNYIEKFKSRITLSVDKSKSTVY LQMNSLRAEDTAVYYCARGTRAYHYWGQGTLVTVSS | 57 |

TABLE 5-continued

Sequences of Exemplary Anti-TfR1 Fab Antibodies

| Clone Name | | Amino Acid Sequences | SEQ ID NO |
|---|---|---|---|
| | VL | DIQLTQSPSSLSASVGDRVTITCRASDGLYSNLAWYQQKPG<br>KAPKLLIYDATKLASGVPSRFSGSGSGTDYTLTISSLQPEDF<br>ATYYCQHFWGTPLTFGQGTKVEIK | 44 |
| | VH-CH1 | EVQLVESGGGLVQPGGSLRLSCATSGYTFTSYWVHWVRQ<br>APGKGLEWVAEINPTNGRVNYIEKFKSRITLSVDKSKSTVY<br>LQMNSLRAEDTAVYYCARGTRAYHYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKRVEPKSCDKTH | 58 |
| | VL-CL | DIQLTQSPSSLSASVGDRVTITCRASDGLYSNLAWYQQKPG<br>KAPKLLIYDATKLASGVPSRFSGSGSGTDYTLTISSLQPEDF<br>ATYYCQHFWGTPLTFGQGTKVEIKRTVAAPSVFIFPPSDEQ<br>LKSGTASVVCLLNNFYPREAKVQWKVDNALQSGNSQESV<br>TEQDSKDSTYSLSSTLTLSKADYEKHKVYACEVTHQGLSSP<br>VTKSFNRGEC | 46 |
| Fab0069 | VH | EVQLVESGGGLVQPGGSLRLSCATSGYTFTSYWVHWVRQ<br>APGKGLEWVAEINPTNGRSNYIEKFKSRITLSVDKSKSTVY<br>LQMNSLRAEDTAVYYCARGTRAYHYWGQGTLVTVSS | 53 |
| | VL | DIQLTQSPSSLSASVGDRVTITCRASDGLYSNLAWYQQKPG<br>KAPKLLIYDATKLASGVPSRFSGSGSGTDYTLTISSLQPEDF<br>ATYYCQHFWGTPLTFGQGTKVEIK | 44 |
| | VH-CH1 | EVQLVESGGGLVQPGGSLRLSCATSGYTFTSYWVHWVRQ<br>APGKGLEWVAEINPTNGRSNYIEKFKSRITLSVDKSKSTVY<br>LQMNSLRAEDTAVYYCARGTRAYHYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKRVEPKSCDKTH | 55 |
| | VL-CL | DIQLTQSPSSLSASVGDRVTITCRASDGLYSNLAWYQQKPG<br>KAPKLLIYDATKLASGVPSRFSGSGSGTDYTLTISSLQPEDF<br>ATYYCQHFWGTPLTFGQGTKVEIKRTVAAPSVFIFPPSDEQ<br>LKSGTASVVCLLNNFYPREAKVQWKVDNALQSGNSQESV<br>TEQDSKDSTYSLSSTLTLSKADYEKHKVYACEVTHQGLSSP<br>VTKSFNRGEC | 46 |
| Fab0070 | VH | EVQLVESGGGLVQPGGSLRLSCATSGFTFTSYWMHWVRQ<br>APGKGLEWVAEINPTNGRTNYIEKFKSRITLSVDKSKSTVY<br>LQMNSLRAEDTAVYYCARGTRAYHYWGQGTLVTVSS | 59 |
| | VL | DIQLTQSPSSLSASVGDRVTITCRASDKLYSNLAWYQQKPG<br>KAPKLLIYDATLLASGVPSRFSGSGSGTDYTLTISSLQPEDF<br>ATYYCQHFWGTPLTFGQGTKVEIK | 60 |
| | VH-CH1 | EVQLVESGGGLVQPGGSLRLSCATSGFTFTSYWMHWVRQ<br>APGKGLEWVAEINPTNGRTNYIEKFKSRITLSVDKSKSTVY<br>LQMNSLRAEDTAVYYCARGTRAYHYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKRVEPKSCDKTH | 61 |
| | VL-CL | DIQLTQSPSSLSASVGDRVTITCRASDKLYSNLAWYQQKPG<br>KAPKLLIYDATLLASGVPSRFSGSGSGTDYTLTISSLQPEDF<br>ATYYCQHFWGTPLTFGQGTKVEIKRTVAAPSVFIFPPSDEQ<br>LKSGTASVVCLLNNFYPREAKVQWKVDNALQSGNSQESV<br>TEQDSKDSTYSLSSTLTLSKADYEKHKVYACEVTHQGLSSP<br>VTKSFNRGEC | 62 |
| Fab0071 | VH | EVQLVESGGGLVQPGGSLRLSCATSGYTFNSYWMHWVRQ<br>APGKGLEWVAEINPTNGRTNYIEKFKSRITLSVDKSKSTVY<br>LQMNSLRAEDTAVYYCARGTRAYHYWGQGTLVTVSS | 63 |
| | VL | DIQLTQSPSSLSASVGDRVTITCRASDGLYSNLAWYQQKPG<br>KAPKLLIYDARNLASGVPSRFSGSGSGTDYTLTISSLQPEDF<br>ATYYCQHFWGTPLTFGQGTKVEIK | 64 |
| | VH-CH1 | EVQLVESGGGLVQPGGSLRLSCATSGYTFNSYWMHWVRQ<br>APGKGLEWVAEINPTNGRTNYIEKFKSRITLSVDKSKSTVY<br>LQMNSLRAEDTAVYYCARGTRAYHYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKRVEPKSCDKTH | 65 |
| | VL-CL | DIQLTQSPSSLSASVGDRVTITCRASDGLYSNLAWYQQKPG<br>KAPKLLIYDARNLASGVPSRFSGSGSGTDYTLTISSLQPEDF<br>ATYYCQHFWGTPLTFGQGTKVEIKRTVAAPSVFIFPPSDEQ<br>LKSGTASVVCLLNNFYPREAKVQWKVDNALQSGNSQESV<br>TEQDSKDSTYSLSSTLTLSKADYEKHKVYACEVTHQGLSSP<br>VTKSFNRGEC | 66 |

TABLE 5-continued

Sequences of Exemplary Anti-TfR1 Fab Antibodies

| Clone Name | | Amino Acid Sequences | SEQ ID NO |
|---|---|---|---|
| Fab0072 | VH | EVQLVESGGGLVQPGGSLRLSCATSGYTFNSYWMHWVRQAPGKGLEWVAEINPTNGRFNYIEKFKSRITLSVDKSKSTVYLQMNSLRAEDTAVYYCARGTRAYHYWGQGTLVTVSS | 67 |
| | VL | DIQLTQSPSSLSASVGDRVTITCRASDNLYRNLAWYQQKPGKAPKLLIYDARNLASGVPSRFSGSGSGTDYTLTISSLQPEDFATYYCQHFWGTPLTFGQGTKVEIK | 68 |
| | VH-CH1 | EVQLVESGGGLVQPGGSLRLSCATSGYTFNSYWMHWVRQAPGKGLEWVAEINPTNGRFNYIEKFKSRITLSVDKSKSTVYLQMNSLRAEDTAVYYCARGTRAYHYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTH | 69 |
| | VL-CL | DIQLTQSPSSLSASVGDRVTITCRASDNLYRNLAWYQQKPGKAPKLLIYDARNLASGVPSRFSGSGSGTDYTLTISSLQPEDFATYYCQHFWGTPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 70 |
| Fab0073 | VH | EVQLVESGGGLVQPGGSLRLSCATSGYTFKSYWMHWVRQAPGKGLEWVAEINPTNGRTNYIEKFKSRITLSVDKSKSTVYLQMNSLRAEDTAVYYCARGTRAYHYWGQGTLVTVSS | 71 |
| | VL | DIQLTQSPSSLSASVGDRVTITCRASDNLYRNLAWYQQKPGKAPKLLIYDATKLASGVPSRFSGSGSGTDYTLTISSLQPEDFATYYCQHFWGTPLTFGQGTKVEIK | 54 |
| | VH-CH1 | EVQLVESGGGLVQPGGSLRLSCATSGYTFKSYWMHWVRQAPGKGLEWVAEINPTNGRTNYIEKFKSRITLSVDKSKSTVYLQMNSLRAEDTAVYYCARGTRAYHYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTH | 72 |
| | VL-CL | DIQLTQSPSSLSASVGDRVTITCRASDNLYRNLAWYQQKPGKAPKLLIYDATKLASGVPSRFSGSGSGTDYTLTISSLQPEDFATYYCQHFWGTPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 56 |
| Fab0074 | VH | EVQLVESGGGLVQPGGSLRLSCATSGYTFKSYWMHWVRQAPGKGLEWVAEINPTNGRTNYIEKFKSRITLSVDKSKSTVYLQMNSLRAEDTAVYYCARGTRAYHYWGQGTLVTVSS | 71 |
| | VL | DIQLTQSPSSLSASVGDRVTITCRASDGLYSNLAWYQQKPGKAPKLLIYDAKNLASGVPSRFSGSGSGTDYTLTISSLQPEDFATYYCQHFWGTPLTFGQGTKVEIK | 51 |
| | VH-CH1 | EVQLVESGGGLVQPGGSLRLSCATSGYTFKSYWMHWVRQAPGKGLEWVAEINPTNGRTNYIEKFKSRITLSVDKSKSTVYLQMNSLRAEDTAVYYCARGTRAYHYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTH | 72 |
| | VL-CL | DIQLTQSPSSLSASVGDRVTITCRASDGLYSNLAWYQQKPGKAPKLLIYDAKNLASGVPSRFSGSGSGTDYTLTISSLQPEDFATYYCQHFWGTPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 52 |
| Fab0165 | VH | EVQLVESGGGLVQPGGSLRLSCATSGFTFTSYWMHWVRQAPGKGLEWVAEINPTNGRTNYIEKFKSRITLSVDKSKSTVYLQMNSLRAEDTAVYYCARGTRAYHYWGQGTLVTVSS | 59 |
| | VL | DIQLTQSPSSLSASVGDRVTITCRASDKLYSNLAWYQQKPGKAPKLLIYDATLLASGVPSRFSGSGSGTDYTLTISSLQPEDFATYYCQHFWGTPLTFGQGTKVEIK | 60 |
| | VH-CH1 | EVQLVESGGGLVQPGGSLRLSCATSGFTFTSYWMHWVRQAPGKGLEWVAEINPTNGRTNYIEKFKSRITLSVDKSKSTVYLQMNSLRAEDTAVYYCARGTRAYHYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTH | 61 |
| | VL-CL | DIQLTQSPSSLSASVGDRVTITCRASDKLYSNLAWYQQKPGKAPKLLIYDATLLASGVPSRFSGSGSGTDYTLTISSLQPEDFATYYCQHFWGTPLTFGQGTKVEIKRTVAAPSVFIFPPSDEQLKSGTASVVCLLNNFYPREAKVQWCVDNALQSGNSQESVTEQDSKDSTYSLSSTLTLSKADYEKHKVYACEVTHQGLSSPVTKSFNRGEC | 73 |

TABLE 5-continued

Sequences of Exemplary Anti-TfR1 Fab Antibodies

| Clone Name | | Amino Acid Sequences | SEQ ID NO |
|---|---|---|---|
| Fab0166 | VH | EVQLVESGGGLVQPGGSLRLSCATSGFTFTSYWMHWVRQ APGKGLEWVAEINPTNGRTNYIEKFKSRITLSVDKSKSTVY LQMNSLRAEDTAVYYCARGTRAYHYWGQGTLVTVSS | 59 |
| | VL | DIQLTQSPSSLSASVGDRVTITCRASDKLYSNLAWYQQKPG KAPKLLIYDATLLASGVPSRFSGSGSGTDYTLTISSLQPEDF ATYYCQHFWGTPLTFGQGTKVEIK | 60 |
| | VH-CH1 | EVQLVESGGGLVQPGGSLRLSCATSGFTFTSYWMHWVRQ APGKGLEWVAEINPTNGRTNYIEKFKSRITLSVDKSKSTVY LQMNSLRAEDTAVYYCARGTRAYHYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTH | 61 |
| | VL-CL | DIQLTQSPSSLSASVGDRVTITCRASDKLYSNLAWYQQKPG KAPKLLIYDATLLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP CTKSFNRGEC | 74 |
| Fab0167 | VH | EVQLVESGGGLVQPGGSLRLSCATSGFTFTSYWMHWVRQ APGKGLEWVAEINPTNGRTNYIEKFKSRITLSVDKSKSTVY LQMNSLRAEDTAVYYCARGTRAYHYWGQGTLVTVSS | 59 |
| | VL | DIQLTQSPSSLSASVGDRVTITCRASDKLYSNLAWYQQKPG KAPKLLIYDATLLASGVPSRFSGSGSGTDYTLTISSLQPEDF ATYYCQHFWGTPLTFGQGTKVEIK | 60 |
| | VH-CH1 | EVQLVESGGGLVQPGGSLRLSCATSGFTFTSYWMHWVRQ APGKGLEWVAEINPTNGRTNYIEKFKSRITLSVDKSKSTVY LQMNSLRAEDTAVYYCARGTRAYHYWGQGTLVTVSSAST KGPSVFPLAPSSKSTSGGTCALGCLVKDYFPEPVTVSWNSG ALTSGVHTFPAVLQSSGLYSLSSVVTVPSSSLGTQTYICNVN HKPSNTKVDKRVEPKSCDKTH | 75 |
| | VL-CL | DIQLTQSPSSLSASVGDRVTITCRASDKLYSNLAWYQQKPG KAPKLLIYDATLLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC | 62 |
| Fab0168 | VH | EVQLVESGGGLVQPGGSLRLSCATSGFTFTSYWMHWVRQ APGKGLEWVAEINPTNGRTNYIEKFKSRITLSVDKSKSTVY LQMNSLRAEDTAVYYCARGTRAYHYWGQGTLVTVSS | 59 |
| | VL | DIQLTQSPSSLSASVGDRVTITCRASDKLYSNLAWYQQKPG KAPKLLIYDATLLASGVPSRFSGSGSGTDYTLTISSLQPEDF ATYYCQHFWGTPLTFGQGTKVEIK | 60 |
| | VH-CH1 | EVQLVESGGGLVQPGGSLRLSCATSGFTFTSYWMHWVRQ APGKGLEWVAEINPTNGRTNYIEKFKSRITLSVDKSKSTVY LQMNSLRAEDTAVYYCARGTRAYHYWGQGTLVTVSSCST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTH | 76 |
| | VL-CL | DIQLTQSPSSLSASVGDRVTITCRASDKLYSNLAWYQQKPG KAPKLLIYDATLLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC | 62 |
| xAb000293 (Fab-Fc) | VH | EVQLVESGGGLVQPGGSLRLSCATSGFTFTSYWMHWVRQ APGKGLEWVAEINPTNGRTNYIEKFKSRITLSVDKSKSTVY LQMNSLRAEDTAVYYCARGTRAYHYWGQGTLVTVSS | 59 |
| | VL | DIQLTQSPSSLSASVGDRVTITCRASDKLYSNLAWYQQKPG KAPKLLIYDATLLASGVPSRFSGSGSGTDYTLTISSLQPEDF ATYYCQHFWGTPLTFGQGTKVEIK | 60 |
| | VH-CH1-Fc | EVQLVESGGGLVQPGGSLRLSCATSGFTFTSYWMHWVRQ APGKGLEWVAEINPTNGRTNYIEKFKSRITLSVDKSKSTVY LQMNSLRAEDTAVYYCARGTRAYHYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFP PKPKDTLYITREPEVTCVVVDVSHEDPEVKFNWYVDGVEV HNAKTKPREEQYNSTYRVVSVLTVLHQDWLNGKEYKCKV SNKALGAPIEKTISKAKGQPREPQVYTLPPCREEMTKNQVS | 77 |

TABLE 5-continued

Sequences of Exemplary Anti-TfR1 Fab Antibodies

| Clone Name | Amino Acid Sequences | SEQ ID NO |
|---|---|---|
| | LWCLVKGFYPSDIA VEWESNGQPENNYKTTPPVLDSDGSF FLYSKLTVDKSRWQQGNVFSCSVMHEALHNHYTQKSLSLS PGK | |
| VL-CL | DIQLTQSPSSLSASVGDRVTITCRASDKLYSNLAWYQQKPG KAPKLLIYDATLLASGVPSRFSGSGSGTDYTLTISSLQPEDF ATYYCQHFWGTPLTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP CTKSFNRGEC | 74 |
| Fc | DKTHTCPPCPAPEAAGGPSVFLFPPKPKDTLYITREPEVTCV VVDVSHEDPEVKFNWYVDGVEVHNAKTKPREEQYNSTYR VVSVLTVLHQDWLNGKEYKCKVSNKALGAPIEKTISKAKG QPREPQVCTLPPSREEMTKNQVSLSCAVKGFYPSDIAVEWE SNGQPENNYKTTPPVLDSDGSFFLVSKLTVDKSRWQQGNV FSCSVMHEALHNHYTQKSLSLSPGK | 78 |

Example 5. Affinity Binding Parameters of TfR1 Antibodies by Competition Binding Assays cTfR1 BLI Kinetics Samples were analyzed via Bio-Layer Interferometry (BLI) to determine kinetics against *cynomolgus* monkey transferrin receptor 1 (cTfR1). Briefly, an Octet RH16 (Sartorius) was used for BLI measurements using streptavidin biosensors (Sartorius p/n 18-5019) to irreversibly immobilize biotinylated cTfR1 (Acro Bio p/n TFR-C8249). Samples were serial diluted to between 150-5 nM depending on expected affinity, and five concentrations within this range are used for analysis. Sample diluent was prepared in house and is composed of 10 mM PBS pH 7.4 (150 mM NaCl), 0.01% BSA, 0.002% Tween 20, and 0.01% kathon. A 96-well plate was used for analysis, filled with required samples solutions and a row of 10 μg/mL cTfR1 for loading of the streptavidin sensors. For each sample, one well was reserved for a reference sensor control (non-specific binding evaluation with no cTfR1 on surface in highest sample concentration) and a sample reference (buffer only on a cTfR1 loaded sample). One well was also reserved for a second replicate of one of the five concentrations to evaluate sensor and method variability. Eight channels were used for the highest sensitivity offered by the Octet RH16. For each assay performed, the steps were as follows: a sensor check for baseline evaluation of sensor alone in buffer was performed for 30 seconds, followed by loading of the cTfR1 for 60 seconds, then a baseline check for 90 seconds to verify stability of cTfR1 immobilized to sensor surface, then sample association for 180 seconds, and finally sample dissociation for 300 seconds. A shake speed of 1000 was used for all steps. Sample results were analyzed in Octet Analysis software.

hTfR1 BLI Kinetics

Samples were analyzed via Bio-Layer Interferometry (BLI) to determine kinetics against human transferrin receptor 1 (hTfR1). Briefly, an Octet RH16 (Sartorius) was used for BLI measurements using streptavidin biosensors (Sartorius p/n 18-5019) to irreversibly immobilize biotinylated hTfR1 (Acro Bio p/n TFR-H82E5). Samples were serial diluted to between 150-5 nM depending on expected affinity, and five concentrations within this range are used for analysis. Sample diluent was prepared in house and is composed of 10 mM PBS pH 7.4 (150 mM NaCl), 0.01% BSA, 0.002% Tween 20, and 0.01% kathon. A 96-well plate was used for analysis, filled with required samples solutions and a row of 10 μg/mL hTfR1 for loading of the streptavidin sensors. For each sample, one well was reserved for a reference sensor control (non-specific binding evaluation with no hTfR1 on surface in highest sample concentration) and a sample reference (buffer only on a hTfR1 loaded sample). One well was also reserved for a second replicate of one of the five concentrations to evaluate sensor and method variability. Eight channels were used for the highest sensitivity offered by the Octet RH16. For each assay performed, the steps were as follows: a sensor check for baseline evaluation of sensor alone in buffer was performed for 30 seconds, followed by loading of the cTfR1 for 60 seconds, then a baseline check for 90 seconds to verify stability of cTfR1 immobilized to sensor surface, then sample association for 180 seconds, and finally sample dissociation for 300 seconds. A shake speed of 1000 was used for all steps. Sample results are analyzed in Octet Analysis software.

cTfR1 SPR Kinetics

Samples were analyzed via Surface Plasmon Resonance (SPR) to determine kinetics against *cynomolgus* monkey transferrin receptor 1 (cTfR1). Briefly, a Biacore X100 (Cytiva) was used for SPR measurements using a CM5 chip (carboxymethylated dextran surface, Cytiva p/n BR100399) with anti-histidine antibody irreversibly immobilized on the surface of both flow cells for the reversible capture of his-tagged cTfR1 (Acro Biosystems p/n TFR-C524a). The anti-histidine antibody was irreversibly immobilized via amine coupling using Cytiva provided Amine Coupling Kit (p/n BR100050) and His Capture Kit (p/n 28995056). Samples were serial diluted to between 150-5 nM depending on expected affinity, and five concentrations within this range were used for analysis. Sample diluent was prepared in house and is composed of 10 mM HEPES buffer pH 7.4, 150 mM NaCl, 3 mM EDTA, and 0.05% Tween 20. Cytiva caps and vials compatible for Biacore X100 were used for sample analysis. Each analysis cycle consists of a capture step followed by sample or blank injection, and finally a regeneration step that removes any sample and cTfR1 on the sensor surface. The capture step was performed at 5 μL/min with a contact time of 24 seconds over the active flow cell only, followed by a fluidics wash with 0.1% Tween 20. Generally, 2 μg/mL hTfR1 was a sufficient concentration to observe adequate hTfR1 captured consistently between cycles. Sample or buffer was injected at 30 μL/min with a contact time of 180 seconds and dissociation time of 180 seconds followed by a fluidics wash with 0.1% Tween 20. A 10 mM glycine solution at pH 1.5 (provided in His Capture Kit) was used for regeneration at 30 μL/min with a 60 second contact time. A cycle was performed for each sample concentration analyzed along with one cycle repeating one concentration for variability evaluation and 2-3 buffer cycles. Results were analyzed in Biacore Evaluation Software. Buffer cycles were averaged and subtracted from sample injections prior to kinetic fitting. A monovalent or kinetic fit was specified as relevant for the sample analyzed. Accuracy of the fit is evaluated and data points are excluded as applicable.

hTfR1 SPR Kinetics

Figure 4:
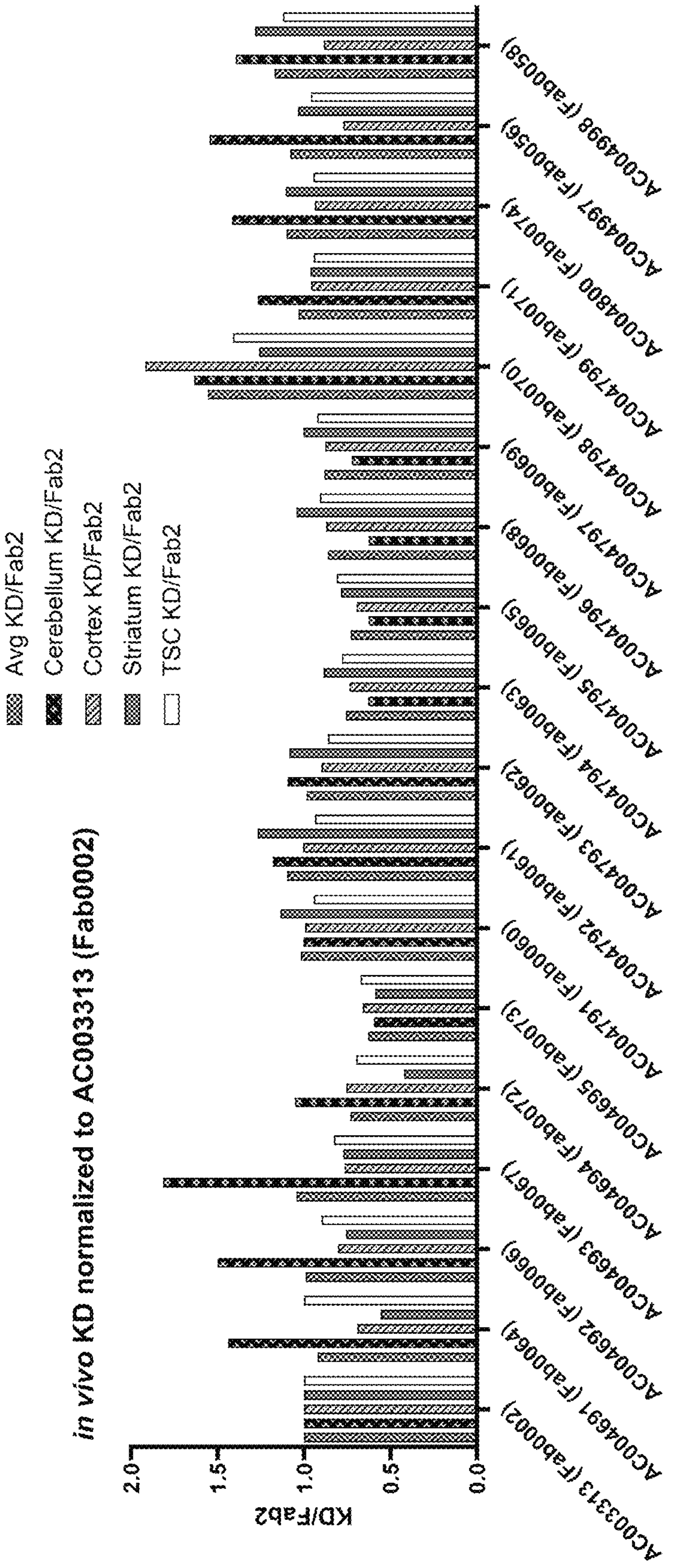
FIG. 4 shows binding affinities of select TfR1-targeting Fabs in $K_D$ normalized to Fab0002.

Samples were analyzed via Surface Plasmon Resonance (SPR) to determine kinetics against human transferrin receptor 1 (hTfR1). Briefly, a Biacore X100 (Cytiva) was used for SPR measurements using a CM5 chip (carboxymethylated dextran surface, Cytiva p/n BR100399) with anti-histidine antibody irreversibly immobilized on the surface of both flow cells for the reversible capture of his-tagged hTfR1 (Acro Biosystems p/n CD1-H5243). The anti-histidine antibody was irreversibly immobilized via amine coupling using Cytiva provided Amine Coupling Kit (p/n BR100050) and His Capture Kit (p/n 28995056). Samples were serial diluted to between 150-5 nM depending on expected affinity, and five concentrations within this range were used for analysis. Sample diluent was prepared in house and is composed of 10 mM HEPES buffer pH 7.4, 150 mM NaCl, 3 mM EDTA, and 0.05% Tween 20. Cytiva caps and vials compatible for Biacore X100 are used for sample analysis. Each analysis cycle consists of a capture step followed by sample or blank injection, and finally a regeneration step that removes any sample and hTfR1 on the sensor surface. The capture step was performed at 5 μL/min with a contact time of 24 seconds over the active flow cell only, followed by a fluidics wash with 0.1% Tween 20. Generally, 2 μg/mL hTfR1 is a sufficient concentration to observe adequate hTfR1 captured consistently between cycles. Sample or buffer was injected at 30 μL/min with a contact time of 180 seconds and a dissociation time of 180 seconds followed by a fluidics wash with 0.1% Tween 20. A 10 mM glycine solution at pH 1.5 (provided in His Capture Kit) was used for regeneration at 30 μL/min with a 60 second contact time. A cycle was performed for each sample concentration analyzed along with one cycle repeating one concentration for variability evaluation and 2-3 buffer cycles. Results were analyzed in Biacore Evaluation Software. Buffer cycles were averaged and subtracted from sample injections prior to kinetic fitting. A monovalent or kinetic fit was specified as relevant for the sample analyzed. Accuracy of the fit was evaluated and data points are excluded as applicable. FIG. 4 shows binding affinities of select TfR1 Fabs in KdD normalized to Fab0002. Fab0002 has the structure shown below:

| | | | |
|---|---|---|---|
| Fab0002 | VH | EVQLVQSGAEVKKPGASVKVSCKASGYTFTSYWMHWV<br>RQAPGQRLEWIGEINPTNGRTNYIEKFKSRATLTVDKSA<br>STAYMELSSLRSEDTAVYYCARGTRAYHYWGQGTMVT<br>VSS | 35 |
| | VL | DIQMTQSPSSLSASVGDRVTITCRASDNLYSNLAWYQQ<br>KPGKSPKLLVYDATNLADGVPSRFSGSGSGTDYTLTISS<br>LQPEDFATYYCQHFWGTPLTFGQGTKVEIK | 36 |
| | VH-CH1 | EVQLVQSGAEVKKPGASVKVSCKASGYTFTSYWMHWV<br>RQAPGQRLEWIGEINPTNGRTNYIEKFKSRATLTVDKSA<br>STAYMELSSLRSEDTAVYYCARGTRAYHYWGQGTMVT<br>VSSASTKGPSVFPLAPSSKSTSGGTAALGCLVKDYFPEPV<br>TVSWNSGALTSGVHTFPAVLQSSGLYSLSSVVTVPSSSL<br>GTQTYICNVNHKPSNTKVDKRVEPKSCDKTH | 37 |
| | VL-CL | DIQMTQSPSSLSASVGDRVTITCRASDNLYSNLAWYQQ<br>KPGKSPKLLVYDATNLADGVPSRFSGSGSGTDYTLTISS<br>LQPEDFATYYCQHFWGTPLTFGQGTKVEIKRTVAAPSVF<br>IFPPSDEQLKSGTASVVCLLNNFYPREAKVQWKVDNAL<br>QSGNSQESVTEQDSKDSTYSLSSTLTLSKADYEKHKVYA<br>CEVTHQGLSSPVTKSFNRGEC | 38 |

Tables 6 and 7 show the binding parameters as measured by competition ELISA, SPR, and BLI with the siRNA conjugate.

TABLE 6

Human Transferrin Receptor 1 (hTfR1) Binding Parameters as Measured by Competition ELISA, SPR, and BLI

| Fab ID | hTfR1 Phage ELISA Kd, nM | hTfR1 Fab ELISA Kd, nM | hTfR1 SPR ka (1/Ms) | hTfR1 SPR kd (1/s) | hTfR1 SPR Kd, nM | hTfR1 BLI conjugate ka (1/Ms) | hTfR1 BLI conjugate kd (1/s) | hTfR1 BLI conjugate Kd, nM |
|---|---|---|---|---|---|---|---|---|
| Fab0002 | 2.8 | 7.28 | 6.492E+05 | 4.988E−03 | 7.683 | 2.091E+05 | 3.487E−03 | 16.680 |
| Fab0060 | 0.49 | 0.81 | 1.221E+06 | 1.107E−03 | 0.907 | 2.980E+05 | 1.088E−03 | 3.650 |
| Fab0061 | 0.49 | 0.95 | 1.423E+06 | 1.008E−03 | 0.708 | 2.782E+05 | 5.272E−04 | 1.895 |
| Fab0062 | 0.65 | 1.1 | 1.182E+06 | 1.174E−03 | 0.993 | 2.751E+05 | 1.230E−03 | 4.472 |
| Fab0063 | 0.48 | 0.67 | 1.749E+06 | 1.047E−03 | 0.598 | 2.853E+05 | 7.750E−04 | 2.717 |
| Fab0064 | 0.34 | 0.67 | 1.468E+06 | 1.107E−03 | 0.754 | 2.726E+05 | 3.926E−04 | 1.440 |

TABLE 6-continued

Human Transferrin Receptor 1 (hTfR1) Binding Parameters as Measured by Competition ELISA, SPR, and BLI

| Fab ID | hTfR1 Phage ELISA Kd, nM | hTfR1 Fab ELISA Kd, nM | hTfR1 SPR ka (1/Ms) | hTfR1 SPR kd (1/s) | hTfR1 SPR Kd, nM | hTfR1 BLI conjugate ka (1/Ms) | hTfR1 BLI conjugate kd (1/s) | hTfR1 BLI conjugate Kd, nM |
|---|---|---|---|---|---|---|---|---|
| Fab0065 | 0.26 | 0.33 | 1.719E+06 | 7.101E−04 | 0.413 | 3.104E+05 | 8.196E−04 | 2.640 |
| Fab0066 | 0.87 | 0.91 | 9.848E+05 | 1.388E−03 | 1.410 | 2.591E+05 | 4.690E−04 | 1.810 |
| Fab0067 | 0.35 | 0.52 | 1.479E+06 | 8.036E−04 | 0.543 | 2.677E+05 | 1.668E−04 | 0.623 |
| Fab0068 | 0.43 | 0.84 | 1.167E+06 | 1.132E−03 | 0.970 | 2.561E+05 | 4.319E−04 | 1.686 |
| Fab0069 | 0.35 | 0.75 | 1.376E+06 | 1.077E−03 | 0.783 | 3.010E+05 | 1.640E−03 | 5.448 |
| Fab0070 | 0.49 | 1.11 | 1.302E+06 | 1.201E−03 | 0.923 | 2.629E+05 | 9.743E−04 | 3.706 |
| Fab0071 | 0.45 | 0.43 | 1.565E+06 | 8.649E−04 | 0.553 | 2.684E+05 | 7.163E−04 | 2.669 |
| Fab0072 | 0.19 | 0.19 | 1.855E+06 | 6.136E−04 | 0.331 | 2.917E+05 | 2.619E−04 | 0.898 |
| Fab0073 | 0.29 | 0.32 | 1.848E+06 | 6.495E−04 | 10.351 | 2.925E+05 | 6.149E−04 | 2.103 |
| Fab0074 | 0.46 | 0.46 | 1.662E+06 | 7.818E−04 | 0.471 | 2.857E+05 | 7.930E−04 | 2.776 |

TABLE 7

Cynomolgus Monkey Transferrin Receptor 1 (cTfR1) Binding Parameters as Measured by Competition ELISA, SPR and BLI

| Fab ID | cTfR1 Phage Kd, nM | cTfR1 Fab ELISA Kd, nM | cTfR1 SPR ka (1/Ms) | cTfR1 SPR kd (1/s) | cTfR1 SPR Kd, nM | cTfR1 BLI conjugate ka (1/Ms) | cTfR1 BLI conjugate kd (1/s) | cTfR1 BLI conjugate Kd, nM |
|---|---|---|---|---|---|---|---|---|
| Fab0002 | 0.96 | 33.8 | 6.136E+05 | 1.545E−02 | 25.190 | 2.918E+05 | 7.323E−03 | 25.090 |
| Fab0060 | 1.56 | 4.58 | 1.315E+06 | 3.565E−03 | 2.711 | 2.762E+05 | 2.517E−03 | 9.112 |
| Fab0061 | 1.75 | 5.15 | 2.114E+06 | 3.705E−03 | 1.753 | 2.477E+05 | 1.696E−03 | 6.850 |
| Fab0062 | 3.48 | 9.14 | 1.599E+06 | 5.154E−03 | 3.224 | 2.385E+05 | 2.632E−03 | 11.030 |
| Fab0063 | 2.63 | 5.57 | 1.637E+06 | 4.461E−03 | 2.724 | 2.626E+05 | 2.197E−03 | 8.369 |
| Fab0064 | 2.02 | 5.04 | 1.497E+06 | 3.670E−03 | 2.452 | 3.191E+05 | 1.903E−03 | 5.963 |
| Fab0065 | 0.57 | 2.87 | 1.789E+06 | 2.591E−03 | 1.448 | 2.310E+05 | 1.301E−03 | 5.633 |
| Fab0066 | 1.34 | 9.4 | 1.169E+06 | 5.091E−03 | 4.353 | 3.342E+05 | 3.355E−03 | 10.040 |
| Fab0067 | 0.95 | 3.02 | 1.874E+06 | 3.275E−03 | 1.747 | 3.776E+05 | 1.896E−03 | 5.022 |
| Fab0068 | 1.75 | 7.37 | 1.566E+06 | 3.657E−03 | 2.336 | 2.490E+05 | 2.214E−03 | 8.894 |
| Fab0069 | 1.29 | 4.68 | 1.375E+06 | 3.745E−03 | 2.724 | 2.559E+05 | 2.451E−03 | 9.580 |
| Fab0070 | 1.39 | 15.32 | 1.287E+06 | 5.824E−03 | 4.524 | 2.445E+05 | 4.127E−03 | 16.880 |
| Fab0071 | 0.74 | 53.33 | 1.382E+06 | 1.124E−02 | 8.133 | 2.337E+05 | 4.291E−03 | 18.060 |
| Fab0072 | 1.18 | 11.88 | 2.779E+06 | 1.078E−02 | 3.880 | 3.681E+05 | 3.976E−03 | 10.800 |
| Fab0073 | 1.95 | 8.68 | 2.375E+06 | 6.773E−03 | 2.852 | 8.485E+05 | 3.215E−03 | 9.226 |
| Fab0074 | 2.14 | 17.5 | 2.443E+06 | 1.054E−02 | 4.313 | 2.642E+05 | 3.215E−03 | 12.170 |

Example 6. Synthesis of RNAi Agents and TfR1-Specific Conjugates

RNAi agent duplexes disclosed herein were synthesized in accordance with the following:

A. Synthesis.

The sense and antisense strands of the RNAi agents were synthesized according to phosphoramidite technology on solid phase used in oligonucleotide synthesis. Depending on the scale, a MerMade96E® (Bioautomation), a MerMadel2@(Bioautomation), or an OP Pilot 100 (GE Healthcare) was used. Syntheses were performed on a solid support made of controlled pore glass (CPG, 500 Å or 600 Å, obtained from Prime Synthesis, Aston, PA, USA). All RNA and 2'-modified RNA phosphoramidites were purchased from Thermo Fisher Scientific (Milwaukee, WI, USA). Specifically, the 2'-O-methyl phosphoramidites that were used included the following: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl RNA amidites. 5'-dimethoxytrityl-2'-O-methyl-inosine-3'-O-(2-cyanoethyl-N,N-diisopropylamino) phosphoramidites were purchased from Glen Research (Virginia). The inverted abasic (3'-O-dimethoxytrityl-2'-deoxyribose-5'-O-(2-cyanoethyl-N,N-diisopropylamino) phosphoramidites were purchased from ChemGenes (Wilmington, MA, USA). The following UNA phosphoramidites were used: 5'-(4,4'-Dimethoxytrityl)-N6-(benzoyl)-2',3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diiso-propyl)]-phosphoramidite. TFA aminolink phosphoramidites were also commercially purchased (ThermoFisher). The cyclopropyl phosphonate phosphoramidites were synthesized in accordance with International Patent Application Publication No. WO 2017/214112 (see also Altenhofer et. al., Chem. Communications (Royal Soc. Chem.), 57(55):6808-6811 (July 2021)).

B. Cleavage and Deprotection of Support Bound Oligomer.

After finalization of the solid phase synthesis, the dried solid support was treated with a 1:1 volume solution of 40 wt. % methylamine in water and 28% to 31% ammonium hydroxide solution (Aldrich) for 1.5 hours at 30° C. The solution was evaporated and the solid residue was reconstituted in water (see below).

C. Conjugation of RNAi Agents to Fabs and Capping with CP-1113.

RNAi agents described herein comprising a free amine were conjugated to L20-p

L20-p

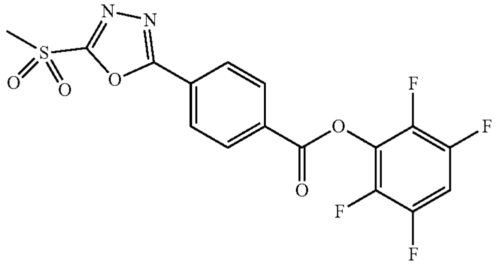

using standard amide reaction chemistry following cleavage from the solid phase. To a solution of Fab in PBS (0.2 umol, 1.0-10.0 mg/mL in PBS) was added a freshly prepared solution of (tris(2-carboxyethyl)phosphine) hydrochloride (TCEP-HCl) in PBS (5-20 eq, 70 mM). The reaction was held overnight at room temperature and covered from light. The next day, TCEP was removed by loading the reaction mixture on a PD-10 desalting column equilibrated with PBS and eluted with PBS. The concentration of Fab in the eluate was determined using the theoretical absorptivity factor at 280 nm. A solution of L20-modified sense strand in sodium phosphate buffer was prepared, and the concentration was determined using the theoretical absorptivity factor at 260 nm. To the desalted Fab solution was added L20-modified sense strand (1-1.3 eq, 0.5-2.5 mM), and the reaction was mixed end-over-end. Analysis by SEC Method 1 and AIEX Method 1 show a mixture of starting Fab, DAR1, and DAR2. After 1 hour, a solution of CP-1113-p:

CP-1113-p

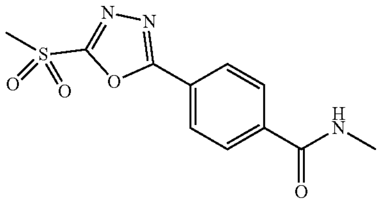

in DMSO and added to the reaction mixture (3 eq, 36 mM). After 1 hour, a solution of L-cysteine in PBS was added to the reaction mixture (6-10 eq, 165 mM). Finally, the conjugate was annealed by addition of antisense strand (1.2-1.5 eq, 0.5-2.5 mM). The conjugate was purified by an AKTA Pure FPLC system equipped with 20 mM tris pH 8 (Buffer A), 20 mM tris 1500 mM NaCl (Buffer B), and a 5×200 mm column packed with Tosoh SuperQ 5PW (20 micron). The crude reaction mixture was pump loaded onto the column and eluted with a gradient of 10-40% Buffer B. DAR1 and DAR2 fractions were differentiated by SEC Method 1, AEX Method 1, and Nanodrop 260/280 readings. DAR1 fractions were pooled and buffer exchanged to PBS using a PD-10 desalting column. The purified conjugate was analyzed by SEC Method 1 and eluted as a monomeric peak with a retention time of 13.2 minutes.

D. Conjugation of RNAi agents to Fabs and Capping with NEM.

RNAi agents described herein comprising a free amine were conjugated to L20-p

L20-p

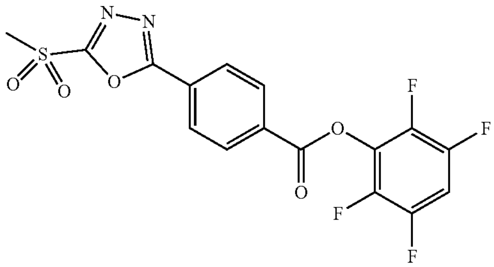

using standard amide reaction chemistry following cleavage from the solid phase. To a solution of Fab in PBS (10 mg, 0.2 umol, 1.0-10.0 mg/mL in PBS) was added a freshly prepared solution of TCEP-HCl in PBS (5-20 eq, 70 mM). The reaction was held overnight at room temperature and covered from light. The next day, TCEP was removed by loading the reaction mixture on to a PD-10 desalting column equilibrated with 20 mM tris pH 8 and eluted with 20 mM tris pH 8. The concentration of Fab in the eluate was determined using the theoretical absorptivity factor at 280 nm. A solution of L20-modified sense strand in sodium phosphate buffer was prepared, and the concentration was determined using the theoretical absorptivity factor at 260 nm. To the desalted Fab solution was added L20-modified sense strand (1-1.3 eq, 0.5-2.5 mM), and the reaction was mixed end-over-end. Analysis by SEC Method 1 and AIEX Method 1 show a mixture of starting Fab, DAR1, and DAR2. After 1 hour, a solution of N-ethyl maleimide (NEM) in 20 mM tris pH 8 was added to the reaction mixture (12 eq, 160 mM). After 1 h, the conjugate was annealed by addition of antisense strand (1.2-1.5 eq, 0.5-2.5 mM). The conjugate was purified by an AKTA Pure FPLC system equipped with 20 mM tris pH 8 (Buffer A), 20 mM tris 1500 mM NaCl (Buffer B), and a 5×200 mm column packed with Tosoh SuperQ 5PW (20 micron). The crude reaction mixture was loaded onto the column and eluted with a gradient of 10-40% Buffer B. DAR1 and DAR2 fractions were differentiated by SEC Method 1, AEX Method 1, and UV-Vis 260/280 measurements. DAR1 fractions were pooled and buffer exchanged to PBS using a PD-10 column. The purified conjugate was analyzed by SEC Method 1 and eluted as a monomeric peak with a retention time of 13.2 minutes.

SEC Method 1

| | |
|---|---|
| Mobile phases | Phosphate Buffered Saline pH 7.4 |
| Column | Superdex 200 Increase 10/300 GL<br>Cytiva PN 29219757 |
| Column temperature | 25° C. |

-continued

| | |
|---|---|
| Autosampler | ambient |
| Injection volume | 40 uL of 1 mg/mL protein (variable) |
| Flow rate | 1.0 mL/min isocratic |
| Wavelength | PDA 190-450 nm; monitor 230 nm, 260 nm, 280 nm |
| Run time | 30 minutes |

AIEX Method 1

| | |
|---|---|
| Mobile phases | C: 20 mM tris pH 8.0, D: 20 mM tris 1500 mM NaCl pH 8.0 |
| Column | ProPac SAX-10 4 mm × 250 mm, 10 um Thermo Fisher Scientific PN 054997 |
| Column temperature | 30° C. |
| Autosampler | 5° C. |
| Injection volume | 20 μl of 0.2 mg/mL oligo (variable) |
| Flow rate | 1.0 mL/min (variable) |
| Wavelength | PDA 190-450 nm; monitor 230 nm, 260 nm, 280 nm |
| Run time | 12.5 minutes |

| Gradient | Time(min) | Event | Value |
|---|---|---|---|
| | 0 | D. Conc | 0 |
| | 0.10 | D. Conc | 0 |
| | 0.11 | D. Conc | 25 |
| | 10.11 | D. Conc | 75 |
| | 10.11 | T. Flow | 1 |
| | 10.12 | D. Conc | 0 |
| | 10.12 | T. Flow | 1.5 |
| | 12.50 | Controller | Stop |

RNAi agents described herein comprising a free amine were first conjugated to L1026-p, i.e.:

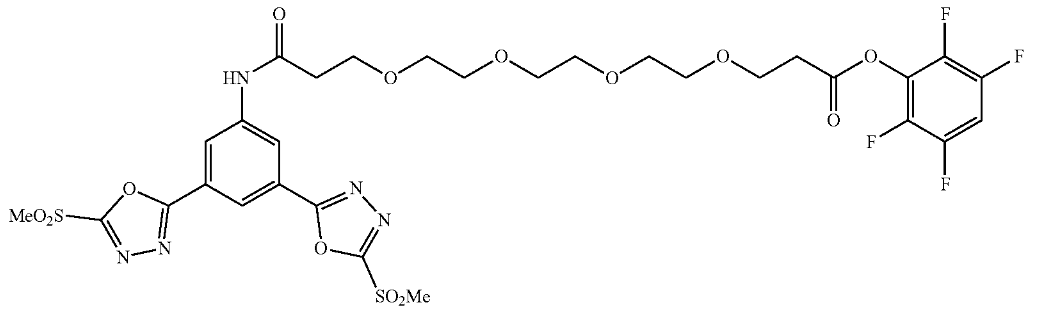

using standard solid phase synthesis coupling techniques to generate the L-1026-modified sense strand: (NH12-C6)s (invAb)scacuuuugAfCfCfugcuaaucaas(invAb) (i.e., CS915332, SEQ ID NO.: 151). Following cleavage from the solid phase, the RNAi agents described herein were synthesized according to the following procedure as exemplified by the synthesis of AC006448:

To a solution ofFab0070 (28 mg, 0.59 umol, 5.55 mng/mL in PBS) was added a freshly prepared solution of TCEP-HCl in PBS (5 eq, 70 mMV, 42 uL). The reduction was mixed end-over-end at ambient temperature for 15 minutes then held at 5° C. overnight without agitation. The next day, TCEP was removed by loading the reaction mixture on two PD-10 desalting columns (Cytiva) equilibrated with 20 mM tris 50 mM NaCl pH 7.6 (alternatively, 20 mM tris pH 8 or PBS buffer can be used) and eluted with the same buffer. The concentration of the Fab in the eluate was determined using the theoretical absorptivity factor at 280 nm. A solution of L-1026-modified sense strand (CS915332) in 10 mM sodium phosphate buffer pH 6.0-6.5 was prepared, and the concentration was determined using the theoretical absorptivity factor at 260 nm. To the desalted Fab solution was added L-1026-modified CS915332 (1.15 eq, 2.75 mM, 240 uL), and the reaction was mixed end-over-end at ambient temperature. Analysis by SEC Method 1 and AIEX Method 1 show a mixture of starting Fab0070, DAR1 product, and DAR2 product. After 30 m, a solution of L-cysteine in 20 mM tris 50 mM NaCl pH 7.6 (alternatively, some L-1026 conjugates have been prepared in 20 mM tris pH 8 or PBS buffer solutions) was added to the reaction mixture (10 eq, 165 mM, 36 uL). After 30 m, the conjugate was annealed by addition of antisense strand (CA003820) (1.3 eq, 1.45 mM in water, 529 uL). The conjugate was purified by an AKTA Pure FPLC system equipped with 20 mM tris pH 8 (Buffer A), 20 mM tris 1500 mM NaCl (Buffer B), and a 5×200 mm column packed with Tosoh SuperQ 5PW (20 micron). The crude reaction mixture was loaded onto the column and eluted with a gradient of 10-40% Buffer B. DAR1 and DAR2 fractions were differentiated by SEC Method 1, AIEX Method 1, and UV-Vis 260/280 measurements. DAR1 fractions were pooled and buffer exchanged to PBS using two PD-10 columns. The purified conjugate was analyzed by SEC Method 1 and eluted as a monomeric peak with a retention time of 7.2 minutes.

SEC Method 1

| | |
|---|---|
| Mobile phases | 2x Phosphate Buffered Saline pH 7.4 |
| Column | ACQUITY UPLC Protein BEH SEC Column, 200 Å, 1.7 μm, 4.6 mm × 300 mm Waters PN 186005226 |

-continued

| | |
|---|---|
| Column temperature | 30° C. |
| Autosampler | ambient |
| Injection volume | 2-5 uL |
| Flow rate | 0.3 mL/min |
| Wavelength | PDA 190-450 nm |
| Run time | 20 minutes |

AIEX Method 1

| | |
|---|---|
| Mobile phases | C: 20 mM tris pH 8.0, D: 20 mM tris 1500 mM NaCl pH 8.0 |
| Column | ProPac SAX-10 4 mm × 250 mm, 10 um Thermo Fisher Scientific PN 054997 |
| Column temperature | 30° C. |
| Autosampler | 5° C. |
| Injection volume | 5-20 μl |
| Flow rate | 1.0 mL/min (variable) |

-continued

| | | | |
|---|---|---|---|
| Wavelength | PDA 190-450 nm | | |
| Run time | 12.5 minutes | | |
| Gradient | Time(min) | Event | Value |
| | 0 | D. Conc | 10 |
| | 0.10 | D. Conc | 10 |
| | 0.11 | D. Conc | 25 |
| | 10.11 | D. Conc | 75 |
| | 10.11 | T. Flow | 1 |
| | 10.12 | D. Conc | 10 |
| | 10.12 | T. Flow | 1.5 |
| | 12.50 | Controller | Stop |

E. Conjugation of RNAi Agents to Fabs.

Synthesis of Fab0070-L-1288

To a solution of Fab0070 in PBS (82 mg, 8.2 mg/mL) was added a freshly prepared solution of TCEP-HCl in PBS (5 eq). The reaction mixture was held overnight at 5° C. The next day, the reaction mixture was buffer exchanged to 20 mM tris 50 mM NaCl pH 7.6 using four PD-10 columns equilibrated with the same buffer. The concentration was determined by Nanodrop, and the solution was diluted to 2 mg/mL with 20 mM tris 50 mM NaCl pH 7.6. The solution was diluted with DMSO (1.95 mL). A solution of L-1288 was prepared (2 mg/mL in DMSO) and charged (1.6 mL, 3.19 mg, 3 eq) over 15 m. After 10 m, the reaction was quenched with cysteine (10 eq). Insoluble material was removed by centrifugation. The supernatant removed, filtered, diluted 1:1 with PBS, and concentrated/desalted using Pierce 10K MVWCO spin columns to a volume of 8 mL. Finally, the solution was buffer exchanged by loading onto a HiPrep 26/10 desalting column and eluting with PBS. The final yield was approximately 80 mg.

Bioconjugation of L-1289

Lyophilized CS915332 (86 mg, 11.6 umol) was brought up in DMF (1.58 mL) and water (215 uL) and sonicated. To the solution was added triethylamine (9.7 uL, 6 eq) and a solution of L-1289 in DMF (50 mg/mL, 344 µL, 3 eq). The progress of the reaction was monitored by LCMS. After 1 h, added additional triethylamine (4 eq) and L-1289 solution (2 eq). After 20 m, LCMS showed complete conversion. The reaction mixture was acidified with phosphoric acid (200 mg/mL in water, 5 eq). The crude solution was added dropwise to a mixture of acetonitrile (43 mL) and PBS (1.7 mL). The precipitate was collected by centrifugation and the supernatant was discarded. The pellet was dissolved in water (1.5 mL) and added to acetonitrile (43 mL). The precipitate was collected by centrifugation and dissolved in PBS (5 mL). The yield was 88 mg (98%).

Conjugation of Fab0070-L-1288 with L-1307 Modified Sense Strand

To a solution of Fab0070-L-1288 in PBS (12.5 mg, 6.97 mg/mL, 1.79 mL, 1 eq) was added a solution of L1307-modified sense strand: L-1307s(invAb)scacuuuugAfCfCfugcuaaucaas(invAb), (i.e., CS009529, SEQ ID NO.: 152) in PBS (6.18 mg, 17.9 mg/mL, 345 µL, 3 eq). The combined solution was mixed end-over-end for 10 m then stored at 5° C. without agitation. The next day, the reaction was warmed to room temperature and annealed with antisense strand: cPrpusUfsgauuAfgcagGfuCfaAfaagsusg (i.e., AC003820, SEQ ID NO.: 153), 6.23 mg, 10.4 mg/mL, 599 µL, 3.3 eq. The conjugate was purified by an AKTA Pure FPLC system equipped with 20 mM tris pH 8 (Buffer A), 20 mM tris 1500 mM NaCl (Buffer B), and a 5×200 mm column packed with Tosoh SuperQ 5PW (20 micron). The crude reaction mixture was diluted to 40 mL with MPA, loaded onto the column, and eluted with a gradient of 10-40% Buffer B. DAR1-containing fractions were pooled and buffer exchanged to PBS using two PD-10 columns. The conjugate was analyzed by SEC Method 1 and found to be 99% pure with a retention time of 7.2 m. This procedure was also followed to generate the Fab-L-1288-L-1289-RNAi conjugates disclosed herein.

SEC Method 1

| | |
|---|---|
| Mobile phases | 2x Phosphate Buffered Saline pH 7.4 |
| Column | ACQUITY UPLC Protein BEH SEC Column, 200 Å, 1.7 µm, 4.6 mm × 300 mm Waters PN 186005226 |
| Column temperature | 30° C. |
| Autosampler | ambient |
| Injection volume | 2-5 uL |
| Flow rate | 0.3 mL/min |
| Wavelength | PDA 190-450 nm |
| Run time | 20 minutes |

F. Synthesis of Antibody-siRNA Linkers

The synthesis of various Fab linkers used throughout the present application are provided below.

Synthesis of 2,3,5,6-tetrafluorophenyl 16-((3,5-bis (5-(methylsulfonyl)-1,3,4-oxadiazol-2-yl)phenyl) amino)-16-oxo-4,7,10,13-tetraoxahexadecanoate (i.e., L-1026-p)

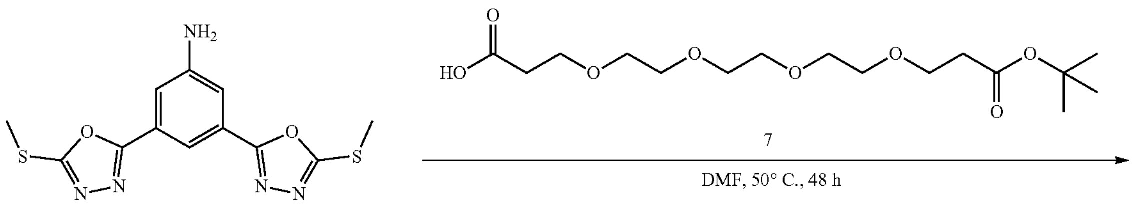

6

7

-continued

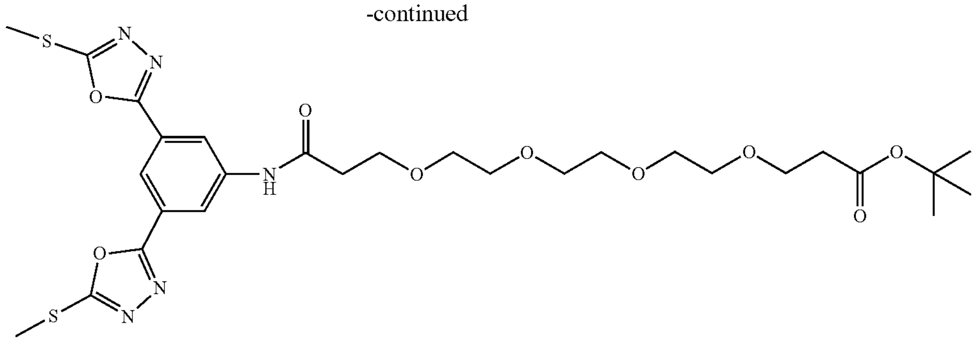

8

Compound 6 (2.35 g, 7.31 mmol; prepared according to Sarbisheh et al. *Bioconjugate Chemistry* 2020 31 (12), 2789-2806), EDC-HCl (2.38 g, 12.43 mmol), and K-Oxyma (2.50 g, 13.9 mmol) were combined as solids and slurried in DMF (190 mL) under N2 at ambient temperature. Compound 7 (1.1.92 g, 5.48 mmol) was added as a solution in DMF (10 mL). After 5 m, triethylamine (4.5 mL, 32.2 mmol) was added dropwise at ambient temperature. The reaction mixture was heated at 50° C. for 2 days. The reaction mixture was concentrated under reduced pressure to a red oil which was slurried in DCM (250 mL) and washed with sat. aq. sodium bicarbonate (200 mL). The layers were separated, and the aqueous layer was further extracted with DCM (100 mL). The combined organic phase was washed with water (200 mL) and brine (200 mL). The organic phase was dried over sodium sulfate, filtered, and concentrated. The residue was purified by normal phase $SiO_2$ chromatography with a gradient of ethyl acetate in DCM (0-100%). Yield of compound 8: 1.77 g (49%), partially contaminated with compound 6. Calculated mw for compound 8: 653.77 g/mol, found m/z (ESI, positive mode): 654.83.

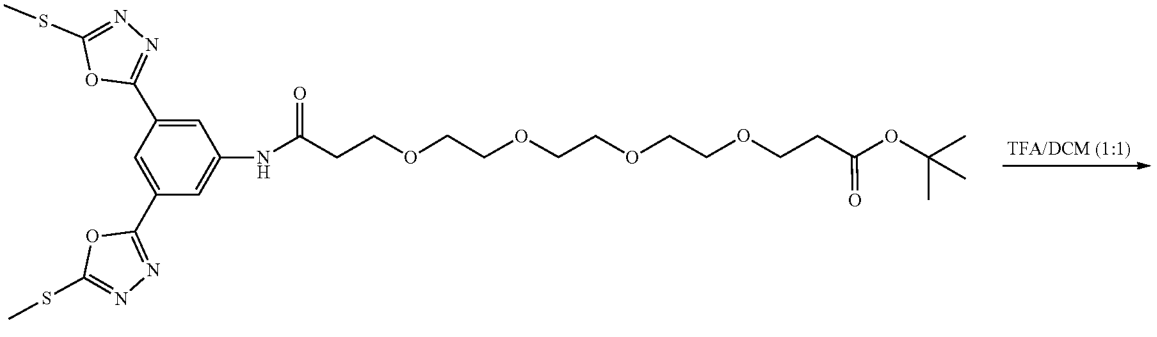

8

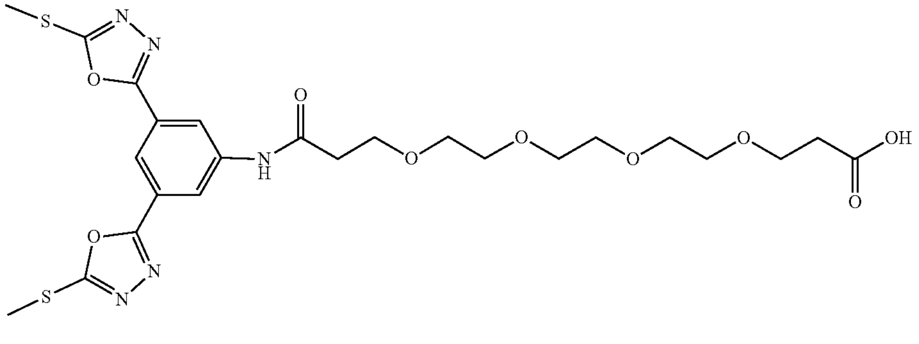

9

Compound 8 (1.77 g, 2.71 mmol) was dissolved in TFA:DCM [1:1](18 mL) and stirred at ambient temperature for 1 hour. The reaction mixture was concentrated under reduced pressure then coevaporated with toluene (3×30 mL). The residue was purified by normal phase $SiO_2$ chromatography with a gradient of DCM containing 0.1% formic acid and methanol (0-7%). Yield of compound 9: 1.30 g (80%). Calculated mw for compound 9: 597.66 g/mol, found m/z (ESI, positive mode): 598.79.

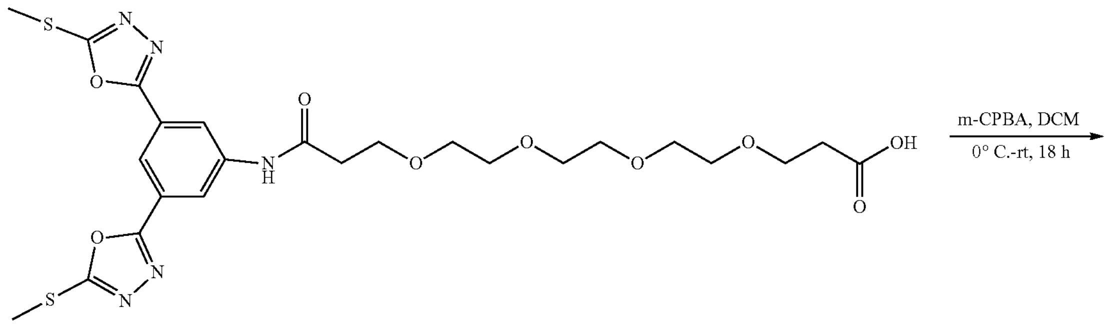

9

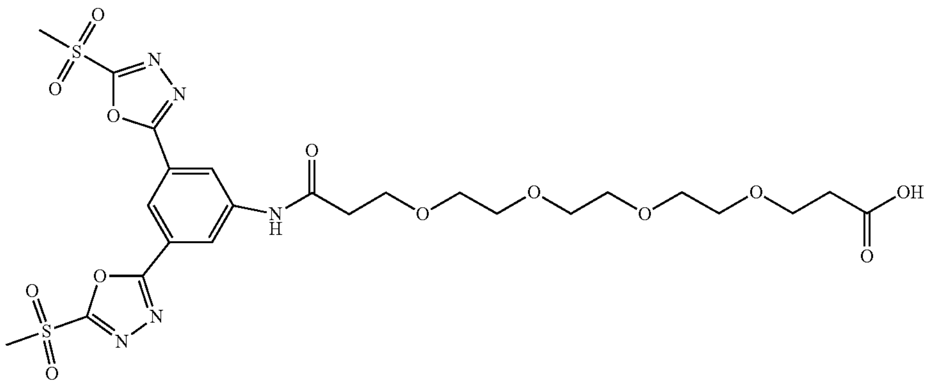

10

Compound 9 (1.30 g, 2.18 mmol) was dissolved in DCM (50 mL) and cooled to 0° C. A 100 mg/mL solution of m-CPBA solution was prepared by dissolving 10.38 g m-CPBA (77 wt %) in 80 mL DCM and drying with sodium sulfate until clear. To the solution of compound 9 was added 58 mL m-CPBA (5.85 g, 26.1 mmol) dropwise at 0° C. The reaction mixture was warmed to ambient temperature and allowed to proceed overnight. The reaction mixture was concentrated, slurried in DCM 0.1% formic acid (50 mL), and filtered. The filtrate was purified by normal phase $SiO_2$ chromatography with a gradient of DCM containing 0.1% formic acid and methanol (0-10%). Yield of compound 10: 1.03 g (72%). Calculated mw for compound 10: 661.65 g/mol, found m/z (ESI, positive mode): 662.65.

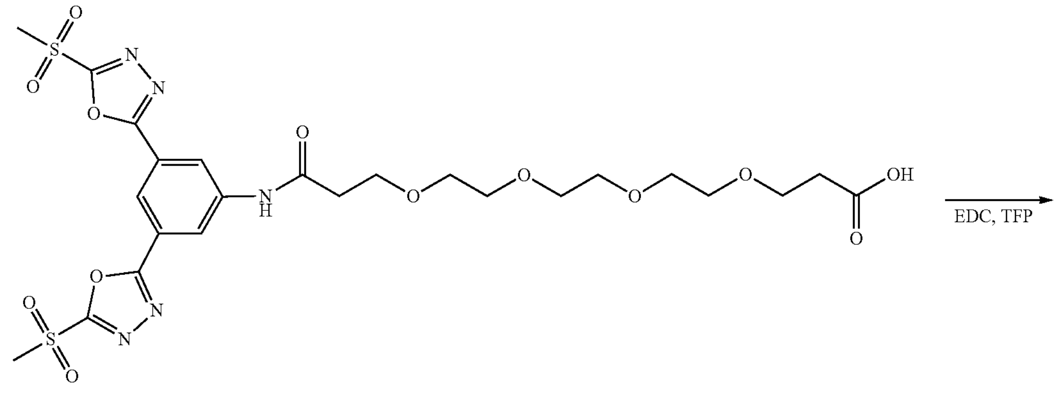

10

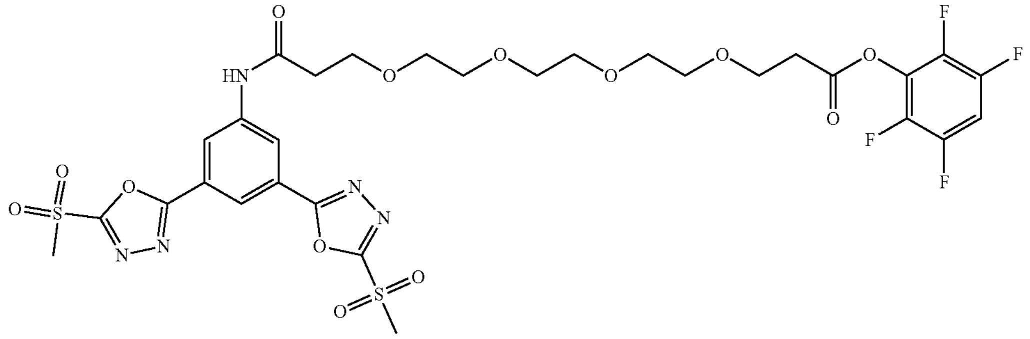

L-1026-p

To a solution of compound 10 (1.03 g, 1.56 mmol) in DCM:ACN [4:1](15 mL) at 0° C. was added EDC (0.448 g, 2.34 mmol) followed by a solution of TFP (0.310 g, 1.87 mmol) in DCM:ACN [4:1](5 mL). After 5 m, the reaction mixture was warmed to ambient temperature. After 1.5 h, the reaction mixture was concentrated to dryness. The crude was purified by preparative reverse phase HPLC (Phenomenex Gemini C18 50 mm×250 mm, 10 urn) using a gradient of water/acetonitrile containing 0.1% TFA. Product-containing fractions were concentrated under reduced pressure. Yield of L-1026-p: 1.10 g (87%). Calculated mw for compound L-1026-p: 809.71 g/mol, found m/z (ESI, positive mode): 810.62. $^1$H NMR (400 MHz,[$D_6$]DMSO, 25° C.): δ=2.64 (t, 2H), 3.00 (t, 2H), 3.49 (m, 12H), 3.74 (in, 10H), 7.92 (m, 1H), 8.34 (t, 1H), 8.68 (d, 2H), 10.67 (s, 1H).

Synthesis of L20-p

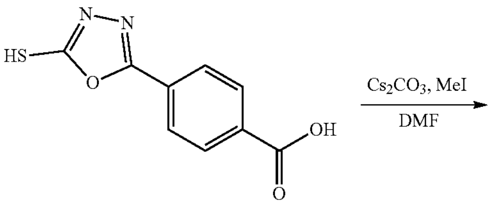

1

-continued

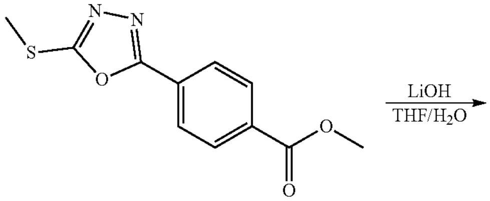

2

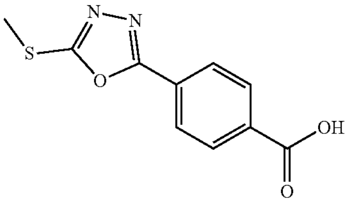

3

+

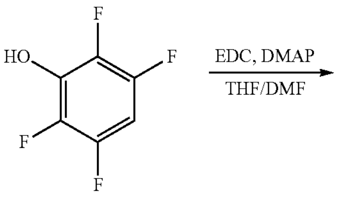

4

-continued

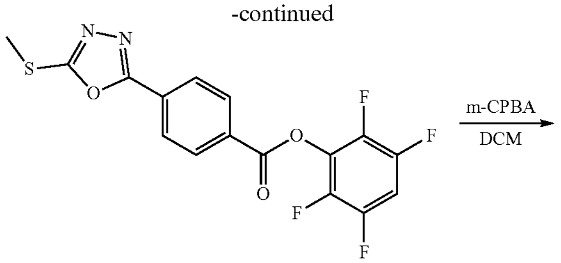

5

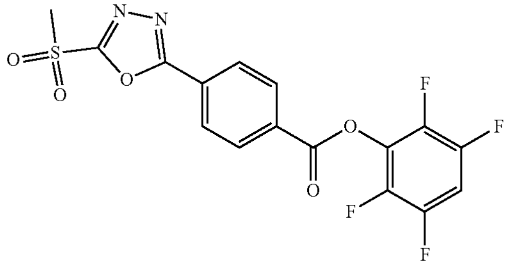

L20-p

To a suspension of compound 1 (5.00 g, 22.50 mmol) and $Cs_2CO_3$ (25.66 g, 78.75 mmol) in anhydrous DMF (80 mL) was added methyl iodide (4.20 mL, 67.50 mmol) at room temperature. The reaction mixture was stirred at room temperature for 48 hours. The reaction mixture was quenched with water (200 mL) and the mixture was extracted with EtOAc (3×100 mL). The organic phase was combined and washed with water and brine. The organic layer was dried over anhydrous $Na_2SO_4$ and concentrated. Compound 2 was obtained as a light yellow solid, 5.41 g, 96%. Compound 2 was used directly without further purification. LC-MS: [M+H] calculated 251.05, found 251.18.

3

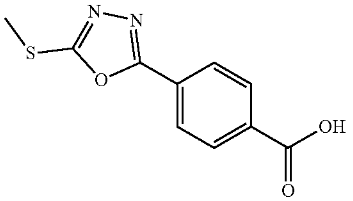

To a solution of compound 2 (5.41 g, 21.62 mmol) in THF/H2O (50 mL/50 mL) was added LiOH (2.59 g, 108.08 mmol) at room temperature. The reaction mixture was stirred at room temperature for 1 hour. After removing THF under vacuum, the pH was adjusted to ~2 by [C] HCl. Then EtOAc (3×60 mL) was used to extract. The organic layers were combined, washed with brine, then dried over anhydrous $Na_2SO_4$, and concentrated. Compound 3 was obtained as an off-white solid, 5 g, 98%. Compound 3 was used directly without further purification. LC-MS: calculated [M+H] 237.03, found 237.26.

5

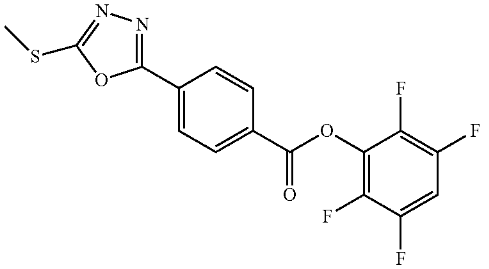

To a solution of compound 3 (5.81 g, 24.60 mmol) in THF/DMF (80 mL/20 mL) was added EDC (7.07 g, 36.90 mmol), DMAP (0.30 g, 2.46 mmol) and compound 4 (6.13 g, 36.90 mmol) at room temperature. The reaction mixture was stirred at room temperature overnight. After removing solvent under vacuum, the residue was loaded on a 120 g column and compound 5 was eluted with 0-50% EtOAc in hexanes. Compound 5 was obtained as a white solid, 9.36 g, 99%. LC-MS: calculated [M+H] 385.03, found 385.46.

L20-p

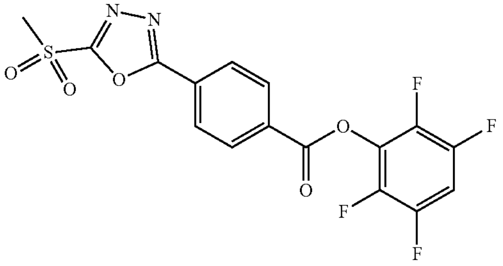

To a solution of compound 5 (2.29 g, 5.96 mmol) in DCM (110 mL) was added 700% m-CPBA (5.14 g, 27.79 mmol) at 0° C. The reaction mixture was stirred at room temperature for 6 hours. Another 1.8 g m-CPBA was added at room temperature. The reaction mixture was stirred at room temperature overnight. After filtration, the solvent was removed under vacuum. The residue was recrystallized from DCM/EtOAc (50 mL/50 mL) tw ice. Compound L20-p was obtained as white needle crystals, 1.93 g, 78%. LC-MS: calculated [M+H] 417, found 417.

Example 7. Relative Expression of mRNA After Delivering TfR1 Fab-Conjugated siRNA Antisense for the Target Androgen Receptor (AR) mRNA The siRNA duplexes are shown in sense and antisense in Tables 8 and 9, respectively. The antisense strand has complementary to AR mRNA. The sense siRNA strand is conjugated to the Fabs shown in the Table 8 below.

TABLE 8 siRNA sense sequence for targeting AR mRNA.

| Duplex ID | Sense Strand (5' → 3') | SEQ ID NO |
|---|---|---|
| AC003313 | Fab0002[NEM]L20-(NH-C6)s(invAb)scacuuuugAfCfCfugcuaaucaas(invAb) | 79 |

TABLE 8-continued siRNA sense sequence for targeting AR mRNA.

| Duplex ID | Sense Strand (5' → 3') | SEQ ID NO |
|---|---|---|
| AC004691 | Fab0064[NEM]L20-(NH-C6)s(invAb)scacuuuugAfCfCfugcuaaucaas(invAb) | 80 |
| AC004692 | Fab0066[NEM]L20-(NH-C6)s(invAb)scacuuuugAfCfCfugcuaaucaas(invAb) | 81 |
| AC004693 | Fab0067[NEM]L20-(NH-C6)s(invAb)scacuuuugAfCfCfugcuaaucaas(invAb) | 82 |
| AC004694 | Fab0072[NEM]L20-(NH-C6)s(invAb)scacuuuugAfCfCfugcuaaucaas(invAb) | 83 |
| AC004695 | Fab0073[NEM]L20-(NH-C6)s(invAb)scacuuuugAfCfCfugcuaaucaas(invAb) | 84 |
| AC004791 | Fab0060[NEM]L20-(NH-C6)s(invAb)scacuuuugAfCfCfugcuaaucaas(invAb) | 85 |
| AC004792 | Fab0061[NEM]L20-(NH-C6)s(invAb)scacuuuugAfCfCfugcuaaucaas(invAb) | 86 |
| AC004793 | Fab0062[NEM]L20-(NH-C6)s(invAb)scacuuuugAfCfCfugcuaaucaas(invAb) | 87 |
| AC004794 | Fab0063[NEM]L20-(NH-C6)s(invAb)scacuuuugAfCfCfugcuaaucaas(invAb) | 88 |
| AC004795 | Fab0065[NEM]L20-(NH-C6)s(invAb)scacuuuugAfCfCfugcuaaucaas(invAb) | 89 |
| AC004796 | Fab0068[NEM]L20-(NH-C6)s(invAb)scacuuuugAfCfCfugcuaaucaas(invAb) | 90 |
| AC004797 | Fab0069[NEM]L20-(NH-C6)s(invAb)scacuuuugAfCfCfugcuaaucaas(invAb) | 91 |
| AC004798 | Fab0070[NEM]L20-(NH-C6)s(invAb)scacuuuugAfCfCfugcuaaucaas(invAb) | 92 |
| AC004799 | Fab0071[NEM]L20-(NH-C6)s(invAb)scacuuuugAfCfCfugcuaaucaas(invAb) | 93 |
| AC004800 | Fab0074[NEM]L20-(NH-C6)s(invAb)scacuuuugAfCfCfugcuaaucaas(invAb) | 94 |
| AC004997 | Fab0056[NEM]L20-(NH-C6)s(invAb)scacuuuugAfCfCfugcuaaucaas(invAb) | 95 |
| AC004998 | Fab0058[NEM]L20-(NH-C6)s(invAb)scacuuuugAfCfCfugcuaaucaas(invAb) | 96 |
| AC005485 | Fab0002-L-1026-(NH-C6)s(invAb)scacuuuugAfCfCfugcuaaucaas(invAb) | 97 |
| AC005487 | Fab0044*[NEM]L20-(NH-C6)s(invAb)scacuuuugAfCfCfugcuaaucaas(invAb) | 98 |
| AC005488 | Fab0046**[NEM]L20-(NH-C6)s(invAb)scacuuuugAfCfCfugcuaaucaas(invAb) | 99 |
| AC006262 | Fab0002[CP-1113]L20-(NH-C6)s(invAb)scacuuuugAfCfCfugcuaaucaas(invAb) | 100 |
| AC006266 | Fab0061[CP-1113]L20-(NH-C6)s(invAb)scacuuuugAfCfCfugcuaaucaas(invAb) | 101 |
| AC006372 | Fab0070[CP-1113]L20-(NH-C6)s(invAb)scacuuuugAfCfCfugcuaaucaas(invAb) | 102 |
| AC006448 | Fab0070-L1026-(NH-C6)s(invAb)scacuuuugAfCfCfugcuaaucaas(invAb) | 103 |
| AC006597 | Fab0070-L1176-C6s(invAb)scacuuuugAfCfCfugcuaaucaas(invAb) | 104 |

TABLE 8-continued

| siRNA sense sequence for targeting AR mRNA. | | |
|---|---|---|
| Duplex ID | Sense Strand (5' → 3') | SEQ ID NO |
| AC006894 | Fab0165-SMCC-(NH-C6)s(invAb)scacuuuugAfCfCfugcuaaucaas(invAb) | 105 |
| AC006895 | Fab0166-SMCC-(NH-C6)s(invAb)scacuuuugAfCfCfugcuaaucaas(invAb) | 106 |
| AC006896 | Fab0168-SMCC-(NH-C6)s(invAb)scacuuuugAfCfCfugcuaaucaas(invAb) | 107 |
| AC006898 | Fab0167-SMCC-(NH-C6)s(invAb)scacuuuugAfCfCfugcuaaucaas(invAb) | 108 |
| AC007414 | Fab0070[CP-1113]L20-(NH-C6)s(invAb)scagcaucgAfcAfUfgguagacuas(invAb) | 109 |
| AC007865 | Fab0070[CP-1113]L20-(NH-C6)s(invAb)saggcaauuCfaGfuCfucguuguas(invAb) | 110 |
| AC007867 | Fab0070-L1026-(NH-C6)s(invAb)saggcaauuCfaGfuCfucguuguas(invAb) | 111 |
| AC007952 | Fab0070-L1026-(NH-C6)s(invAb)sccaugcaaGfaCfUfcacuuaguas(invAb) | 112 |
| AC007953 | Fab0070-L1026-(NH-C6)s(invAb)scuggagcaAfgUfuGfaaugaucas(invAb) | 113 |
| AC011951 | xAb000293-L20-(NH-C6)s(invAb)scacuuuugAfCfCfugcuaaucaas(invAb) | 114 |

*Fab0044 is identical to Fab0002 with the exception that the valine at position 205 of the light chain has been mutated to cysteine
**Fab0046 is identical to Fab0002 with the exception that the alanine at position 117 of the heavy chain has been mutated to cysteine
Key:
(a) represents 2'-O-methyl adenosine,
(c) represents 2'-O-methyl cytidine,
(g) represents 2'-O-methyl guanosine, and
(u) represents 2'-O-methyl uridine;
(Af) represents 2'-fluoro adenosine,
(Cf) represents 2'-fluoro cytidine,
(Gf) represents 2'-fluoro guanosine, and
(Uf) represents 2'-fluoro uridine;
(s) represents a phosphorothioate linkage;
(invAb) and (invAb)s represents inverted abasic nucleotide (structure in table 13 below);
cPrpus represents 5'-cyclopropyl phosphonate-2'-O-methyluridine-3'-phosphorothioate (structure in table 13 below);
(NH-C6)s structure in table 13 below;
L20 structure in table 13 below;
[CP-1113] indicates that the Fab has been capped using CP-1113p according to the procedure of Example 6C;
[NEM] indicates that the Fab has been capped using N-ethyl maleimide according to the procedure of Example 6D.

TABLE 9

| siRNA Antisense Sequence for Targeting AR mRNA | | |
|---|---|---|
| Duplex ID | Antisense Strand (5' → 3') | SEQ ID NO |
| AC003313 | cPrpusUfsgauuAfgcagGfuCfaAfaagsusg | 115 |
| AC004691 | cPrpusUfsgauuAfgcagGfuCfaAfaagsusg | 116 |
| AC004692 | cPrpusUfsgauuAfgcagGfuCfaAfaagsusg | 117 |
| AC004693 | cPrpusUfsgauuAfgcagGfuCfaAfaagsusg | 118 |
| AC004694 | cPrpusUfsgauuAfgcagGfuCfaAfaagsusg | 119 |
| AC004695 | cPrpusUfsgauuAfgcagGfuCfaAfaagsusg | 120 |
| AC004791 | cPrpusUfsgauuAfgcagGfuCfaAfaagsusg | 121 |
| AC004792 | cPrpusUfsgauuAfgcagGfuCfaAfaagsusg | 122 |

TABLE 9-continued

| siRNA Antisense Sequence for Targeting AR mRNA | | |
|---|---|---|
| Duplex ID | Antisense Strand (5' → 3') | SEQ ID NO |
| AC004793 | cPrpusUfsgauuAfgcagGfuCfaAfaagsusg | 123 |
| AC004794 | cPrpusUfsgauuAfgcagGfuCfaAfaagsusg | 124 |
| AC004795 | cPrpusUfsgauuAfgcagGfuCfaAfaagsusg | 125 |
| AC004796 | cPrpusUfsgauuAfgcagGfuCfaAfaagsusg | 126 |
| AC004797 | cPrpusUfsgauuAfgcagGfuCfaAfaagsusg | 127 |
| AC004798 | cPrpusUfsgauuAfgcagGfuCfaAfaagsusg | 128 |
| AC004799 | cPrpusUfsgauuAfgcagGfuCfaAfaagsusg | 129 |
| AC004800 | cPrpusUfsgauuAfgcagGfuCfaAfaagsusg | 130 |
| AC004997 | cPrpusUfsgauuAfgcagGfuCfaAfaagsusg | 131 |
| AC004998 | cPrpusUfsgauuAfgcagGfuCfaAfaagsusg | 132 |
| AC005485 | cPrpusUfsgauuAfgcagGfuCfaAfaagsusg | 133 |
| AC005487 | cPrpusUfsgauuAfgcagGfuCfaAfaagsusg | 134 |
| AC005488 | cPrpusUfsgauuAfgcagGfuCfaAfaagsusg | 135 |
| AC006262 | cPrpusUfsgauuAfgcagGfuCfaAfaagsusg | 136 |
| AC006266 | cPrpusUfsgauuAfgcagGfuCfaAfaagsusg | 137 |
| AC006372 | cPrpusUfsgauuAfgcagGfuCfaAfaagsusg | 138 |
| AC006448 | cPrpusUfsgauuAfgcagGfuCfaAfaagsusg | 139 |
| AC006597 | cPrpusUfsgauuAfgcagGfuCfaAfaagsusg | 140 |
| AC006894 | cPrpusUfsgauuAfgcagGfuCfaAfaagsusg | 141 |
| AC006895 | cPrpusUfsgauuAfgcagGfuCfaAfaagsusg | 142 |
| AC006896 | cPrpusUfsgauuAfgcagGfuCfaAfaagsusg | 143 |
| AC006898 | cPrpusUfsgauuAfgcagGfuCfaAfaagsusg | 144 |
| AC007414 | cPrpusAfsgucuAfccauGfuCfgAfugcussg | 145 |
| AC007865 | cPrpusAfscaAfcgagacUfgAfaUfugccssu | 146 |
| AC007867 | cPrpusAfscaAfcgagacUfgAfaUfugccssu | 147 |
| AC007952 | cPrpusAfscuaaGfugagUfcUfuGfcaugssg | 148 |
| AC007953 | cPrpusAfscsAfaCfgagacUfgAfaUfuGfccsu | 149 |
| AC011951 | cPrpusUfsgauuAfgcagGfuCfaAfaagsusg | 150 |

Key:
(a) represents 2'-O-methyl adenosine,
(c) represents 2'-O-methyl cytidine,
(g) represents 2'-O-methyl guanosine, and
(u) represents 2'-O-methyl uridine;
(Af) represents 2'-fluoro adenosine,
(Cf) represents 2'-fluoro cytidine,
(Gf) represents 2'-fluoro guanosine, and
(Uf) represents 2'-fluoro uridine;
(s) represents a phosphorothioate linkage;
cPrpus represents 5'-cyclopropyl phosphonate-2'-O-methyluridine-3'-phosphorothioate (structure in table 13 below).

TABLE 10
Shows the structures for cPrpus, (invAb)s, (invAb), L20, and NH—C6 defined in the Key above for sense and antisense sequences in Tables 8 and 9
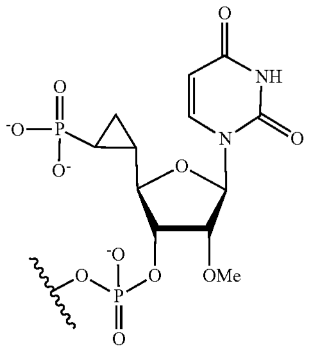
cPrpu
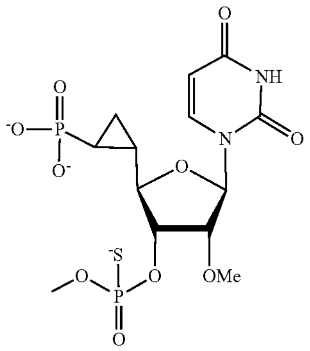
cPrpus
When positioned internally:
linkage towards 5' end
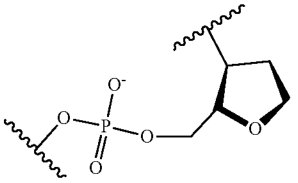
linkage towards 3' end
(invAb)
linkage towards 5' end
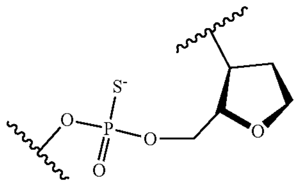
linkage towards 3' end
(invAb)s TABLE 10-continued
Shows the structures for cPrpus, (invAb)s, (invAb), L20, and NH—C6 defined in the Key above for sense and antisense sequences in Tables 8 and 9
When positioned at the 3' terminal end:
linkage towards 5' end
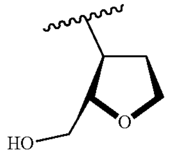
(invAb)
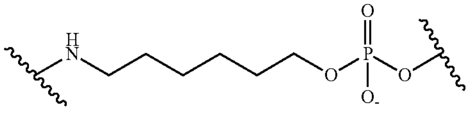
(NHC6)
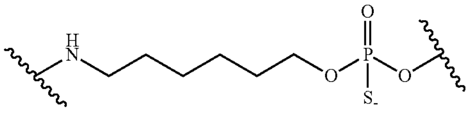
(NHC6)s
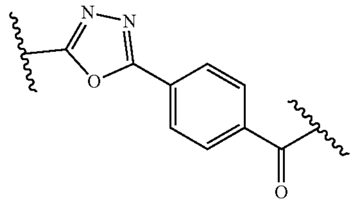
(L20)
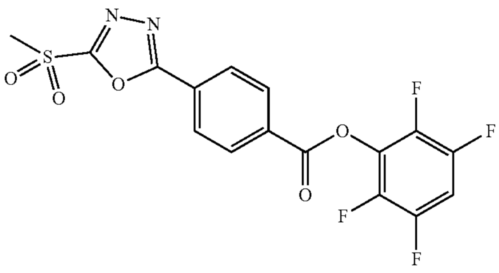
L20-p
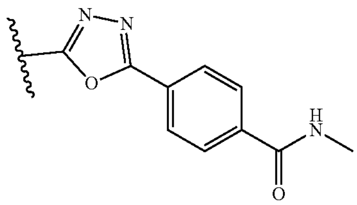
[CP-1113]

TABLE 10-continued
| Shows the structures for cPrpus, (invAb)s, (invAb), L20, and NH—C6 defined in the Key above for sense and antisense sequences in Tables 8 and 9 |
| --- |
| 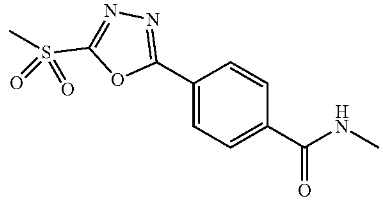<br>CP-1113-p |
| Linkage toward RNAi agent<br>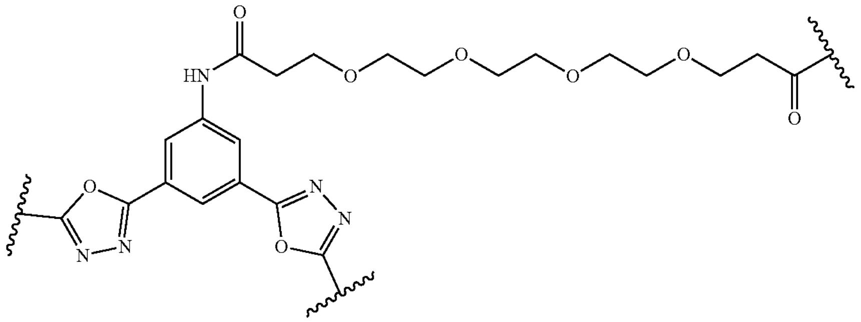<br>Linkage to Fab<br>L1026 |
| 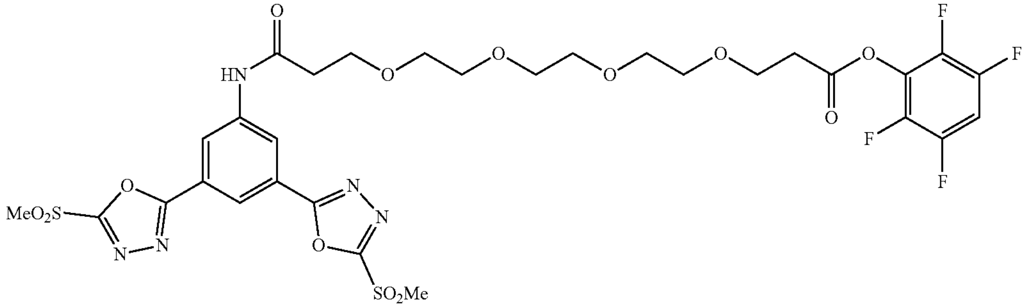 [SMILES: CS(=O)(=O)c1nnc(-c2cc(NC(=O)CCOCCOCCOCCOCCC(=O)Oc3c(F)c(F)cc(F)c3F)cc(-c3nnc(S(C)(=O)=O)o3)c2)o1]<br>L1026-p |
| Linkage to Fab<br>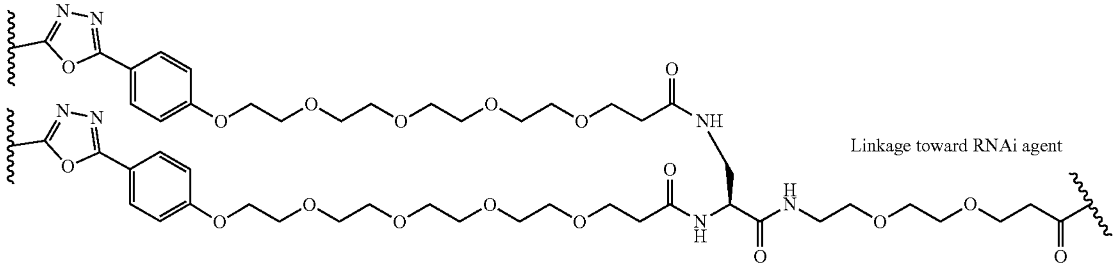<br>L1176 |

TABLE 10-continued

| Shows the structures for cPrpus, (invAb)s, (invAb), L20, and NH—C6 defined in the Key above for sense and antisense sequences in Tables 8 and 9 |
|---|
| 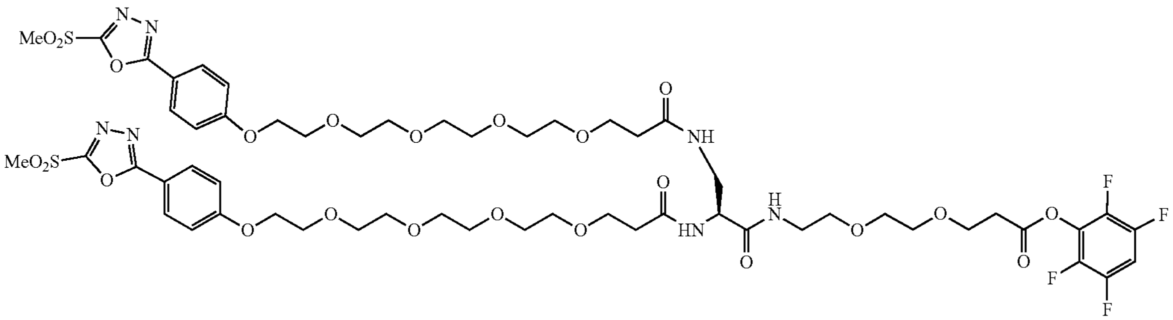 L1176-p |
| 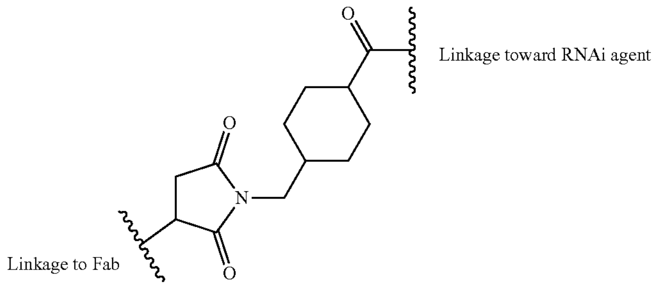 SMCC |
| 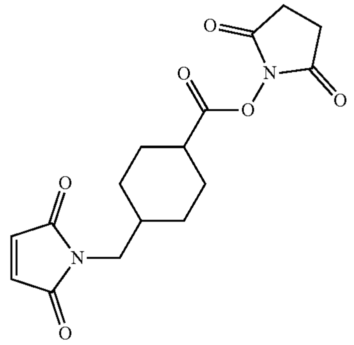 SMCC-p |

Example 8. In Vivo Knockdown of AR in Transgenic Tg B-hTfr1 Mice

On Study day 1, Tg B-hTfr1 mice were injected intravenously with either a dosing volume of 250 μL/25 g PBS (group 1) or 1.5 mg/kg of a TfR1-Fab conjugated siRNA at a dosing volume of 250 μL/25 g (groups 2-7), and dosed again on day 2 with the same formulation, according to Table 11 below:

TABLE 11

Dosing groups for the mice of Example 8.

| Group ID | Dosing Regimen | Animals dosed |
|---|---|---|
| Group 1 (PBS) | Day 1, Day 2 | n = 5 |
| Group 2 | Day 1: 1.5 mg/kg AC003313,<br>Day 2: 1.5 mg/kg AC003313 | n = 5 |

TABLE 11-continued

Dosing groups for the mice of Example 8.

| Group ID | Dosing Regimen | Animals dosed |
|---|---|---|
| Group 3 | Day 1: 1.5 mg/kg AC004691,<br>Day 2: 1.5 mg/kg AC004691 | n = 5 |
| Group 4 | Day 1: 1.5 mg/kg AC004692,<br>Day 2: 1.5 mg/kg AC004692 | n = 5 |
| Group 5 | Day 1: 1.5 mg/kg AC004693,<br>Day 2: 1.5 mg/kg AC004693 | n = 5 |
| Group 6 | Day 1: 1.5 mg/kg AC004694,<br>Day 2: 1.5 mg/kg AC004694 | n = 5 |
| Group 7 | Day 1: 1.5 mg/kg AC004695,<br>Day 2: 1.5 mg/kg AC004695 | n = 5 |

On day 15, mice were euthanized and the left half of the brain and thoracic spinal cord were collected and stored in 10% NBF. Tissue samples were taken from the right half of the brain, including thoracic spinal cord, cortex, cerebellum and striatum. Samples were analyzed by qPCR for Androgen Receptor (AR) mRNA knockdown. FIG. 1 shows relative AR mRNA knockdown in each of the four analyzed tissues for each group.

Example 9. In Vivo Knockdown of AR in Transgenic Tg B-hTfr1 Mice

On Study day 1, Tg B-hTfr1 mice were injected intravenously with either a dosing volume of 250 μL/25 g PBS (group 1) or 1.5 mg/kg of a TfR1-Fab conjugated siRNA at a dosing volume of 250 μL/25 g (groups 2-10), and dosed again on day 2 with the same formulation, according to Table 12 below:

TABLE 12

Dosing groups for the mice of Example 9.

| Group ID | Dosing Regimen | Animals dosed |
|---|---|---|
| Group 1 (PBS) | Day 1, Day 2 | n = 5 |
| Group 2 | Day 1: 1.5 mg/kg AC003313, Day 2: 1.5 mg/kg AC003313 | n = 5 |
| Group 3 | Day 1: 1.5 mg/kg AC004791, Day 2: 1.5 mg/kg AC004791 | n = 5 |
| Group 4 | Day 1: 1.5 mg/kg AC004792, Day 2: 1.5 mg/kg AC004792 | n = 5 |
| Group 5 | Day 1: 1.5 mg/kg AC004793, Day 2: 1.5 mg/kg AC004793 | n = 5 |
| Group 6 | Day 1: 1.5 mg/kg AC004794, Day 2: 1.5 mg/kg AC004794 | n = 5 |
| Group 7 | Day 1: 1.5 mg/kg AC004795, Day 2: 1.5 mg/kg AC004795 | n = 5 |
| Group 8 | Day 1: 1.5 mg/kg AC004796, Day 2: 1.5 mg/kg AC004796 | n = 5 |
| Group 9 | Day 1: 1.5 mg/kg AC004797, Day 2: 1.5 mg/kg AC004797 | n = 5 |
| Group 10 | Day 1: 1.5 mg/kg AC004798, Day 2: 1.5 mg/kg AC004798 | n = 5 |

Figure 2:
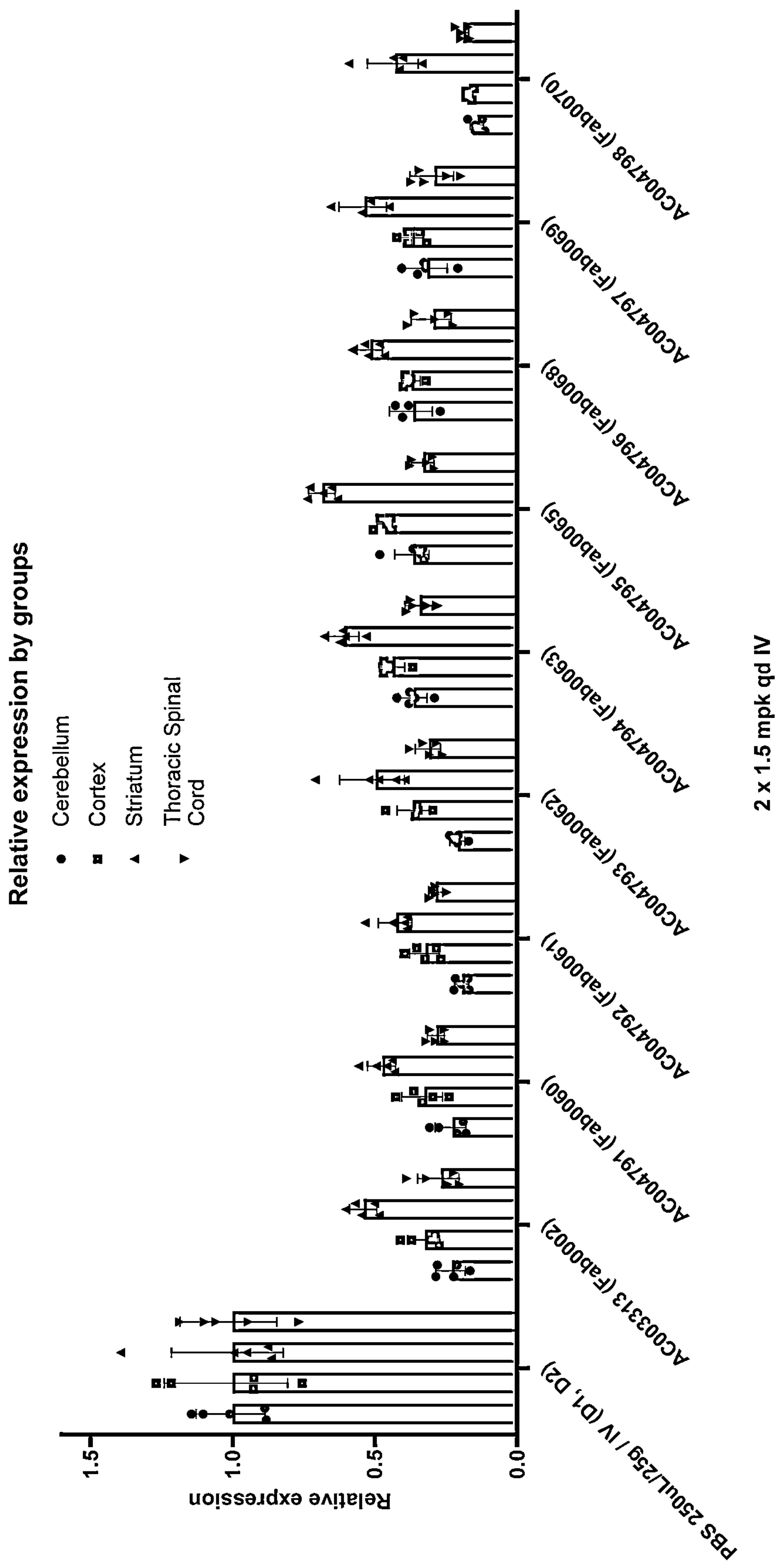
FIG. 2 shows relative androgen receptor mRNA expression knockdown after the delivery of select TfR1-targeting Fabs conjugated to siRNA with the antisense strand complementary to androgen receptor mRNA relative to control siRNA in different brain regions.

On day 15, mice were euthanized and the left half of the brain and thoracic spinal cord were collected and stored in 10% NBF. Tissue samples were taken from the right half of the brain, including thoracic spinal cord, cortex, cerebellum and striatuzn. Samples were analyzed by qPCR for Androgen Receptor (AR) mRNA knockdown. FIG. 2 shows relative AR mRNA knockdown in each of the four analyzed tissues for each group.

Example 10. In Vivo Knockdown of AR in Transgenic Tg B-hTfr1 Mice

On Study day 1, Tg B-hTfr1 mice were injected intravenously with either a dosing volume of 250 μL/25 g PBS (group 1) or 1.5 mg/kg of a TfR1-Fab conjugated siRNA at a dosing volume of 250 μL/25 g (groups 2-6), and dosed again on day 2 with the same formulation, according to Table 13 below:

TABLE 13

Dosing groups for the mice of Example 10.

| Group ID | Dosing Regimen | Animals dosed |
|---|---|---|
| Group 1 (PBS) | Day 1, Day 2 | n = 5 |
| Group 2 | Day 1: 1.5 mg/kg AC003313, Day 2: 1.5 mg/kg AC003313 | n = 5 |
| Group 3 | Day 1: 1.5 mg/kg AC004799, Day 2: 1.5 mg/kg AC004799 | n = 5 |
| Group 4 | Day 1: 1.5 mg/kg AC004800, Day 2: 1.5 mg/kg AC004800 | n = 5 |

TABLE 13-continued

Dosing groups for the mice of Example 10.

| Group ID | Dosing Regimen | Animals dosed |
|---|---|---|
| Group 5 | Day 1: 1.5 mg/kg AC004997, Day 2: 1.5 mg/kg AC004997 | n = 5 |
| Group 6 | Day 1: 1.5 mg/kg AC004998, Day 2: 1.5 mg/kg AC004998 | n = 5 |

Figure 3:
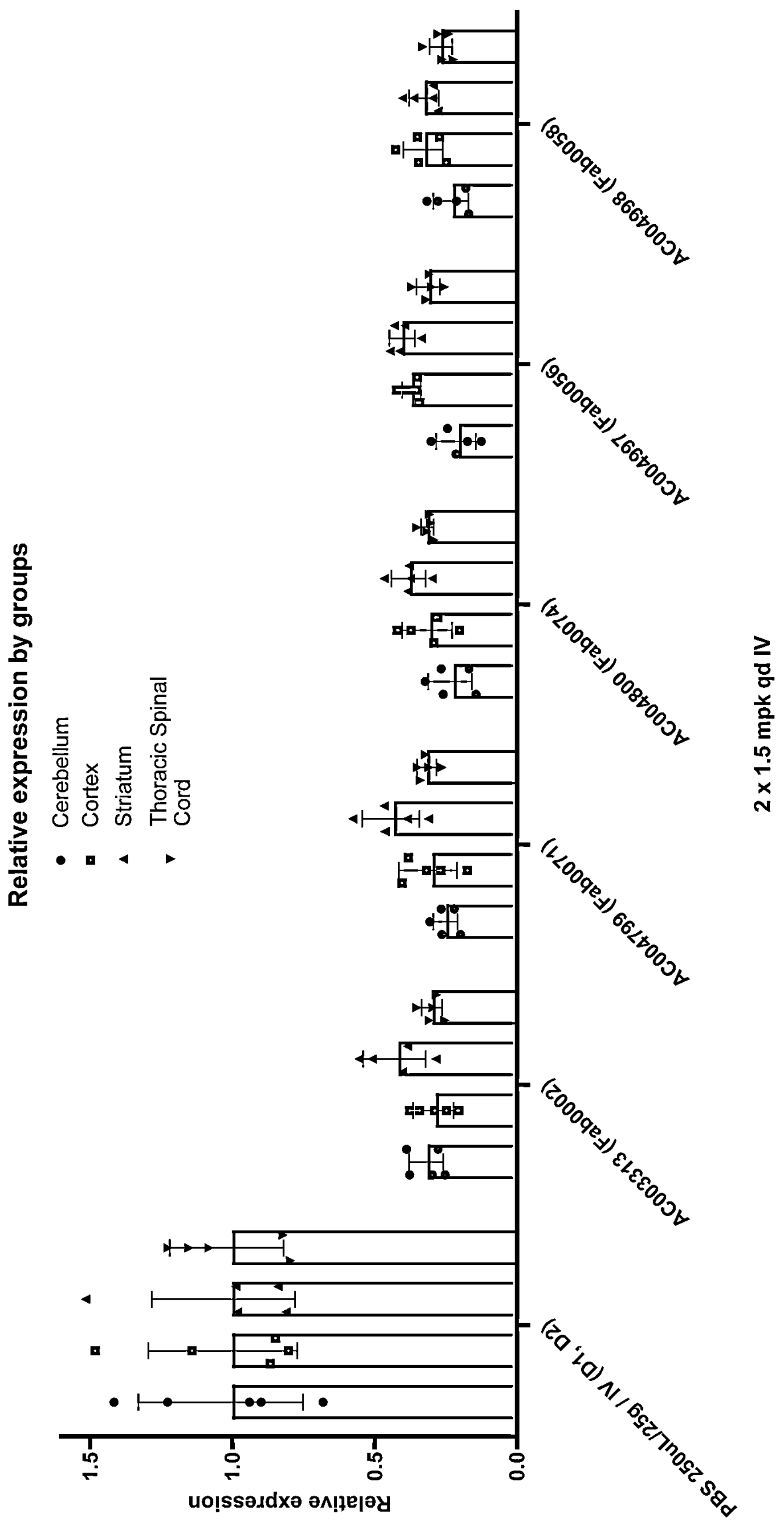
FIG. 3 shows relative androgen receptor mRNA expression knockdown after the delivery of select TfR1-targeting Fabs conjugated to siRNA with the antisense strand complementary to androgen receptor mRNA relative to control siRNA in different brain regions.

On day 15, mice were euthanized and the left half of the brain and thoracic spinal cord were collected and stored in 10% NBF. Tissue samples were taken from the right half of the brain, including thoracic spinal cord, cortex, cerebellum and striatum. Samples were analyzed by qPCR for Androgen Receptor (AR) mRNA knockdown. FIG. 3 shows relative AR mRNA knockdown in each of the four analyzed tissues for each group.

Example 11. In Vivo AR mRNA Gene Expression in Different Antibody Conjugate Groups Relative to the AC003313 (Fab0002) Control Group in Select Brain Regions In vivo AR mRNA gene knockdown of Fab-duplexes was measured in select brain regions. The AR mRNA gene expression in each group was normalized to the AC003313 (Fab0002-conjugated siRNA) group. FIG. 4 shows a graph of the relative expression values. The Fab0070-siRNA duplex group appears to have the lowest relative expression (highest gene knockdown).

Example 12. In Vivo Knockdown of AR mRNA Gene Expression in *Cynomolgus* Monkeys On Study day 0, *cynomolgus* monkeys were injected subcutaneously with either PBS or a compound formulation containing 3 mg/kg at a concentration of 1.5 mg/mL of an anti-TfR1 Fab-siRNA conjugate, according to Table 17 below. On Study day 7, groups 2, 3 and 4 were dosed with the same formulation as on day 0. All animals were dosed at a volume of 2 mL/kg.

TABLE 14

Dosing groups for the non-human primates of Example 12.

| Group ID | Dosing Regimen | Animals dosed |
|---|---|---|
| Group 1 (Control) | Day 0: PBS | n = 3 |
| Group 2 | Day 0: 3 mg/kg AC03313, Day 7: 3 mg/kg AC03313 | n = 2 |
| Group 3 | Day 0: 3 mg/kg AC06266, Day 7: 3 mg/kg AC06266 | n = 3 |
| Group 4 | Day 0: 3 mg/kg AC06372, Day 7: 3 mg/kg AC06372 | n = 3 |

Three (n==3) monkeys were dosed in groups 1 (control), 3 and 4 (trigger treated), and two (n=2) monkeys were dosed in group 2. On study day 28, animals from all groups were eutbanized and several tissues including Frontal Cortex, Temporal Cortex, Caudate, Cerebellum (cortex), Putamen, Motor Cortex, Medulla, Pons, Hippocampus, Thalamus, Hypothalamus, Midbrain, Substantia Nigra, Cervical dorsal root ganglion (DRG), Thoracic DRG, Lumbar DRG, Cervical Spinal Cord, Lumbar Spinal Cord, Thoracic Spinal Cord, Visual Cortex, Gastrocnemius, Triceps, Heart Left Atrium, Heart Right Atrium, Heart Left Ventricle, and Heart Right Ventricle were collected from each animal. Samples were analyzed by qPCR for AR mRNA knockdown. Average results for each group, relative to Group 1, are shown in Table 15 below:

TABLE 15

Relative expression of AR mRNA in various tissues analyzed by qPCR for each of the dosing groups of Example 12.

| | Frontal Cortex | | | Temporal Cortex | | | Caudate | | |
|---|---|---|---|---|---|---|---|---|---|
| Group | Rel Exp | Low Error | High Error | Rel Exp | Low Error | High Error | Rel Exp | Low Error | High Error |
| 1 | 1.000 | 0.203 | 0.254 | 1.000 | 0.223 | 0.287 | 1.000 | 0.517 | 1.069 |
| 2 | 0.757 | 0.064 | 0.070 | 0.774 | 0.094 | 0.107 | 0.764 | 0.255 | 0.383 |
| 3 | 0.446 | 0.127 | 0.178 | 0.421 | 0.134 | 0.198 | 0.476 | 0.117 | 0.156 |
| 4 | 0.284 | 0.040 | 0.046 | 0.412 | 0.087 | 0.110 | 0.694 | 0.143 | 0.181 |

| | Cerebellum (cortex) | | | Putamen | | | Motor Cortex | | |
|---|---|---|---|---|---|---|---|---|---|
| Group | Rel Exp | Low Error | High Error | Rel Exp | Low Error | High Error | Rel Exp | Low Error | High Error |
| 1 | 1.000 | 0.127 | 0.146 | 1.000 | 0.144 | 0.168 | 1.000 | 0.179 | 0.219 |
| 2 | 0.625 | 0.082 | 0.094 | 0.518 | 0.057 | 0.064 | 0.257 | 0.028 | 0.031 |
| 3 | 0.410 | 0.081 | 0.101 | 0.336 | 0.113 | 0.171 | 0.177 | 0.069 | 0.113 |
| 4 | 0.422 | 0.125 | 0.179 | 0.491 | 0.191 | 0.313 | 0.155 | 0.024 | 0.029 |

| | Medulla | | | Pons | | | Hippocampus | | |
|---|---|---|---|---|---|---|---|---|---|
| Group | Rel Exp | Low Error | High Error | Rel Exp | Low Error | High Error | Rel Exp | Low Error | High Error |
| 1 | 1.000 | 0.238 | 0.312 | 1.000 | 0.169 | 0.203 | 1.000 | 0.070 | 0.075 |
| 2 | 0.611 | 0.042 | 0.046 | 0.521 | 0.040 | 0.044 | 0.429 | 0.161 | 0.258 |
| 3 | 0.534 | 0.085 | 0.102 | 0.404 | 0.152 | 0.243 | 0.219 | 0.065 | 0.093 |
| 4 | 0.575 | 0.144 | 0.192 | 0.322 | 0.074 | 0.096 | 0.276 | 0.074 | 0.100 |

| | Thalamus | | | Hypothalamus | | | Midbrain | | |
|---|---|---|---|---|---|---|---|---|---|
| Group | Rel Exp | Low Error | High Error | Rel Exp | Low Error | High Error | Rel Exp | Low Error | High Error |
| 1 | 1.000 | 0.243 | 0.322 | 1.000 | 0.295 | 0.419 | 1.000 | 0.293 | 0.415 |
| 2 | 0.428 | 0.028 | 0.030 | 0.504 | 0.294 | 0.703 | 0.686 | 0.174 | 0.233 |
| 3 | 0.298 | 0.116 | 0.189 | 0.498 | 0.148 | 0.210 | 0.527 | 0.259 | 0.508 |
| 4 | 0.229 | 0.035 | 0.042 | 0.615 | 0.126 | 0.158 | 0.801 | 0.090 | 0.102 |

| | Substantia Nigra | | | Visual Cortex | | | Cervical DRG | | |
|---|---|---|---|---|---|---|---|---|---|
| Group | Rel Exp | Low Error | High Error | Rel Exp | Low Error | High Error | Rel Exp | Low Error | High Error |
| 1 | 1.000 | 0.446 | 0.806 | 1.000 | 0.223 | 0.286 | 1.000 | 0.186 | 0.229 |
| 2 | 0.838 | 0.348 | 0.595 | 0.551 | 0.067 | 0.076 | 1.044 | 0.166 | 0.197 |
| 3 | 0.260 | 0.053 | 0.066 | 0.343 | 0.096 | 0.134 | 0.623 | 0.168 | 0.230 |
| 4 | 0.454 | 0.063 | 0.073 | 0.264 | 0.044 | 0.053 | 0.610 | 0.113 | 0.138 |

| | Thoracic DRG | | | Lumbar DRG | | | Cervical Spinal Cord | | |
|---|---|---|---|---|---|---|---|---|---|
| Group | Rel Exp | Low Error | High Error | Rel Exp | Low Error | High Error | Rel Exp | Low Error | High Error |
| 1 | 1.000 | 0.423 | 0.733 | 1.000 | 0.195 | 0.243 | 1.000 | 0.278 | 0.386 |
| 2 | 0.635 | 0.173 | 0.238 | 0.663 | 0.208 | 0.304 | 0.489 | 0.172 | 0.264 |
| 3 | 0.842 | 0.429 | 0.874 | 0.871 | 0.092 | 0.103 | 0.304 | 0.032 | 0.036 |
| 4 | 1.223 | 0.189 | 0.224 | 0.637 | 0.296 | 0.552 | 0.450 | 0.120 | 0.164 |

| | Lumbar Spinal Cord | | | Thoracic Spinal Cord | | | Visual Cortex | | |
|---|---|---|---|---|---|---|---|---|---|
| Group | Rel Exp | Low Error | High Error | Rel Exp | Low Error | High Error | Rel Exp | Low Error | High Error |
| 1 | 1.000 | 0.123 | 0.140 | 1.000 | 0.162 | 0.194 | 1.000 | 0.223 | 0.286 |
| 2 | 0.532 | 0.131 | 0.175 | 0.789 | 0.326 | 0.556 | 0.551 | 0.067 | 0.076 |
| 3 | 0.427 | 0.107 | 0.142 | 0.470 | 0.171 | 0.268 | 0.343 | 0.096 | 0.134 |
| 4 | 0.351 | 0.091 | 0.123 | 0.725 | 0.285 | 0.471 | 0.264 | 0.044 | 0.053 |

TABLE 15-continued

Relative expression of AR mRNA in various tissues analyzed by qPCR for each of the dosing groups of Example 12.

| | Gastrocnemius | | | Triceps | | | Heart Left Atrium | | |
|---|---|---|---|---|---|---|---|---|---|
| Group | Rel Exp | Low Error | High Error | Rel Exp | Low Error | High Error | Rel Exp | Low Error | High Error |
| 1 | 1.000 | 0.468 | 0.880 | 1.000 | 0.195 | 0.243 | 1.000 | 0.096 | 0.106 |
| 2 | 0.228 | 0.077 | 0.116 | 0.663 | 0.208 | 0.304 | 0.315 | 0.107 | 0.163 |
| 3 | 0.335 | 0.063 | 0.077 | 0.871 | 0.092 | 0.103 | 0.205 | 0.030 | 0.035 |
| 4 | 0.279 | 0.100 | 0.156 | 0.637 | 0.296 | 0.552 | 0.205 | 0.071 | 0.108 |

| | Heart Right Atrium | | | Heart Left Ventricle | | | Heart Right Ventricle | | |
|---|---|---|---|---|---|---|---|---|---|
| Group | Rel Exp | Low Error | High Error | Rel Exp | Low Error | High Error | Rel Exp | Low Error | High Error |
| 1 | 1.000 | 0.113 | 0.127 | 1.000 | 0.119 | 0.135 | 1.000 | 0.122 | 0.139 |
| 2 | 0.299 | 0.114 | 0.185 | 0.150 | 0.044 | 0.062 | 0.251 | 0.035 | 0.040 |
| 3 | 0.231 | 0.038 | 0.046 | 0.149 | 0.026 | 0.031 | 0.418 | 0.049 | 0.056 |
| 4 | 0.210 | 0.067 | 0.098 | 0.125 | 0.040 | 0.059 | 0.232 | 0.039 | 0.047 |

As shown in Table 15, above, durable reduction of AR mnRNA expression was observed in multiple tissues for non-human primates treated with anti-TtR1 antibody-siRNA conjugate. Groups 3 (Fab0061-siRNA conjugate) and 4 (Fab0070-siRNA conjugate) outperformed Group 2 (Fab002-siRNA conjugate) in nearly every tissue analyzed, with the exception of Thoracic DRG and Lumbar DRG.

Table 15 also shows that. Fab0061 and Fab0070 are capable of delivering siRNA to skeletal muscle tissues such as gastrocnemius and triceps. Delivery to heart tissue is also possible using Fab0061 and Fab0070, with deep knockdown of AR mRNA shown in each section of the heart collected.

Example 13. In Vivo Knockdown of MAPT in in *Cynomolgus* Monkeys

As shown in Table 15, above, durable reduction of AR mRNA expression was observed in multiple tissues for non-human primates treated with anti-TfR1 antibody-siRNA conjugate. Groups 3 (Fab0061-siRNA conjugate) and 4 (Fab0070-siRNA conjugate) outperformed Group 2 (Fab002-siRNA conjugate) in nearly every tissue analyzed, with the exception of Thoracic DRG and Lumbar DRG.

On Study day 0, *cynomolgus* monkeys were injected with either artificial cerebrospinal fluid (aCSF, obtained from a commercial supplier) or a compound formulation containing either 3 mg/kg at a concentration of 1.5 mg/mL and a volume of 2 mL/kg, 15 mg/kg at a concentration of 7.5 mg/mL and a volume of 2 mL/kg, or 30 mg/kg at a concentration of 7.5 mg/mL and a volume of 4 mL/kg of AC007414 in aCSF according to Table 16 below: Table 16: Dosing groups for the non-human primates of Example 13.

TABLE 16

Dosing groups for the non-human primates of Example 13.

| Group ID | Animals dosed |
|---|---|
| Group 1 (aCSF) | n = 4 |
| Group 2 (3 × 3 mg/kg AC007414) | n = 4 |
| Group 3 (3 × 15 mg/kg AC007414) | n = 4 |
| Group 4 (3 × 30 mg/kg AC007414) | n = 4 |

Four (n=4) monkeys were dosed in each group. Monkeys were injected subcutaneously on days 0, 7, and 14. On study day 29, animals from each group were euthanized and brain and spinal cord tissue was collected from each animal. Samples were analyzed by qPCR for MAPT mRNA knockdown. Samples were analyzed by JESS for protein knockdown. Average mRNA knockdown for frontal cortex, hippocampus and thoracic spinal cord for each group, relative to Group 1, are shown in Table 17 below:

TABLE 17

Relative expression of MAPT mRNA in various tissues analyzed by qPCR for each of the dosing groups of Example 13

| | | Hippocampus Group Average (n = 4) | | | Frontal Cortex Group Average (n = 4) | | |
|---|---|---|---|---|---|---|---|
| Group # | Description | Rel. Exp. | Error (Low) | Error (High) | Rel. Exp. | Error (Low) | Error (High) |
| 1 | aCSF | 1.000 | 0.144 | 0.168 | 1.000 | 0.287 | 0.402 |
| 2 | AC007414 (3 mg/kg) | 0.265 | 0.058 | 0.073 | 0.191 | 0.054 | 0.075 |
| 3 | AC007414 (15 mg/kg) | 0.226 | 0.041 | 0.049 | 0.209 | 0.098 | 0.183 |
| 4 | AC007414 (30 mg/kg) | 0.200 | 0.054 | 0.075 | 0.164 | 0.055 | 0.082 |

TABLE 17-continued

Relative expression of MAPT mRNA in various tissues analyzed by qPCR for each of the dosing groups of Example 13

| | | Thoracic Spinal Cord Group Average (n = 4) | | |
|---|---|---|---|---|
| Group # | Description | Rel. Exp. | Error (Low) | Error (High) |
| 1 | aCSF | 1.000 | 0.192 | 0.238 |
| 2 | AC007414 (3 mg/kg) | 0.372 | 0.068 | 0.083 |
| 3 | AC007414 (15 mg/kg) | 0.252 | 0.023 | 0.025 |
| 4 | AC007414 (30 mg/kg) | 0.257 | 0.012 | 0.012 |

Figure 5:
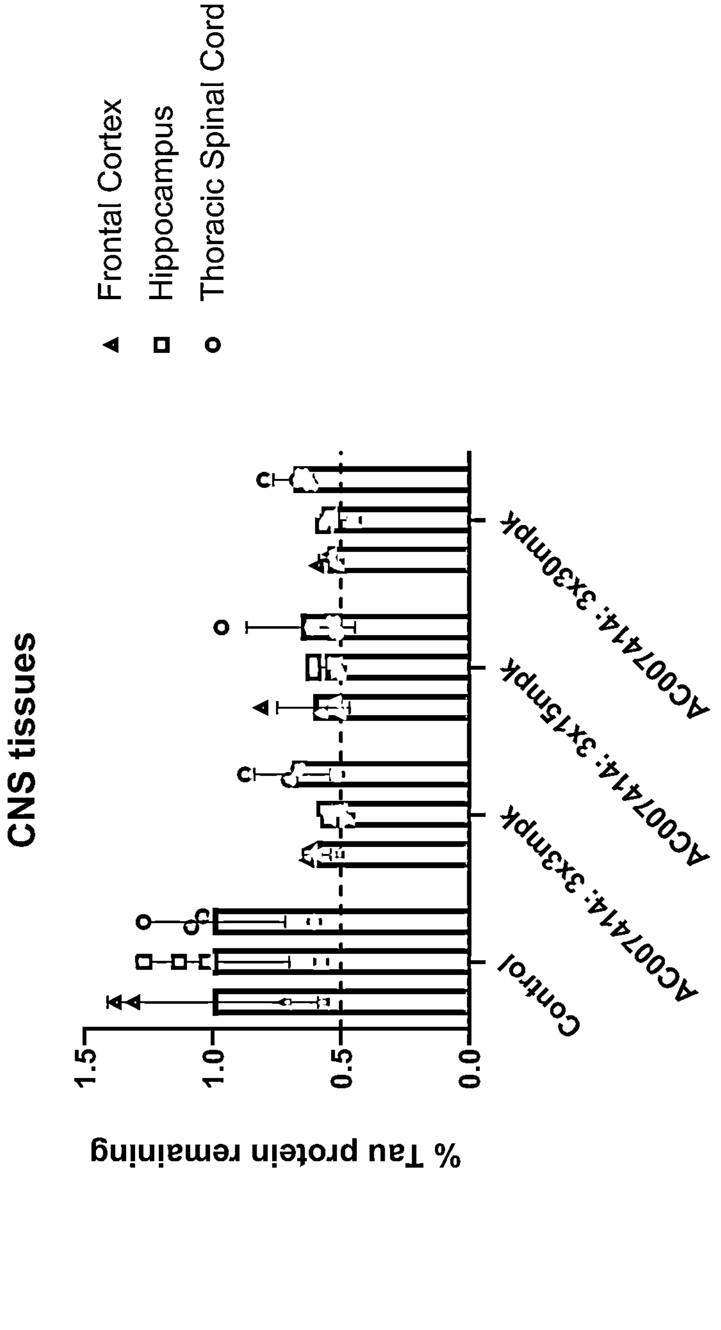
FIG. 5 shows the knockdown of MAPT protein in various tissues according to the description in Example 13.

Average protein knockdown for frontal cortex, hippocampus and thoracic spinal cord for each group, relative to Group 1, are shown in FIG. 5.

As can be seen in Table 17 and FIG. 5, MAPT RNAi agent bound to anti-Transferrin Fab070 achieved dose dependent and deep knockdown in CNS tissues when injected subcutaneously. The results demonstrate that treatment of MAPT-related diseases and disorder may be mitigated by RNAi agents administered subcutaneously.

It should be understood that the foregoing disclosure emphasizes certain specific embodiments of the invention and that all modifications or alternatives equivalent thereto are within the spirit and scope of the invention as set forth in the appended claims.

Example 14. In Vivo Administration of HTT RNAi Agents in *Cynomolgus* Monkeys HTT RNAi agents comprising anti-Tfr Fabs were evaluated in vivo in *Cynomolgus* monkeys. On Days 1, 8, and 15, four (n=4) male *Cynomolgus* monkeys for each test group were dosed with HTT RNAi agents formulated in PBS at 3.0 mg/kg (adjusted for individual animal body weight), 2.0 ml/kg dose volume, at 1.5 mg/ml dose concentration, or dosed with PBS. Each dose was administered via subcutaneous (SC) injection, and each dose was administered based on each respective animal's most recent body weight. The dosing was in accordance with the following Table 18.

TABLE 18

Dosing for Cynomolgus monkeys of Example 14.

| Group ID, Dose (RNAi Agent) | Dose Volume | Dosing Route | Dose Concentration | # of Animals (n=) |
|---|---|---|---|---|
| 1. PBS | N/A | SC Injection | N/A | n = 4 |
| 2. 3.0 mg/kg AC007867 | 2.0 ml/kg | SC Injection | 1.5 mg/ml | n = 4 |
| 3. 3.0 mg/kg AC007952 | 2.0 ml/kg | SC Injection | 1.5 mg/ml | n = 4 |
| 4. 3.0 mg/kg AC007953 | 2.0 ml/kg | SC Injection | 1.5 mg/ml | n = 4 |
| 5. 3.0 mg/kg AC007865 | 2.0 ml/kg | SC Injection | 1.5 mg/ml | n = 4 |

The test animals were of non-human primate, *Cynomolgus fascicularis* monkeys, male, non-naïve, aged 3-5 years. The test animals were acclimated to laboratory housing, per facility and acclimation standard operating procedures, for at least 14 days prior to the initiation of dosing. The RNAi agent test articles were administered via subcutaneous (SC) administration with a syringe and needle in the mid-scapular region.

Dose sites were shaved prior to dosing. Day 1 dose was delivered to the animals' left scapular region, Day 8 dose was delivered to the right scapular region, and Day 15 dose was delivered to the left scapular region. Each dose was given using syringe with a 23-25 gauge needle.

The test animals' individual body weights were recorded once pre-treatment Day −7, and then weekly through the duration of the study, and once prior to necropsy.

Cerebrospinal fluid (CSF), ~0.5 mL, was collected on Day −7 for all Groups. On Day 43 (day of necropsy), ~2.0 mL CSF was collected for all Groups. For the CSF collection procedure, all test animals were anesthetized by intravenous (IV) injection of ketamine (10 mg/kg, IV) and dexmedetomidine (0.02 mg/kg, intramuscular IM) and positioned in lateral recumbency. The skin covering the insertion point was shaved and wiped several times with individual chlorhexidine scrubs. The head of the animal was gently flexed to where the chin nearly touches the chest, but the airway was not obstructed. The professional palpated the occipital protuberance and wings of the atlas (C1). The needle was inserted perpendicularly above the atlas through the skin to access the subarachnoid space. If the bone was encountered, the needle was redirected either anteriorly or posteriorly until the designated access point was found. The CSF would flow freely through the needle once the proper placement has been achieved and collected into a cryotube tube. The needle was removed, and direct pressure was applied to the puncture site for at least two minutes. Once the procedure was complete, the animals were administered Carprofen 2-4 mg/kg SC every 12 hours for 1 day. Atipamezole (0.225 mg/kg, IM), was administered if necessary.

At Day 43, the *Cynomolgus* monkeys were euthanized. From the test animals, the following CNS tissues were collected: left and right brain hemisphere, spinal cord, dorsal root ganglion (DRG). Tissues other than the aforementioned tissues may also be collected, and should such extra tissues be collected, their biological data were similarly presented below. The collected tissues were analyzed for biological parameters.

From the collected tissues, cHTT mRNA transcript levels were quantified via qPCR, with cPPIB as endogenous control gene, normalized to Group 1 cynos dosed with PBS. The cHTT expression data is shown in the following Table 19.

TABLE 19 cHTT expression in cyno CNS tissues of Example 14.

| | Day 43 | | | | | |
|---|---|---|---|---|---|---|
| | Temporal Cortex | | | Frontal Cortex | | |
| Group ID | Rel Exp HTT | Error Low | Error High | Rel Exp HTT | Error Low | Error High |
| 1. PBS | 1.000 | 0.169 | 0.203 | 1.000 | 0.161 | 0.192 |
| 2. 3.0 mg/kg AC007867 | 0.331 | 0.063 | 0.078 | 0.333 | 0.056 | 0.067 |
| 3. 3.0 mg/kg AC007952 | 0.557 | 0.055 | 0.060 | 0.442 | 0.073 | 0.088 |
| 4. 3.0 mg/kg AC007953 | 0.518 | 0.077 | 0.090 | 0.503 | 0.065 | 0.074 |
| 5. 3.0 mg/kg AC007865 | 0.408 | 0.102 | 0.137 | 0.358 | 0.055 | 0.065 |

| | Motor Cortex | | | Caudate | | |
|---|---|---|---|---|---|---|
| Group ID | Rel Exp HTT | Error Low | Error High | Rel Exp HTT | Error Low | Error High |
| 1. PBS | 1.000 | 0.235 | 0.307 | 1.000 | 0.165 | 0.198 |
| 2. 3.0 mg/kg AC007867 | 0.393 | 0.072 | 0.088 | 0.413 | 0.072 | 0.087 |
| 3. 3.0 mg/kg AC007952 | 0.557 | 0.112 | 0.141 | 0.475 | 0.079 | 0.095 |
| 4. 3.0 mg/kg AC007953 | 0.775 | 0.099 | 0.114 | 0.424 | 0.060 | 0.069 |
| 5. 3.0 mg/kg AC007865 | 0.405 | 0.061 | 0.072 | 0.340 | 0.079 | 0.102 |

| | Putamen | | | Hippocampus | | |
|---|---|---|---|---|---|---|
| Group ID | Rel Exp HTT | Error Low | Error High | Rel Exp HTT | Error Low | Error High |
| 1. PBS | 1.000 | 0.106 | 0.119 | 1.000 | 0.164 | 0.196 |
| 2. 3.0 mg/kg AC007867 | 0.411 | 0.030 | 0.032 | 0.306 | 0.071 | 0.092 |
| 3. 3.0 mg/kg AC007952 | 0.795 | 0.100 | 0.114 | 0.515 | 0.089 | 0.108 |
| 4. 3.0 mg/kg AC007953 | 0.698 | 0.083 | 0.095 | 0.498 | 0.062 | 0.071 |
| 5. 3.0 mg/kg AC007865 | 0.456 | 0.068 | 0.080 | 0.302 | 0.044 | 0.051 |

| | Cerebellum | | |
|---|---|---|---|
| Group ID | Rel Exp HTT | Error Low | Error High |
| 1. PBS | 1.000 | 0.357 | 0.556 |
| 2. 3.0 mg/kg AC007867 | 0.883 | 0.307 | 0.471 |
| 3. 3.0 mg/kg AC007952 | 0.989 | 0.167 | 0.201 |
| 4. 3.0 mg/kg AC007953 | 1.168 | 0.188 | 0.224 |
| 5. 3.0 mg/kg AC007865 | 0.795 | 0.266 | 0.401 |

In the temporal cortex, frontal cortex, motor cortex, caudate, hippocampus, Groups 2-5 showed reduction in HTT transcripts out to at least Day 43 post dose. In the putamen, Groups 2, 4, and 5 showed reduction in HTT transcripts out to at least Day 43 post dose. Most notably, the most significant HTT transcript reduction was seen in the hippocampus, three doses of 3.0 mg/kg AC007867 showed ~69% HTT transcript inhibition (0.306), and three doses of 3.0 mg/kg AC007865 showed ~70% HTT transcript inhibition (0.302).

HTT protein expression was analyzed via Jess protein assay in the cyno tissues, normalized to Group 1 cynos dosed with PBS. HTT protein was quantified using Anti-Huntingtin Protein Antibody (Sigma-Aldrich®, Cat. MAB2166). The HTT protein expression data is shown in the following Table 20.

TABLE 20

HTT protein expression in cyno CNS tissues of Example 14.

| | Day 43 | | | | | |
|---|---|---|---|---|---|---|
| | Temporal Cortex | | Frontal Cortex | | Motor Cortex | |
| Group ID | Rel Exp HTT | Std Dev+/− | Rel Exp HTT | Std Dev+/− | Rel Exp HTT | Std Dev+/− |
| 1. PBS | 1.000 | 0.103 | 1.000 | 0.019 | 1.000 | 0.130 |
| 2. 3.0 mg/kg AC007867 | 0.160 | 0.041 | 0.171 | 0.016 | 0.143 | 0.025 |
| 3. 3.0 mg/kg AC007952 | 0.486 | 0.057 | 0.390 | 0.031 | 0.336 | 0.027 |
| 4. 3.0 mg/kg AC007953 | 0.407 | 0.056 | 0.353 | 0.092 | 0.287 | 0.034 |
| 5. 3.0 mg/kg AC007865 | 0.189 | 0.030 | 0.168 | 0.058 | 0.146 | 0.033 |

| | Caudate | | Putamen | | Hippocampus | |
|---|---|---|---|---|---|---|
| Group ID | Rel Exp HTT | Std Dev+/− | Rel Exp HTT | Std Dev+/− | Rel Exp HTT | Std Dev+/− |
| 1. PBS | 1.000 | 0.082 | 1.000 | 0.090 | 1.000 | 0.050 |
| 2. 3.0 mg/kg AC007867 | 0.176 | 0.027 | 0.178 | 0.059 | 0.179 | 0.034 |
| 3. 3.0 mg/kg AC007952 | 0.407 | 0.102 | 0.520 | 0.120 | 0.479 | 0.076 |
| 4. 3.0 mg/kg AC007953 | 0.346 | 0.079 | 0.432 | 0.125 | 0.468 | 0.031 |
| 5. 3.0 mg/kg AC007865 | 0.198 | 0.044 | 0.199 | 0.041 | 0.201 | 0.015 |

| | Cerebellum | |
|---|---|---|
| Group ID | Rel Exp HTT | Std Dev+/− |
| 1. PBS | 1.000 | 0.191 |
| 2. 3.0 mg/kg AC007867 | 0.655 | 0.049 |
| 3. 3.0 mg/kg AC007952 | 0.704 | 0.154 |
| 4. 3.0 mg/kg AC007953 | 0.659 | 0.082 |
| 5. 3.0 mg/kg AC007865 | 0.636 | 0.192 |

In the temporal cortex, frontal cortex, motor cortex, caudate, putamen, hippocampus, and cerebellum, Groups 2-5 showed reduction in HTT protein out to at least Day 43 post dose. In the liver, Groups 2, 3, and 5 showed reduction in HTT protein out to at least Day 43 post dose. Most notably, the most significant HTT protein reduction is seen in the motor cortex, three doses of 3.0 mg/kg AC007867 showed D86 HTT protein inhibition (0.143), and three doses of 3.0 mg/kg Am007865 showed 85 HTT protein inhibition (0.146).

Example 15. In Vivo Knockdown of AR in Transgenic Tg B-hTfr1 Mice

AR RNAi agents were evaluated in vivo in mouse. On Day 1 and Day 2, five (n=5) female B-hTFR1 mice were administered, via subcutaneous (SC) injection, either saline or AR RNAi agents (formulated in saline at 0.75 or 1.5 mg/kg animal body weight), at total dosing volume of 250 µL/25 g. Dosing was in accordance with Table 21 below.

TABLE 21

Dosing groups for the mice of Example 15.

| Group ID | Dosing Route | # Animals (n=) |
|---|---|---|
| 1. PBS | Day 1 and Day 2: SC Injection | n = 4 |
| 2. 1.5 mg/kg AC003313 | Day 1 and Day 2: SC Injection | n = 5 |
| 3. 0.75 mg/kg AC004791 | Day 1 and Day 2: SC Injection | n = 5 |
| 4. 1.5 mg/kg AC004791 | Day 1 and Day 2: SC Injection | n = 5 |
| 5. 0.75 mg/kg AC004792 | Day 1 and Day 2: SC Injection | n = 5 |
| 6. 1.5 mg/kg AC004792 | Day 1 and Day 2: SC Injection | n = 5 |
| 7. 0.75 mg/kg AC004798 | Day 1 and Day 2: SC Injection | n = 5 |
| 8. 1.5 mg/kg AC004798 | Day 1 and Day 2: SC Injection | n = 5 |
| 9. 1.5 mg/kg AC005485 | Day 1 and Day 2: SC Injection | n = 5 |
| 10. 1.5 mg/kg AC005487 | Day 1 and Day 2: SC Injection | n = 5 |
| 11. 1.5 mg/kg AC005488 | Day 1 and Day 2: SC Injection | n = 5 |
| 12. 1.5 mg/kg AC006262 | Day 1 and Day 2: SC Injection | n = 5 |

B-hTFR1 mice, also known as C57BL/6-Tfrc$^{tm1(TFRC)}$ $_{Bcgen}$/Bcgen mice (Biocytogen), have the exons 4-19 of mouse Tfr1 gene that encode the extracellular region replaced by human TFR1 exons 4-19.

Each of the AR RNAi agents included modified nucleotides that were conjugated at the 5' terminal end of the sense strand to a targeting ligand that included an antigen binding moiety having the modified sequences as set forth in the duplex structures herein.

On Day 15, the mice were euthanized. From the mice, thoracic spinal cord and cerebellum, striatum, and cortex were harvested and collected for analysis. mAR mRNA transcript expression was analyzed via qPCR, with mPPIA as endogenous gene, normalized to Group 1 mice dosed with saline. The mAR expression data is shown in the following Table 22.

TABLE 22

Relative expression of mAR in mice thoracic spinal cord, cerebellum, striatum, and cortex, of Example 15.

| | Day 15 | | | | | |
|---|---|---|---|---|---|---|
| | Thoracic Spinal Cord | | | Right Cerebellum | | |
| Group ID | Rel. Exp. mAR | Error (Low) | Error (High) | Rel. Exp. mAR | Error (Low) | Error (High) |
| 1. PBS | 1.000 | 0.293 | 0.415 | 1.000 | 0.309 | 0.447 |
| 2. 1.5 mg/kg AC003313 | 0.247 | 0.083 | 0.125 | 0.211 | 0.047 | 0.061 |
| 3. 0.75 mg/kg AC004791 | 0.338 | 0.139 | 0.235 | 0.215 | 0.046 | 0.059 |
| 4. 1.5 mg/kg AC004791 | 0.320 | 0.098 | 0.141 | 0.204 | 0.042 | 0.053 |
| 5. 0.75 mg/kg AC004792 | 0.359 | 0.097 | 0.133 | 0.298 | 0.110 | 0.174 |
| 6. 1.5 mg/kg AC004792 | 0.140 | 0.040 | 0.056 | 0.206 | 0.060 | 0.084 |
| 7. 0.75 mg/kg AC004798 | 0.180 | 0.053 | 0.076 | 0.182 | 0.029 | 0.034 |
| 8. 1.5 mg/kg AC004798 | 0.117 | 0.030 | 0.040 | 0.098 | 0.027 | 0.037 |
| 9. 1.5 mg/kg AC005485 | 0.096 | 0.020 | 0.026 | 0.121 | 0.030 | 0.039 |
| 10. 1.5 mg/kg AC005487 | 0.092 | 0.027 | 0.038 | 0.204 | 0.053 | 0.071 |
| 11. 1.5 mg/kg AC005488 | 0.076 | 0.015 | 0.019 | 0.178 | 0.103 | 0.244 |
| 12. 1.5 mg/kg AC006262 | 0.089 | 0.021 | 0.027 | 0.077 | 0.017 | 0.021 |

| | Right Cortex | | | Right Striatum | | |
|---|---|---|---|---|---|---|
| Group ID | Rel. Exp. mAR | Error (Low) | Error (High) | Rel. Exp. mAR | Error (Low) | Error (High) |
| 1. PBS | 1.000 | 0.244 | 0.323 | 1.000 | 0.185 | 0.226 |
| 2. 1.5 mg/kg AC003313 | 0.333 | 0.079 | 0.104 | 0.309 | 0.104 | 0.157 |
| 3. 0.75 mg/kg AC004791 | 0.489 | 0.076 | 0.090 | 0.481 | 0.086 | 0.105 |
| 4. 1.5 mg/kg AC004791 | 0.336 | 0.052 | 0.062 | 0.404 | 0.069 | 0.084 |
| 5. 0.75 mg/kg AC004792 | 0.417 | 0.078 | 0.095 | 0.304 | 0.089 | 0.125 |
| 6. 1.5 mg/kg AC004792 | 0.346 | 0.042 | 0.048 | 0.285 | 0.064 | 0.082 |
| 7. 0.75 mg/kg AC004798 | 0.351 | 0.082 | 0.108 | 0.327 | 0.079 | 0.105 |
| 8. 1.5 mg/kg AC004798 | 0.264 | 0.053 | 0.066 | 0.240 | 0.061 | 0.082 |
| 9. 1.5 mg/kg AC005485 | 0.302 | 0.075 | 0.100 | 0.282 | 0.049 | 0.060 |
| 10. 1.5 mg/kg AC005487 | 0.389 | 0.060 | 0.071 | 0.442 | 0.080 | 0.097 |
| 11. 1.5 mg/kg AC005488 | 0.242 | 0.100 | 0.171 | 0.301 | 0.099 | 0.148 |
| 12. 1.5 mg/kg AC006262 | 0.136 | 0.031 | 0.041 | 0.265 | 0.065 | 0.086 |

In the thoracic spinal cord, right cerebellum, right cortex, and right striatum, Groups 2-12 showed reduction in mAR out to at least Day 15. In the thoracic spinal cord right cerebellum, right cortex, and right striatum, a dose-response was observed for AC004791, AC004792, and AC004798.

Example 16. In Vivo Knockdown of AR in Transgenic Tg B-hTfr1 Mice

AR RNAi agents were evaluated in vivo in mouse. On Day 1 and Day 2, five (n=5) female B-hTFR1 mice were administered, via subcutaneous (SC) injection, either saline or AR RNAi agents (formulated in saline at 1.5 mg/kg animal body weight), at dose concentration 0.15 mg/mL and 10 mL/kg dose volume. Dosing was in accordance with Table 23 below.

TABLE 23

Dosing groups for the mice of Example 16.

| Group ID | Dosing Route | # Animals (n=) |
|---|---|---|
| 1. PBS | Day 1 and Day 2: SC Injection | n = 5 |
| 2. 1.5 mg/kg AC006372 | Day 1 and Day 2: SC Injection | n = 5 |
| 3. 1.5 mg/kg AC011951 | Day 1 and Day 2: SC Injection | n = 5 |

B-hTFR1 mice, also known as C57BL/6-Tfrc$^{tm1(TFRC)Bcgen}$/Bcgen mice (Biocytogen), have the exons 4-19 of mouse Tfr1 gene that encode the extracellular region replaced by human TFR1 exons 4-19.

Each of the AR RNAi agents included modified nucleotides that were conjugated at the 5' terminal end of the sense strand to a targeting ligand that included an antigen binding moiety having the modified sequences as set forth in the duplex structures herein.

On Day 15, the mice were euthanized. From the mice, CNS and muscle tissues were harvested and collected for analysis. mAR mRNA transcript expression was analyzed via qPCR, with mPPIA as endogenous gene, normalized to Group 1 mice dosed with saline. The mAR expression data is shown in the following Table 24.

TABLE 24

Relative expression of mAR in mice CNS and muscle tissues, of Example 16.

| | Day 15 | | | | | |
|---|---|---|---|---|---|---|
| | Cerebellum | | | Cortex | | |
| Group ID | Rel. Exp. mAR | Error (Low) | Error (High) | Rel. Exp. mAR | Error (Low) | Error (High) |
| 1. PBS | 1.000 | 0.211 | 0.267 | 1.000 | 0.173 | 0.209 |
| 2. 1.5 mg/kg AC006372 | 0.202 | 0.037 | 0.045 | 0.293 | 0.032 | 0.036 |
| 3. 1.5 mg/kg AC011951 | 0.157 | 0.042 | 0.058 | 0.236 | 0.059 | 0.079 |
| | Triceps | | | Gastrocnemius | | |
| Group ID | Rel. Exp. mAR | Error (Low) | Error (High) | Rel. Exp. mAR | Error (Low) | Error (High) |
| 1. PBS | 1.000 | 0.127 | 0.145 | 1.000 | 0.135 | 0.156 |
| 2. 1.5 mg/kg AC006372 | 0.221 | 0.039 | 0.048 | 0.218 | 0.030 | 0.034 |
| 3. 1.5 mg/kg AC011951 | 0.263 | 0.055 | 0.069 | 0.216 | 0.032 | 0.037 |
| | Thoracic Spinal Cord | | | Right Striatum | | |
| Group ID | Rel. Exp. mAR | Error (Low) | Error (High) | Rel. Exp. mAR | Error (Low) | Error (High) |
| 1. PBS | 1.000 | 0.209 | 0.264 | 1.000 | 0.313 | 0.456 |
| 2. 1.5 mg/kg AC006372 | 0.202 | 0.043 | 0.055 | 0.409 | 0.066 | 0.078 |
| 3. 1.5 mg/kg AC011951 | 0.182 | 0.057 | 0.083 | 0.377 | 0.093 | 0.124 |

In the cerebellum, cortex, triceps, gastrocnemius, thoracic spinal cord, and right striatum, Groups 2 and 3 showed reduction in mAR out to at least Day 15. Most notably, two doses of 1.5 mg/kg AC011951 achieved ~84% inhibition (0.157) in the cerebellum.

Example 17. In Vivo Knockdown of AR in Transgenic Tg B-hTfr1 Mice

AR RNAi agents were evaluated in vivo in mouse. On Day 1, Day 1 & 2, or Day 1 &2 & 3 & 4, five (n=5) female B-hTFR1 mice were administered, via subcutaneous (SC) injection, either saline or AR RNAi agents (formulated in saline at 0.75, 1.5, 3.0, and 12.0 mg/kg animal body weight), at total dosing volume of 250 μL/25 g. Dosing was in accordance with Table 25 below.

TABLE 25

| Dosing groups for the mice of Example 17. | | |
|---|---|---|
| Group ID | Dosing Route | # Animals (n=) |
| 1. PBS | Day 1: SC Injection | n = 5 |
| 2. 0.75 mg/kg AC006372 | Day 1: SC Injection | n = 5 |
| 3. 1.5 mg/kg AC006372 | Day 1: SC Injection | n = 5 |
| 4. 3.0 mg/kg AC006372 | Day 1: SC Injection | n = 5 |
| 5. 6.0 mg/kg AC006372 | Day 1: SC Injection | n = 5 |
| 6. 12.0 mg/kg AC006372 | Day 1: SC Injection | n = 5 |
| 7. 1.5 mg/kg AC006372 | Day 1 and Day 2: SC Injection | n = 5 |
| 8. 3.0 mg/kg AC006372 | Day 1 and Day 2: SC Injection | n = 5 |
| 9. 1.5 mg/kg AC006372 | Day 1, Day 2, Day 3, and Day 4: SC Injection | n = 5 |
| 10. 3.0 mg/kg AC006372 | Day 1, Day 2, Day 3, and Day 4: SC Injection | n = 5 |

B-hTFR1 mice, also known as C5BL/6-Tfrc$^{tm1(TFRC_Bc_gen)}$/Bcgen mice (Biocytogen), have the exons 4-19 of mouse Tfr1 gene that encode the extracellular region replaced by human TFR1 exons 4-19.

Each of the AR RNAi agents included modified nucleotides that were conjugated at the 5' terminal end of the sense strand to a targeting ligand that included an antigen binding moiety having the modified sequences as set forth in the duplex structures herein.

On Day 15, the mice were euthanized. From the mice, thoracic spinal cord and cerebellum, striatum, and cortex were harvested and collected for analysis. mAR mRNA transcript expression was analyzed via qPCR, with mPPIA as endogenous gene, normalized to Group 1 mice dosed with saline. The mAR expression data is shown in the following Table 26.

TABLE 26

Relative expression of mAR in mice thoracic spinal cord, cerebellum, striatum, and cortex, of Example 17.

| | Day 15 | | | | | |
|---|---|---|---|---|---|---|
| | Thoracic Spinal Cord | | | Cerebellum | | |
| Group ID | Rel. Exp. mAR | Error (Low) | Error (High) | Rel. Exp. mAR | Error (Low) | Error (High) |
| 1. PBS | 1.000 | 0.143 | 0.166 | 1.000 | 0.242 | 0.320 |
| 2. 0.75 mg/kg AC006372 | 0.598 | 0.144 | 0.189 | 0.414 | 0.124 | 0.177 |
| 3. 1.5 mg/kg AC006372 | 0.490 | 0.102 | 0.128 | 0.358 | 0.055 | 0.065 |
| 4. 3.0 mg/kg AC006372 | 0.454 | 0.190 | 0.326 | 0.332 | 0.154 | 0.288 |
| 5. 6.0 mg/kg AC006372 | 0.339 | 0.083 | 0.110 | 0.282 | 0.092 | 0.137 |
| 6. 12.0 mg/kg AC006372 | 0.343 | 0.077 | 0.100 | 0.199 | 0.030 | 0.036 |
| 7. 2 × 1.5 mg/kg AC006372 | 0.359 | 0.041 | 0.047 | 0.197 | 0.023 | 0.026 |
| 8. 2 × 3.0 mg/kg AC006372 | 0.350 | 0.037 | 0.041 | 0.193 | 0.031 | 0.038 |
| 9. 4 × 1.5 mg/kg AC006372 | 0.329 | 0.031 | 0.035 | 0.169 | 0.033 | 0.041 |
| 10. 4 × 3.0 mg/kg AC006372 | 0.229 | 0.025 | 0.028 | 0.153 | 0.018 | 0.020 |

| | Cortex | | | Striatum | | |
|---|---|---|---|---|---|---|
| Group ID | Rel. Exp. mAR | Error (Low) | Error (High) | Rel. Exp. mAR | Error (Low) | Error (High) |
| 1. PBS | 1.000 | 0.265 | 0.361 | 1.000 | 0.199 | 0.249 |
| 2. 0.75 mg/kg AC006372 | 0.809 | 0.164 | 0.206 | 0.837 | 0.174 | 0.219 |
| 3. 1.5 mg/kg AC006372 | 0.647 | 0.066 | 0.074 | 0.610 | 0.097 | 0.116 |
| 4. 3.0 mg/kg AC006372 | 0.588 | 0.229 | 0.374 | 0.527 | 0.177 | 0.267 |
| 5. 6.0 mg/kg AC006372 | 0.376 | 0.074 | 0.092 | 0.429 | 0.057 | 0.066 |
| 6. 12.0 mg/kg AC006372 | 0.370 | 0.038 | 0.042 | 0.402 | 0.049 | 0.055 |
| 7. 2 × 1.5 mg/kg AC006372 | 0.406 | 0.039 | 0.043 | 0.282 | 0.066 | 0.087 |
| 8. 2 × 3.0 mg/kg AC006372 | 0.366 | 0.051 | 0.059 | 0.293 | 0.044 | 0.051 |
| 9. 4 × 1.5 mg/kg AC006372 | 0.265 | 0.026 | 0.029 | 0.313 | 0.075 | 0.099 |
| 10. 4 × 3.0 mg/kg AC006372 | 0.279 | 0.034 | 0.039 | 0.183 | 0.020 | 0.023 |

| | Mid-Brain | | |
|---|---|---|---|
| Group ID | Rel. Exp. mAR | Error (Low) | Error (High) |
| 1. PBS | 1.000 | 0.277 | 0.383 |
| 2. 0.75 mg/kg AC006372 | 0.815 | 0.298 | 0.470 |
| 3. 1.5 mg/kg AC006372 | 0.520 | 0.085 | 0.102 |
| 4. 3.0 mg/kg AC006372 | 0.749 | 0.261 | 0.399 |
| 5. 6.0 mg/kg AC006372 | 0.513 | 0.103 | 0.129 |
| 6. 12.0 mg/kg AC006372 | 0.527 | 0.096 | 0.117 |

TABLE 26-continued

| Relative expression of mAR in mice thoracic spinal cord, cerebellum, striatum, and cortex, of Example 17. | | | |
|---|---|---|---|
| 7. 2 × 1.5 mg/kg AC006372 | 0.383 | 0.075 | 0.093 |
| 8. 2 × 3.0 mg/kg AC006372 | 0.375 | 0.081 | 0.103 |
| 9. 4 × 1.5 mg/kg AC006372 | 0.309 | 0.040 | 0.046 |
| 10. 4 × 3.0 mg/kg AC006372 | 0.227 | 0.047 | 0.060 |

In the thoracic spinal cord, cerebellum, cortex, striatum, and mid-brain, Groups 2-10 showed reduction in mAR out to at least Day 15. Most notably, four doses of 3.0 mg/kg AC006372 achieved ~85% inhibition (0.153) in the cerebellum. In the thoracic spinal cord and cerebellum, a dose-response was observed for the single dose, two doses, and four doses of AC006372. In the cortex, a dose-response was observed for the single dose and two doses of AC006372. In the striatum, a dose-response was observed for the single dose and the four doses of AC006372. In the mid-brain, a dose-response was observed for the two doses and four doses of AC006372.

Example 18. In Vivo Knockdown of AR in Transgenic Tg B-hTfr1 Mice

AR RNAi agents were evaluated in vivo in mouse. On Day 1 and Day 2, five (n=5) female B-hTFR1 mice were administered, via subcutaneous (SC) injection, either saline or AR RNAi agents (formulated in saline at 1.5 mg/kg animal body weight), at total dosing volume of 250 μL/25 g. Dosing was in accordance with Table 27 below.

TABLE 27

Dosing groups for the mice of Example 18.

| Group ID | Dosing Route | # Animals (n=) |
|---|---|---|
| 1. Saline | Day 1 and Day 2: SC Injection | n = 5 |
| 2. 1.5 mg/kg AC006372 | Day 1 and Day 2: SC Injection | n = 5 |
| 3. 1.5 mg/kg AC006894 | Day 1 and Day 2: SC Injection | n = 5 |
| 4. 1.5 mg/kg AC006895 | Day 1 and Day 2: SC Injection | n = 5 |
| 5. 1.5 mg/kg AC006898 | Day 1 and Day 2: SC Injection | n = 5 |
| 6. 1.5 mg/kg AC006896 | Day 1 and Day 2: SC Injection | n = 5 |
| 7. 1.5 mg/kg AC006597 | Day 1 and Day 2: SC Injection | n = 5 |

B-hTFR1 mice, also known as C57BL/6-Tfrc$^{tm1(TFRC)}_{Bcgen}$/Bcgen mice (B3iocytogen), have the exons 4-19 of mouse Tfr1 gene that encode the extracellular region replaced by human TFR1exons 4-19.

Each of the AR RNAi agents included modified nucleotides that were conjugated at the 5' terminal end of the sense strand to a targeting ligand that. included an antigen binding moiety having the modified sequences as set forth in the duplex structures herein.

On Day 15, the mice were euthanized. From the mice, thoracic spinal cord and cerebellum, striatum, and cortex were harvested and collected for analysis. mAR mRNA transcript expression was analyzed via qPCR, with mPPIA as endogenous gene, normalized to Group 1 mice dosed with saline. The mAR expression data. is shown in the following Table 28.

TABLE 28

Relative expression of mAR in mice thoracic spinal cord, cerebellum, striatum, and cortex, of Example 18.

| | Day 15 | | | | | |
|---|---|---|---|---|---|---|
| | Thoracic Spinal Cord | | | Cerebellum | | |
| Group ID | Rel. Exp. mAR | Error (Low) | Error (High) | Rel. Exp. mAR | Error (Low) | Error (High) |
| 1. Saline | 1.000 | 0.156 | 0.185 | 1.000 | 0.163 | 0.195 |
| 2. 1.5 mg/kg AC006372 | 0.431 | 0.045 | 0.050 | 0.355 | 0.075 | 0.095 |
| 3. 1.5 mg/kg AC006894 | 0.432 | 0.080 | 0.098 | 0.283 | 0.037 | 0.043 |
| 4. 1.5 mg/kg AC006895 | 0.327 | 0.047 | 0.054 | 0.237 | 0.031 | 0.036 |
| 5. 1.5 mg/kg AC006898 | 0.356 | 0.063 | 0.077 | 0.276 | 0.029 | 0.032 |
| 6. 1.5 mg/kg AC006896 | 0.411 | 0.089 | 0.113 | 0.300 | 0.049 | 0.058 |
| 7. 1.5 mg/kg AC006597 | 0.241 | 0.070 | 0.099 | 0.512 | 0.037 | 0.039 |
| | Cortex | | | Striatum | | |
| Group ID | Rel. Exp. mAR | Error (Low) | Error (High) | Rel. Exp. mAR | Error (Low) | Error (High) |
| 1. Saline | 1.000 | 0.221 | 0.284 | 1.000 | 0.156 | 0.185 |
| 2. 1.5 mg/kg AC006372 | 0.296 | 0.048 | 0.058 | 0.391 | 0.077 | 0.095 |

TABLE 28-continued

Relative expression of mAR in mice thoracic spinal cord, cerebellum, striatum, and cortex, of Example 18.

| | | | | | | |
|---|---|---|---|---|---|---|
| 3. 1.5 mg/kg AC006894 | 0.287 | 0.056 | 0.070 | 0.483 | 0.110 | 0.142 |
| 4. 1.5 mg/kg AC006895 | 0.266 | 0.078 | 0.110 | 0.350 | 0.036 | 0.040 |
| 5. 1.5 mg/kg AC006898 | 0.331 | 0.070 | 0.089 | 0.455 | 0.128 | 0.178 |
| 6. 1.5 mg/kg AC006896 | 0.324 | 0.072 | 0.093 | 0.338 | 0.058 | 0.069 |
| 7. 1.5 mg/kg AC006597 | 0.368 | 0.038 | 0.043 | 0.539 | 0.100 | 0.123 |

In the thoracic spinal cord, cerebellum, cortex, and striatum, Groups 2-7 showed reduction in mAR out to at least Day 15.

Example 19. In Vivo Knockdown of AR in Transgenic Tg B-hTfr1 Mice

AR RNAi agents were evaluated in vivo in mouse. On Day 1, Day 2, and Day 3, four (n=4) female B-hTFR1 mice were administered, via subcutaneous (SC) injection, either saline or AR RNAi agents (formulated in saline at 3.0 mg/kg animal body weight), at total dosing volume of 250 μL/25 g. Dosing was in accordance with Table 29 below.

TABLE 29

Dosing groups for the mice of Example 19.

| Group ID | Dosing Route | # Animals (n=) | Harvest Day |
|---|---|---|---|
| 1. PBS | Day 1, 2, and 3: SC Injection | n = 4 | Day 59 |
| 2. 3.0 mg/kg AC006448 | Day 1, 2, and 3: SC Injection | n = 4 | Day 4 |
| 3. 3.0 mg/kg AC006448 | Day 1, 2, and 3: SC Injection | n = 4 | Day 10 |
| 4. 3.0 mg/kg AC006448 | Day 1, 2, and 3: SC Injection | n = 4 | Day 17 |
| 5. 3.0 mg/kg AC006448 | Day 1, 2, and 3: SC Injection | n = 4 | Day 31 |
| 6. 3.0 mg/kg AC006448 | Day 1, 2, and 3: SC Injection | n = 4 | Day 45 |
| 7. 3.0 mg/kg AC006448 | Day 1, 2, and 3: SC Injection | n = 4 | Day 59 |

TABLE 29-continued

Dosing groups for the mice of Example 19.

| Group ID | Dosing Route | # Animals (n=) | Harvest Day |
|---|---|---|---|
| 8. PBS | Day 1, 2, and 3: SC Injection | n = 4 | Day 122 |
| 9. 3.0 mg/kg AC006448 | Day 1, 2, and 3: SC Injection | n = 4 | Day 80 |
| 10. 3.0 mg/kg AC006448 | Day 1, 2, and 3: SC Injection | n = 4 | Day 100 |
| 11. 3.0 mg/kg AC006448 | Day 1, 2, and 3: SC Injection | n = 4 | Day 122 |

B-hTFR1 mice, also known as C57BL/6-Tfrc$^{tm1(TFRC)}$ $_{Bcgen}$/Bcgen mice (Biocytogen), have the exons 4-19 of mouse Tfr1 gene that encode the extracellular region replaced by human TFR1 exons 4-19.

Each of the AR RNAi agents included modified nucleotides that were conjugated at the 5' terminal end of the sense strand to a targeting ligand that included an antigen binding moiety having the modified sequences as set forth in the duplex structures herein.

On Day 4, 10, 17, 31, 45, 59, 80, 100, or 122, the mice were euthanized in accordance with Table 58 above. From the mice, thoracic spinal cord and cerebellum, striatum, and cortex were harvested and collected for analysis. mAR mRNA transcript expression was analyzed via qPCR, with mPPIA as endogenous gene; Groups 3-7 were normalized to Group 1 mice dosed with saline, Groups 9-11 were normalized to Group 8 mice dosed with saline. The mAR expression data is shown in the following Table 30 and Table 31.

TABLE 30

Relative expression of mAR in mice thoracic spinal cord, cerebellum, striatum, and cortex, of Example 19.

| | | Thoracic Spinal Cord | | | Cerebellum | | |
|---|---|---|---|---|---|---|---|
| Group ID | Harvest Day | Rel. mAR | Error (Low) | Error (High) | Rel. mAR | Error (Low) | Error (High) |
| 1. PBS | Day 59 | 1.000 | 0.161 | 0.191 | 1.000 | 0.352 | 0.543 |
| 3. 3.0 mg/kg AC006448 | Day 10 | 0.325 | 0.132 | 0.223 | 0.171 | 0.024 | 0.028 |
| 4. 3.0 mg/kg AC006448 | Day 17 | 0.278 | 0.122 | 0.218 | 0.195 | 0.065 | 0.097 |
| 5. 3.0 mg/kg AC006448 | Day 31 | 0.607 | 0.134 | 0.171 | 0.397 | 0.102 | 0.137 |
| 6. 3.0 mg/kg AC006448 | Day 45 | 0.417 | 0.107 | 0.144 | 0.225 | 0.045 | 0.057 |
| 7. 3.0 mg/kg AC006448 | Day 59 | 0.344 | 0.135 | 0.223 | 0.147 | 0.025 | 0.030 |

| | | Left Cortex | | | Striatum | | |
|---|---|---|---|---|---|---|---|
| Group ID | Harvest Day | Rel. mAR | Error (Low) | Error (High) | Rel. mAR | Error (Low) | Error (High) |
| 1. PBS | Day 59 | 1.000 | 0.130 | 0.149 | 1.000 | 0.190 | 0.234 |
| 3. 3.0 mg/kg AC006448 | Day 10 | 0.289 | 0.058 | 0.072 | 0.257 | 0.042 | 0.051 |
| 4. 3.0 mg/kg AC006448 | Day 17 | 0.283 | 0.065 | 0.084 | 0.283 | 0.045 | 0.054 |
| 5. 3.0 mg/kg AC006448 | Day 31 | 0.253 | 0.056 | 0.072 | 0.422 | 0.084 | 0.105 |

TABLE 30-continued

Relative expression of mAR in mice thoracic spinal cord, cerebellum, striatum, and cortex, of Example 19.

| | | | | | | | |
|---|---|---|---|---|---|---|---|
| 6. 3.0 mg/kg AC006448 | Day 45 | 0.312 | 0.082 | 0.112 | 0.324 | 0.068 | 0.085 |
| 7. 3.0 mg/kg AC006448 | Day 59 | 0.255 | 0.050 | 0.063 | 0.300 | 0.085 | 0.119 |

| | | Brain Stem | | |
|---|---|---|---|---|
| Group ID | Harvest Day | Rel. mAR | Error (Low) | Error (High) |
| 1. PBS | Day 59 | 1.000 | 0.287 | 0.402 |
| 3. 3.0 mg/kg AC006448 | Day 10 | 0.172 | 0.054 | 0.078 |
| 4. 3.0 mg/kg AC006448 | Day 17 | 0.162 | 0.050 | 0.072 |
| 5. 3.0 mg/kg AC006448 | Day 31 | 0.272 | 0.042 | 0.049 |
| 6. 3.0 mg/kg AC006448 | Day 45 | 0.240 | 0.079 | 0.119 |
| 7. 3.0 mg/kg AC006448 | Day 59 | 0.356 | 0.064 | 0.078 |

In the thoracic spinal cord, cerebellum, left cortex, striatum, and brain stem, Groups 3-7 showed reduction in mAR out to at least Day 59. Most notably, three doses of 3.0 mg/kg AC006448 achieved ~85% inhibition (0.147) in the cerebellum at Day 59.

TABLE 31

Relative expression of mAR in mice thoracic spinal cord, cerebellum, striatum, and cortex, of Example 19.

| | | Thoracic Spinal Cord | | | Cerebellum | | |
|---|---|---|---|---|---|---|---|
| Group ID | Harvest Day | Rel. mAR | Error (Low) | Error (High) | Rel. mAR | Error (Low) | Error (High) |
| 8. PBS | Day 122 | 1.000 | 0.177 | 0.215 | 1.000 | 0.069 | 0.074 |
| 9. 3.0 mg/kg AC006448 | Day 80 | 0.520 | 0.033 | 0.036 | 0.336 | 0.079 | 0.103 |
| 10. 3.0 mg/kg AC006448 | Day 100 | 0.652 | 0.194 | 0.275 | 0.580 | 0.060 | 0.066 |
| 11. 3.0 mg/kg AC006448 | Day 122 | 0.686 | 0.160 | 0.209 | 0.800 | 0.123 | 0.145 |

| | | Left Cortex | | | Striatum | | |
|---|---|---|---|---|---|---|---|
| Group ID | Harvest Day | Rel. mAR | Error (Low) | Error (High) | Rel. mAR | Error (Low) | Error (High) |
| 8. PBS | Day 122 | 1.000 | 0.208 | 0.263 | 1.000 | 0.202 | 0.254 |
| 9. 3.0 mg/kg AC006448 | Day 80 | 0.539 | 0.077 | 0.089 | 0.567 | 0.091 | 0.108 |
| 10. 3.0 mg/kg AC006448 | Day 100 | 0.822 | 0.068 | 0.074 | 0.570 | 0.113 | 0.141 |
| 11. 3.0 mg/kg AC006448 | Day 122 | 0.971 | 0.060 | 0.064 | 0.612 | 0.221 | 0.346 |

| | | Brain Stem | | |
|---|---|---|---|---|
| Group ID | Harvest Day | Rel. mAR | Error (Low) | Error (High) |
| 8. PBS | Day 122 | 1.000 | 0.217 | 0.278 |
| 9. 3.0 mg/kg AC006448 | Day 80 | 0.615 | 0.047 | 0.051 |
| 10. 3.0 mg/kg AC006448 | Day 100 | 0.897 | 0.120 | 0.138 |
| 11. 3.0 mg/kg AC006448 | Day 122 | 0.942 | 0.153 | 0.182 |

In the thoracic spinal cord, cerebellum, and striatum, Groups 9-11 showed reduction in mAR out to at least Day 122. Most notably, three doses of 3.0 mg/kg AC006448 achieved ~39% inhibition (0.612) in the striatum at Day 122.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An antibody that binds a transferrin receptor (TfR1), the antibody comprising a heavy chain that comprises a heavy chain variable region (VH) and a light chain that comprises a light chain variable region (VL);

wherein the VH comprises:

- a heavy chain complementarity determining region 1 (HC CDR1) comprising the amino acid sequence GFTFTSYWMH (SEQ ID NO: 16);
- a heavy chain complementarity determining region 2 (HC CDR2) comprising the amino acid sequence EINPINGRTNYIEKFKS (SEQ ID NO: 19); and
- a heavy chain complementarity determining region 3 (HC CDR3) comprising the amino acid sequence GTRAYHY (SEQ ID NO: 24); and wherein the VL comprises:

- a light chain complementarity determining region 1 (LC CDR1) comprising the amino acid sequence RASDKLYSNLA (SEQ ID NO: 4);
- a light chain complementarity determining region 2 (LC CDR2) comprising the amino acid sequence DATLLAS (SEQ ID NO: 11); and
- a light chain complementarity determining region 3 (LC CDR3) comprising the amino acid sequence QHFWGTPLT (SEQ ID NO: 13).

2. The antibody of claim 1, wherein the antibody comprises a VH having the amino acid sequence EVOLVESGGGLVQPGGSLRLSCATSGFTFTSYWMHWVRQAPGKGLEWVAEINPTNGRT NYIEKFKSRITLSVDKSKSTVYLQMNSLRAEDTAVYYCARGTRAYHYWGQGTLVTVSS (SEQ ID NO: 59); and wherein the antibody comprises a VL having the amino acid sequence DIQLTQSPS SLSASVGDRVTITCRASDKLYSNLAWYQQKPGKAPKLLIYDATLLASGVPSR FSGSGSGTDYTLTISSLQPEDFATYYCQHFWGTPLTFGQGTKVEIK (SEQ ID NO: 60).

3. The antibody of claim 1, wherein the antibody is a full-length antibody, an antigen binding fragment thereof, or a single chain fragment variable (scFv) antibody.

4. The antibody of claim 1, wherein the antibody is a Fab molecule; wherein the heavy chain comprises the VH and a CH1 heavy chain constant region fragment; and wherein the light chain comprises the VL and a light chain constant region (CL).

5. The antibody of claim 4, wherein the CH1 comprises the amino acid sequence of (SEQ ID NO: 34)
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRV
EPKSCDKTH;

and wherein the CL comprises the amino acid sequence of (SEQ ID NO: 29)
RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC.

6. The antibody of claim 4, wherein:

(a) the heavy chain comprises the amino acid sequence of SEQ ID NO: 61 and the light chain comprises the amino acid sequence of SEQ ID NO: 62; or (b) the heavy chain comprises the amino acid sequence of SEQ ID NO: 45 and the light chain comprises the amino acid sequence of SEQ ID NO: 46.

7. The antibody of claim 1, wherein the antibody comprises an Fc fragment.

8. A conjugate comprising an antibody that binds a transferrin receptor (TfR1) (anti-TfR1 antibody) and an oligonucleotide-based agent, wherein the anti-TfR1 antibody is set forth in claim 1.

9. The conjugate of claim 8, wherein the oligonucleotide-based agent is directly conjugated to the anti-TfR1 antibody via a covalent bond or a non-covalent bond.

10. The conjugate of claim 8, wherein the oligonucleotide-based agent is conjugated to the anti-TfR1 antibody via a linker, which optionally is a chemical linker, a peptide linker, a polymer linker, or a nucleic acid-binding polypeptide.

11. The conjugate of claim 8, wherein the oligonucleotide-based agent is an RNAi agent comprising a sense strand and an anti-sense strand, which form a double-strand.

12. The conjugate of claim 11, wherein the RNAi agent attenuates expression of a target gene selected from the group consisting of APP, Ataxin-1, Ataxin-2, Ataxin-3, Ataxin-7, androgen receptor, SOD1, Huntingtin, Chromosome 9 open reading frame 72, Leucine-rich repeat serine/threonine-protein kinase 2, complement C3, microtubule-associated protein tau, alpha-2A adrenergic receptor, sodium channel protein type 9 subunit alpha, Apolipoprotein E, alpha-synuclein, probable G-protein coupled receptor 75, RNA-binding protein FUS, GFAP, KCNT1, PRNP, MSH3, RAGE, SNC9A, SCN10A, SCN11A, SORT1, VCP, PIKFYVE, CHMP7, PDE2A, SARM1, NLRP3, GSDME, and DYRKIA.

13. The conjugate of claim 12, wherein the target gene is selected from the group consisting of APP, ATXN2, ATXN3, AR, SOD1, HTT, C9ORF72, LRRK2, C3, MAPT, ADRA2A, SCN9A, APOE, SNCA, GPR75, and FUS.

14. The conjugate of claim 11, wherein the sense strand is conjugated to the anti-TfR1 antibody, wherein the anti-TfR1 antibody is a Fab molecule.

15. A method for attenuating expression of a target gene in the brain of a subject, comprising administering to a subject in need thereof an effective amount of a conjugate or a pharmaceutical composition comprising such, wherein the conjugate comprises an anti-TfR1 antibody conjugated to an oligonucleotide-based agent, wherein the anti-TfR1 antibody is set forth in claim 1; and wherein the oligonucleotide-based agent attenuates expression of the target gene.

16. The method of claim 15, wherein the subject is a human patient having or suspected of having a central nervous system (CNS) disease.

17. The method of claim 16, wherein the CNS disease is selected from the group consisting of amyotrophic lateral sclerosis (ALS), Alzheimer's disease, Parkinson's disease, Huntington's Disease, dementia, cognitive impairment, frontotemporal dementia, Lewy body disease, cerebral amyloid angiopathy, tauopathies, spinocerebellar ataxia, Alexander's disease, Kennedy's disease, childhood epilepsy, fatal familial insomnia, prion disease, pain, multiple system atrophy, corticobasal degeneration, progressive supranuclear palsy, TDP43 proteinopathies, traumatic brain injury, Down syndrome, neuropathic pain, inherited erythromelalgia, paroxysmal extreme pain disorder, and heritable small fiber neuropathy.

18. The method of claim 16, wherein the CNS disease is Alzheimer's disease.

* * * * *

SEQUENCE LISTING

```
Sequence total quantity: 153
SEQ ID NO: 1            moltype = AA  length = 11
FEATURE                 Location/Qualifiers
source                  1..11
                        mol_type = protein
                        organism = synthetic construct
SEQUENCE: 1
RASDNLYSNL A                                                       11

SEQ ID NO: 2            moltype = AA  length = 11
FEATURE                 Location/Qualifiers
source                  1..11
                        mol_type = protein
                        organism = synthetic construct
SEQUENCE: 2
RASDGLYSNL A                                                       11
```

```
SEQ ID NO: 3            moltype = AA  length = 11
FEATURE                 Location/Qualifiers
source                  1..11
                        mol_type = protein
                        organism = synthetic construct
SEQUENCE: 3
RASDNLYRNL A                                                 11

SEQ ID NO: 4            moltype = AA  length = 11
FEATURE                 Location/Qualifiers
source                  1..11
                        mol_type = protein
                        organism = synthetic construct
SEQUENCE: 4
RASDKLYSNL A                                                 11

SEQ ID NO: 5            moltype = AA  length = 11
FEATURE                 Location/Qualifiers
source                  1..11
                        mol_type = protein
                        organism = synthetic construct
VARIANT                 5
                        note = G, K, or N
VARIANT                 8
                        note = R or S
SEQUENCE: 5
RASDXLYXNL A                                                 11

SEQ ID NO: 6            moltype = AA  length = 7
FEATURE                 Location/Qualifiers
source                  1..7
                        mol_type = protein
                        organism = synthetic construct
SEQUENCE: 6
DATNLAD                                                      7

SEQ ID NO: 7            moltype = AA  length = 7
FEATURE                 Location/Qualifiers
source                  1..7
                        mol_type = protein
                        organism = synthetic construct
SEQUENCE: 7
DATKLAS                                                      7

SEQ ID NO: 8            moltype = AA  length = 7
FEATURE                 Location/Qualifiers
source                  1..7
                        mol_type = protein
                        organism = synthetic construct
SEQUENCE: 8
DAFNLAS                                                      7

SEQ ID NO: 9            moltype = AA  length = 7
FEATURE                 Location/Qualifiers
source                  1..7
                        mol_type = protein
                        organism = synthetic construct
SEQUENCE: 9
DATRLAS                                                      7

SEQ ID NO: 10           moltype = AA  length = 7
FEATURE                 Location/Qualifiers
source                  1..7
                        mol_type = protein
                        organism = synthetic construct
SEQUENCE: 10
DAKNLAS                                                      7

SEQ ID NO: 11           moltype = AA  length = 7
FEATURE                 Location/Qualifiers
source                  1..7
                        mol_type = protein
                        organism = synthetic construct
SEQUENCE: 11
DATLLAS                                                      7

SEQ ID NO: 12           moltype = AA  length = 7
FEATURE                 Location/Qualifiers
```

-continued

```
source                 1..7
                       mol_type = protein
                       organism = synthetic construct
SEQUENCE: 12
DARNLAS                                                                   7

SEQ ID NO: 13          moltype = AA  length = 9
FEATURE                Location/Qualifiers
source                 1..9
                       mol_type = protein
                       organism = synthetic construct
SEQUENCE: 13
QHFWGTPLT                                                                 9

SEQ ID NO: 14          moltype = AA  length = 10
FEATURE                Location/Qualifiers
source                 1..10
                       mol_type = protein
                       organism = synthetic construct
SEQUENCE: 14
GYTFTSYWMH                                                                10

SEQ ID NO: 15          moltype = AA  length = 10
FEATURE                Location/Qualifiers
source                 1..10
                       mol_type = protein
                       organism = synthetic construct
SEQUENCE: 15
GYTFTSYWVH                                                                10

SEQ ID NO: 16          moltype = AA  length = 10
FEATURE                Location/Qualifiers
source                 1..10
                       mol_type = protein
                       organism = synthetic construct
SEQUENCE: 16
GFTFTSYWMH                                                                10

SEQ ID NO: 17          moltype = AA  length = 10
FEATURE                Location/Qualifiers
source                 1..10
                       mol_type = protein
                       organism = synthetic construct
SEQUENCE: 17
GYTFNSYWMH                                                                10

SEQ ID NO: 18          moltype = AA  length = 10
FEATURE                Location/Qualifiers
source                 1..10
                       mol_type = protein
                       organism = synthetic construct
SEQUENCE: 18
GYTFKSYWMH                                                                10

SEQ ID NO: 19          moltype = AA  length = 17
FEATURE                Location/Qualifiers
source                 1..17
                       mol_type = protein
                       organism = synthetic construct
SEQUENCE: 19
EINPTNGRTN YIEKFKS                                                        17

SEQ ID NO: 20          moltype = AA  length = 17
FEATURE                Location/Qualifiers
source                 1..17
                       mol_type = protein
                       organism = synthetic construct
SEQUENCE: 20
EINPTNGRVN YIEKFKS                                                        17

SEQ ID NO: 21          moltype = AA  length = 17
FEATURE                Location/Qualifiers
source                 1..17
                       mol_type = protein
                       organism = synthetic construct
SEQUENCE: 21
EINPTNGRSN YIEKFKS                                                        17

SEQ ID NO: 22          moltype = AA  length = 17
```

-continued

```
FEATURE                 Location/Qualifiers
source                  1..17
                        mol_type = protein
                        organism = synthetic construct
SEQUENCE: 22
EINPTNGRFN YIEKFKS                                              17

SEQ ID NO: 23           moltype = AA  length = 17
FEATURE                 Location/Qualifiers
source                  1..17
                        mol_type = protein
                        organism = synthetic construct
VARIANT                 9
                        note = F, S, T, or V
SEQUENCE: 23
EINPTNGRXN YIEKFKS                                              17

SEQ ID NO: 24           moltype = AA  length = 7
FEATURE                 Location/Qualifiers
source                  1..7
                        mol_type = protein
                        organism = synthetic construct
SEQUENCE: 24
GTRAYHY                                                         7

SEQ ID NO: 25           moltype = AA  length = 23
FEATURE                 Location/Qualifiers
source                  1..23
                        mol_type = protein
                        organism = synthetic construct
SEQUENCE: 25
DIQLTQSPSS LSASVGDRVT ITC                                       23

SEQ ID NO: 26           moltype = AA  length = 15
FEATURE                 Location/Qualifiers
source                  1..15
                        mol_type = protein
                        organism = synthetic construct
SEQUENCE: 26
WYQQKPGKAP KLLIY                                                15

SEQ ID NO: 27           moltype = AA  length = 32
FEATURE                 Location/Qualifiers
source                  1..32
                        mol_type = protein
                        organism = synthetic construct
SEQUENCE: 27
GVPSRFSGSG SGTDYTLTIS SLQPEDFATY YC                             32

SEQ ID NO: 28           moltype = AA  length = 10
FEATURE                 Location/Qualifiers
source                  1..10
                        mol_type = protein
                        organism = synthetic construct
SEQUENCE: 28
FGQGTKVEIK                                                      10

SEQ ID NO: 29           moltype = AA  length = 107
FEATURE                 Location/Qualifiers
source                  1..107
                        mol_type = protein
                        organism = synthetic construct
SEQUENCE: 29
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC             107

SEQ ID NO: 30           moltype = AA  length = 25
FEATURE                 Location/Qualifiers
source                  1..25
                        mol_type = protein
                        organism = synthetic construct
SEQUENCE: 30
EVQLVESGGG LVQPGGSLRL SCATS                                     25

SEQ ID NO: 31           moltype = AA  length = 14
FEATURE                 Location/Qualifiers
source                  1..14
                        mol_type = protein
                        organism = synthetic construct
```

-continued

```
SEQUENCE: 31
WVRQAPGKGL EWVA                                                    14

SEQ ID NO: 32           moltype = AA  length = 32
FEATURE                 Location/Qualifiers
source                  1..32
                        mol_type = protein
                        organism = synthetic construct
SEQUENCE: 32
RITLSVDKSK STVYLQMNSL RAEDTAVYYC AR                                32

SEQ ID NO: 33           moltype = AA  length = 11
FEATURE                 Location/Qualifiers
source                  1..11
                        mol_type = protein
                        organism = synthetic construct
SEQUENCE: 33
WGQGTLVTVS S                                                       11

SEQ ID NO: 34           moltype = AA  length = 107
FEATURE                 Location/Qualifiers
source                  1..107
                        mol_type = protein
                        organism = synthetic construct
SEQUENCE: 34
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTH                107

SEQ ID NO: 35           moltype = AA  length = 116
FEATURE                 Location/Qualifiers
source                  1..116
                        mol_type = protein
                        organism = synthetic construct
SEQUENCE: 35
EVQLVQSGAE VKKPGASVKV SCKASGYTFT SYWMHWVRQA PGQRLEWIGE INPTNGRTNY  60
IEKFKSRATL TVDKSASTAY MELSSLRSED TAVYYCARGT RAYHYWGQGT MVTVSS      116

SEQ ID NO: 36           moltype = AA  length = 107
FEATURE                 Location/Qualifiers
source                  1..107
                        mol_type = protein
                        organism = synthetic construct
SEQUENCE: 36
DIQMTQSPSS LSASVGDRVT ITCRASDNLY SNLAWYQQKP GKSPKLLVYD ATNLADGVPS  60
RFSGSGSGTD YTLTISSLQP EDFATYYCQH FWGTPLTFGQ GTKVEIK                107

SEQ ID NO: 37           moltype = AA  length = 223
FEATURE                 Location/Qualifiers
source                  1..223
                        mol_type = protein
                        organism = synthetic construct
SEQUENCE: 37
EVQLVQSGAE VKKPGASVKV SCKASGYTFT SYWMHWVRQA PGQRLEWIGE INPTNGRTNY  60
IEKFKSRATL TVDKSASTAY MELSSLRSED TAVYYCARGT RAYHYWGQGT MVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTH                    223

SEQ ID NO: 38           moltype = AA  length = 214
FEATURE                 Location/Qualifiers
source                  1..214
                        mol_type = protein
                        organism = synthetic construct
SEQUENCE: 38
DIQMTQSPSS LSASVGDRVT ITCRASDNLY SNLAWYQQKP GKSPKLLVYD ATNLADGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 39           moltype = AA  length = 116
FEATURE                 Location/Qualifiers
source                  1..116
                        mol_type = protein
                        organism = synthetic construct
SEQUENCE: 39
EVQLVESGGG LVQPGGSLRL SCATSGYTFT SYWVHWVRQA PGKGLEWVAE INPTNGRTNY  60
IEKFKSRITL SVDKSKSTVY LQMNSLRAED TAVYYCARGT RAYHYWGQGT LVTVSS      116

SEQ ID NO: 40           moltype = AA  length = 107
FEATURE                 Location/Qualifiers
```

```
source                  1..107
                        mol_type = protein
                        organism = synthetic construct
SEQUENCE: 40
DIQLTQSPSS LSASVGDRVT ITCRASDGLY SNLAWYQQKP GKAPKLLIYD ATKLASGVPS  60
RFSGSGSGTD YTLTISSLQP EDFATYYCQH FWGTPLTFGQ GTKVEIK               107

SEQ ID NO: 41           moltype = AA  length = 223
FEATURE                 Location/Qualifiers
source                  1..223
                        mol_type = protein
                        organism = synthetic construct
SEQUENCE: 41
EVQLVESGGG LVQPGGSLRL SCATSGYTFT SYWVHWVRQA PGKGLEWVAE INPTNGRTNY  60
IEKFKSRITL SVDKSKSTVY LQMNSLRAED TAVYYCARGT RAYHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTH                   223

SEQ ID NO: 42           moltype = AA  length = 214
FEATURE                 Location/Qualifiers
source                  1..214
                        mol_type = protein
                        organism = synthetic construct
SEQUENCE: 42
DIQLTQSPSS LSASVGDRVT ITCRASDGLY SNLAWYQQKP GKAPKLLIYD ATKLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 43           moltype = AA  length = 116
FEATURE                 Location/Qualifiers
source                  1..116
                        mol_type = protein
                        organism = synthetic construct
SEQUENCE: 43
EVQLVESGGG LVQPGGSLRL SCATSGYTFT SYWMHWVRQA PGKGLEWVAE INPTNGRVNY  60
IEKFKSRITL SVDKSKSTVY LQMNSLRAED TAVYYCARGT RAYHYWGQGT LVTVSS      116

SEQ ID NO: 44           moltype = AA  length = 107
FEATURE                 Location/Qualifiers
source                  1..107
                        mol_type = protein
                        organism = synthetic construct
SEQUENCE: 44
DIQLTQSPSS LSASVGDRVT ITCRASDGLY SNLAWYQQKP GKAPKLLIYD ATKLASGVPS  60
RFSGSGSGTD YTLTISSLQP EDFATYYCQH FWGTPLTFGQ GTKVEIK               107

SEQ ID NO: 45           moltype = AA  length = 223
FEATURE                 Location/Qualifiers
source                  1..223
                        mol_type = protein
                        organism = synthetic construct
SEQUENCE: 45
EVQLVESGGG LVQPGGSLRL SCATSGYTFT SYWMHWVRQA PGKGLEWVAE INPTNGRVNY  60
IEKFKSRITL SVDKSKSTVY LQMNSLRAED TAVYYCARGT RAYHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTH                   223

SEQ ID NO: 46           moltype = AA  length = 214
FEATURE                 Location/Qualifiers
source                  1..214
                        mol_type = protein
                        organism = synthetic construct
SEQUENCE: 46
DIQLTQSPSS LSASVGDRVT ITCRASDGLY SNLAWYQQKP GKAPKLLIYD ATKLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 47           moltype = AA  length = 107
FEATURE                 Location/Qualifiers
source                  1..107
                        mol_type = protein
                        organism = synthetic construct
SEQUENCE: 47
DIQLTQSPSS LSASVGDRVT ITCRASDGLY SNLAWYQQKP GKAPKLLIYD AFNLASGVPS  60
RFSGSGSGTD YTLTISSLQP EDFATYYCQH FWGTPLTFGQ GTKVEIK               107

SEQ ID NO: 48           moltype = AA  length = 214
```

```
FEATURE                 Location/Qualifiers
source                  1..214
                        mol_type = protein
                        organism = synthetic construct
SEQUENCE: 48
DIQLTQSPSS LSASVGDRVT ITCRASDGLY SNLAWYQQKP GKAPKLLIYD AFNLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 49           moltype = AA  length = 107
FEATURE                 Location/Qualifiers
source                  1..107
                        mol_type = protein
                        organism = synthetic construct
SEQUENCE: 49
DIQLTQSPSS LSASVGDRVT ITCRASDGLY SNLAWYQQKP GKAPKLLIYD ATRLASGVPS  60
RFSGSGSGTD YTLTISSLQP EDFATYYCQH FWGTPLTFGQ GTKVEIK                107

SEQ ID NO: 50           moltype = AA  length = 214
FEATURE                 Location/Qualifiers
source                  1..214
                        mol_type = protein
                        organism = synthetic construct
SEQUENCE: 50
DIQLTQSPSS LSASVGDRVT ITCRASDGLY SNLAWYQQKP GKAPKLLIYD ATRLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 51           moltype = AA  length = 107
FEATURE                 Location/Qualifiers
source                  1..107
                        mol_type = protein
                        organism = synthetic construct
SEQUENCE: 51
DIQLTQSPSS LSASVGDRVT ITCRASDGLY SNLAWYQQKP GKAPKLLIYD AKNLASGVPS  60
RFSGSGSGTD YTLTISSLQP EDFATYYCQH FWGTPLTFGQ GTKVEIK                107

SEQ ID NO: 52           moltype = AA  length = 214
FEATURE                 Location/Qualifiers
source                  1..214
                        mol_type = protein
                        organism = synthetic construct
SEQUENCE: 52
DIQLTQSPSS LSASVGDRVT ITCRASDGLY SNLAWYQQKP GKAPKLLIYD AKNLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 53           moltype = AA  length = 116
FEATURE                 Location/Qualifiers
source                  1..116
                        mol_type = protein
                        organism = synthetic construct
SEQUENCE: 53
EVQLVESGGG LVQPGGSLRL SCATSGYTFT SYWVHWVRQA PGKGLEWVAE INPTNGRSNY  60
IEKFKSRITL SVDKSKSTVY LQMNSLRAED TAVYYCARGT RAYHYWGQGT LVTVSS      116

SEQ ID NO: 54           moltype = AA  length = 107
FEATURE                 Location/Qualifiers
source                  1..107
                        mol_type = protein
                        organism = synthetic construct
SEQUENCE: 54
DIQLTQSPSS LSASVGDRVT ITCRASDNLY RNLAWYQQKP GKAPKLLIYD ATKLASGVPS  60
RFSGSGSGTD YTLTISSLQP EDFATYYCQH FWGTPLTFGQ GTKVEIK                107

SEQ ID NO: 55           moltype = AA  length = 223
FEATURE                 Location/Qualifiers
source                  1..223
                        mol_type = protein
                        organism = synthetic construct
SEQUENCE: 55
EVQLVESGGG LVQPGGSLRL SCATSGYTFT SYWVHWVRQA PGKGLEWVAE INPTNGRSNY  60
IEKFKSRITL SVDKSKSTVY LQMNSLRAED TAVYYCARGT RAYHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTH                    223
```

-continued

```
SEQ ID NO: 56          moltype = AA  length = 214
FEATURE                Location/Qualifiers
source                 1..214
                       mol_type = protein
                       organism = synthetic construct
SEQUENCE: 56
DIQLTQSPSS LSASVGDRVT ITCRASDNLY RNLAWYQQKP GKAPKLLIYD ATKLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 57          moltype = AA  length = 116
FEATURE                Location/Qualifiers
source                 1..116
                       mol_type = protein
                       organism = synthetic construct
SEQUENCE: 57
EVQLVESGGG LVQPGGSLRL SCATSGYTFT SYWVHWVRQA PGKGLEWVAE INPTNGRVNY  60
IEKFKSRITL SVDKSKSTVY LQMNSLRAED TAVYYCARGT RAYHYWGQGT LVTVSS      116

SEQ ID NO: 58          moltype = AA  length = 223
FEATURE                Location/Qualifiers
source                 1..223
                       mol_type = protein
                       organism = synthetic construct
SEQUENCE: 58
EVQLVESGGG LVQPGGSLRL SCATSGYTFT SYWVHWVRQA PGKGLEWVAE INPTNGRVNY  60
IEKFKSRITL SVDKSKSTVY LQMNSLRAED TAVYYCARGT RAYHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTH                    223

SEQ ID NO: 59          moltype = AA  length = 116
FEATURE                Location/Qualifiers
source                 1..116
                       mol_type = protein
                       organism = synthetic construct
SEQUENCE: 59
EVQLVESGGG LVQPGGSLRL SCATSGFTFT SYWMHWVRQA PGKGLEWVAE INPTNGRTNY  60
IEKFKSRITL SVDKSKSTVY LQMNSLRAED TAVYYCARGT RAYHYWGQGT LVTVSS      116

SEQ ID NO: 60          moltype = AA  length = 107
FEATURE                Location/Qualifiers
source                 1..107
                       mol_type = protein
                       organism = synthetic construct
SEQUENCE: 60
DIQLTQSPSS LSASVGDRVT ITCRASDKLY SNLAWYQQKP GKAPKLLIYD ATLLASGVPS  60
RFSGSGSGTD YTLTISSLQP EDFATYYCQH FWGTPLTFGQ GTKVEIK                107

SEQ ID NO: 61          moltype = AA  length = 223
FEATURE                Location/Qualifiers
source                 1..223
                       mol_type = protein
                       organism = synthetic construct
SEQUENCE: 61
EVQLVESGGG LVQPGGSLRL SCATSGFTFT SYWMHWVRQA PGKGLEWVAE INPTNGRTNY  60
IEKFKSRITL SVDKSKSTVY LQMNSLRAED TAVYYCARGT RAYHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTH                    223

SEQ ID NO: 62          moltype = AA  length = 214
FEATURE                Location/Qualifiers
source                 1..214
                       mol_type = protein
                       organism = synthetic construct
SEQUENCE: 62
DIQLTQSPSS LSASVGDRVT ITCRASDKLY SNLAWYQQKP GKAPKLLIYD ATLLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 63          moltype = AA  length = 116
FEATURE                Location/Qualifiers
source                 1..116
                       mol_type = protein
                       organism = synthetic construct
SEQUENCE: 63
EVQLVESGGG LVQPGGSLRL SCATSGYTFN SYWMHWVRQA PGKGLEWVAE INPTNGRTNY  60
IEKFKSRITL SVDKSKSTVY LQMNSLRAED TAVYYCARGT RAYHYWGQGT LVTVSS      116
```

```
SEQ ID NO: 64          moltype = AA  length = 107
FEATURE                Location/Qualifiers
source                 1..107
                       mol_type = protein
                       organism = synthetic construct
SEQUENCE: 64
DIQLTQSPSS LSASVGDRVT ITCRASDGLY SNLAWYQQKP GKAPKLLIYD ARNLASGVPS  60
RFSGSGSGTD YTLTISSLQP EDFATYYCQH FWGTPLTFGQ GTKVEIK                107

SEQ ID NO: 65          moltype = AA  length = 223
FEATURE                Location/Qualifiers
source                 1..223
                       mol_type = protein
                       organism = synthetic construct
SEQUENCE: 65
EVQLVESGGG LVQPGGSLRL SCATSGYTFN SYWMHWVRQA PGKGLEWVAE INPTNGRTNY  60
IEKFKSRITL SVDKSKSTVY LQMNSLRAED TAVYYCARGT RAYHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTH                    223

SEQ ID NO: 66          moltype = AA  length = 214
FEATURE                Location/Qualifiers
source                 1..214
                       mol_type = protein
                       organism = synthetic construct
SEQUENCE: 66
DIQLTQSPSS LSASVGDRVT ITCRASDGLY SNLAWYQQKP GKAPKLLIYD ARNLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 67          moltype = AA  length = 116
FEATURE                Location/Qualifiers
source                 1..116
                       mol_type = protein
                       organism = synthetic construct
SEQUENCE: 67
EVQLVESGGG LVQPGGSLRL SCATSGYTFN SYWMHWVRQA PGKGLEWVAE INPTNGRFNY  60
IEKFKSRITL SVDKSKSTVY LQMNSLRAED TAVYYCARGT RAYHYWGQGT LVTVSS      116

SEQ ID NO: 68          moltype = AA  length = 107
FEATURE                Location/Qualifiers
source                 1..107
                       mol_type = protein
                       organism = synthetic construct
SEQUENCE: 68
DIQLTQSPSS LSASVGDRVT ITCRASDNLY RNLAWYQQKP GKAPKLLIYD ARNLASGVPS  60
RFSGSGSGTD YTLTISSLQP EDFATYYCQH FWGTPLTFGQ GTKVEIK                107

SEQ ID NO: 69          moltype = AA  length = 223
FEATURE                Location/Qualifiers
source                 1..223
                       mol_type = protein
                       organism = synthetic construct
SEQUENCE: 69
EVQLVESGGG LVQPGGSLRL SCATSGYTFN SYWMHWVRQA PGKGLEWVAE INPTNGRFNY  60
IEKFKSRITL SVDKSKSTVY LQMNSLRAED TAVYYCARGT RAYHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTH                    223

SEQ ID NO: 70          moltype = AA  length = 214
FEATURE                Location/Qualifiers
source                 1..214
                       mol_type = protein
                       organism = synthetic construct
SEQUENCE: 70
DIQLTQSPSS LSASVGDRVT ITCRASDNLY RNLAWYQQKP GKAPKLLIYD ARNLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 71          moltype = AA  length = 116
FEATURE                Location/Qualifiers
source                 1..116
                       mol_type = protein
                       organism = synthetic construct
```

```
SEQUENCE: 71
EVQLVESGGG LVQPGGSLRL SCATSGYTFK SYWMHWVRQA PGKGLEWVAE INPTNGRTNY  60
IEKFKSRITL SVDKSKSTVY LQMNSLRAED TAVYYCARGT RAYHYWGQGT LVTVSS      116

SEQ ID NO: 72          moltype = AA  length = 223
FEATURE                Location/Qualifiers
source                 1..223
                       mol_type = protein
                       organism = synthetic construct
SEQUENCE: 72
EVQLVESGGG LVQPGGSLRL SCATSGYTFK SYWMHWVRQA PGKGLEWVAE INPTNGRTNY  60
IEKFKSRITL SVDKSKSTVY LQMNSLRAED TAVYYCARGT RAYHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTH                    223

SEQ ID NO: 73          moltype = AA  length = 214
FEATURE                Location/Qualifiers
source                 1..214
                       mol_type = protein
                       organism = synthetic construct
SEQUENCE: 73
DIQLTQSPSS LSASVGDRVT ITCRASDKLY SNLAWYQQKP GKAPKLLIYD ATLLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWCV DNALQSGNSQ ESVTEQDSKD STYSLSSTLT  180
LSKADYEKHK VYACEVTHQG LSSPVTKSFN RGEC                              214

SEQ ID NO: 74          moltype = AA  length = 214
FEATURE                Location/Qualifiers
source                 1..214
                       mol_type = protein
                       organism = synthetic construct
SEQUENCE: 74
DIQLTQSPSS LSASVGDRVT ITCRASDKLY SNLAWYQQKP GKAPKLLIYD ATLLASGVPS  60
RFSGSGSGTD YTLTISSLQP EDFATYYCQH FWGTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPCTKSFN RGEC                              214

SEQ ID NO: 75          moltype = AA  length = 223
FEATURE                Location/Qualifiers
source                 1..223
                       mol_type = protein
                       organism = synthetic construct
SEQUENCE: 75
EVQLVESGGG LVQPGGSLRL SCATSGFTFT SYWMHWVRQA PGKGLEWVAE INPTNGRTNY  60
IEKFKSRITL SVDKSKSTVY LQMNSLRAED TAVYYCARGT RAYHYWGQGT LVTVSSASTK  120
GPSVFPLAPS SKSTSGGTCA LGCLVKDYFP EPVTVSWNSG ALTSGVHTFP AVLQSSGLYS  180
LSSVVTVPSS SLGTQTYICN VNHKPSNTKV DKRVEPKSCD KTH                    223

SEQ ID NO: 76          moltype = AA  length = 223
FEATURE                Location/Qualifiers
source                 1..223
                       mol_type = protein
                       organism = synthetic construct
SEQUENCE: 76
EVQLVESGGG LVQPGGSLRL SCATSGFTFT SYWMHWVRQA PGKGLEWVAE INPTNGRTNY  60
IEKFKSRITL SVDKSKSTVY LQMNSLRAED TAVYYCARGT RAYHYWGQGT LVTVSSCSTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTH                    223

SEQ ID NO: 77          moltype = AA  length = 446
FEATURE                Location/Qualifiers
source                 1..446
                       mol_type = protein
                       organism = synthetic construct
SEQUENCE: 77
EVQLVESGGG LVQPGGSLRL SCATSGFTFT SYWMHWVRQA PGKGLEWVAE INPTNGRTNY  60
IEKFKSRITL SVDKSKSTVY LQMNSLRAED TAVYYCARGT RAYHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL YITREPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPCREEMTKN  360
QVSLWCLVKG FYPSDIAVEW ESNGQPENNY KTTPPVLDSD GSFFLYSKLT VDKSRWQQGN  420
VFSCSVMHEA LHNHYTQKSL SLSPGK                                       446

SEQ ID NO: 78          moltype = AA  length = 227
FEATURE                Location/Qualifiers
source                 1..227
                       mol_type = protein
                       organism = synthetic construct
```

-continued

```
SEQUENCE: 78
DKTHTCPPCP APEAAGGPSV FLFPPKPKDT LYITREPEVT CVVVDVSHED PEVKFNWYVD  60
GVEVHNAKTK PREEQYNSTY RVVSVLTVLH QDWLNGKEYK CKVSNKALGA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 79          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 79
cacttttgac ctgctaatca a                                            21

SEQ ID NO: 80          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
```

-continued

```
modified_base         7
                      mod_base = um
modified_base         8
                      mod_base = gm
modified_base         9
                      mod_base = OTHER
                      note = 2'-fluoroadenosine
modified_base         10
                      mod_base = OTHER
                      note = 2'-fluorocytidine
modified_base         11
                      mod_base = OTHER
                      note = 2'-fluorocytidine
modified_base         12
                      mod_base = um
modified_base         13
                      mod_base = gm
modified_base         14
                      mod_base = cm
modified_base         15
                      mod_base = um
modified_base         16
                      mod_base = OTHER
                      note = 2'-O-methyladenosine
modified_base         17
                      mod_base = OTHER
                      note = 2'-O-methyladenosine
modified_base         18
                      mod_base = um
modified_base         19
                      mod_base = cm
modified_base         20
                      mod_base = OTHER
                      note = 2'-O-methyladenosine
modified_base         21
                      mod_base = OTHER
                      note = 2'-O-methyladenosine
source                1..21
                      mol_type = other RNA
                      organism = synthetic construct
SEQUENCE: 80
cacttttgac ctgctaatca a                                            21

SEQ ID NO: 81         moltype = RNA  length = 21
FEATURE               Location/Qualifiers
modified_base         1
                      mod_base = cm
modified_base         2
                      mod_base = OTHER
                      note = 2'-O-methyladenosine
modified_base         3
                      mod_base = cm
modified_base         4
                      mod_base = um
modified_base         5
                      mod_base = um
modified_base         6
                      mod_base = um
modified_base         7
                      mod_base = um
modified_base         8
                      mod_base = gm
modified_base         9
                      mod_base = OTHER
                      note = 2'-fluoroadenosine
modified_base         10
                      mod_base = OTHER
                      note = 2'-fluorocytidine
modified_base         11
                      mod_base = OTHER
                      note = 2'-fluorocytidine
modified_base         12
                      mod_base = um
modified_base         13
                      mod_base = gm
modified_base         14
                      mod_base = cm
modified_base         15
                      mod_base = um
```

```
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 81
cacttttgac ctgctaatca a                                            21

SEQ ID NO: 82          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 82
cacttttgac ctgctaatca a                                            21
```

-continued

```
SEQ ID NO: 83          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 83
cacttttgac ctgctaatca a                                                    21

SEQ ID NO: 84          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
```

-continued

```
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 84
cacttttgac ctgctaatca a                                                21

SEQ ID NO: 85          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
```

-continued

```
modified_base           17
                        mod_base = OTHER
                        note = 2'-O-methyladenosine
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 85
cacttttgac ctgctaatca a                                                  21

SEQ ID NO: 86           moltype = RNA  length = 21
FEATURE                 Location/Qualifiers
modified_base           1
                        mod_base = cm
modified_base           2
                        mod_base = OTHER
                        note = 2'-O-methyladenosine
modified_base           3
                        mod_base = cm
modified_base           4
                        mod_base = um
modified_base           5
                        mod_base = um
modified_base           6
                        mod_base = um
modified_base           7
                        mod_base = um
modified_base           8
                        mod_base = gm
modified_base           9
                        mod_base = OTHER
                        note = 2'-fluoroadenosine
modified_base           10
                        mod_base = OTHER
                        note = 2'-fluorocytidine
modified_base           11
                        mod_base = OTHER
                        note = 2'-fluorocytidine
modified_base           12
                        mod_base = um
modified_base           13
                        mod_base = gm
modified_base           14
                        mod_base = cm
modified_base           15
                        mod_base = um
modified_base           16
                        mod_base = OTHER
                        note = 2'-O-methyladenosine
modified_base           17
                        mod_base = OTHER
                        note = 2'-O-methyladenosine
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 86
cacttttgac ctgctaatca a                                                  21

SEQ ID NO: 87           moltype = RNA  length = 21
FEATURE                 Location/Qualifiers
```

-continued

```
modified_base         1
                      mod_base = cm
modified_base         2
                      mod_base = OTHER
                      note = 2'-O-methyladenosine
modified_base         3
                      mod_base = cm
modified_base         4
                      mod_base = um
modified_base         5
                      mod_base = um
modified_base         6
                      mod_base = um
modified_base         7
                      mod_base = um
modified_base         8
                      mod_base = gm
modified_base         9
                      mod_base = OTHER
                      note = 2'-fluoroadenosine
modified_base         10
                      mod_base = OTHER
                      note = 2'-fluorocytidine
modified_base         11
                      mod_base = OTHER
                      note = 2'-fluorocytidine
modified_base         12
                      mod_base = um
modified_base         13
                      mod_base = gm
modified_base         14
                      mod_base = cm
modified_base         15
                      mod_base = um
modified_base         16
                      mod_base = OTHER
                      note = 2'-O-methyladenosine
modified_base         17
                      mod_base = OTHER
                      note = 2'-O-methyladenosine
modified_base         18
                      mod_base = um
modified_base         19
                      mod_base = cm
modified_base         20
                      mod_base = OTHER
                      note = 2'-O-methyladenosine
modified_base         21
                      mod_base = OTHER
                      note = 2'-O-methyladenosine
source                1..21
                      mol_type = other RNA
                      organism = synthetic construct
SEQUENCE: 87
cacttttgac ctgctaatca a                                              21

SEQ ID NO: 88         moltype = RNA  length = 21
FEATURE               Location/Qualifiers
modified_base         1
                      mod_base = cm
modified_base         2
                      mod_base = OTHER
                      note = 2'-O-methyladenosine
modified_base         3
                      mod_base = cm
modified_base         4
                      mod_base = um
modified_base         5
                      mod_base = um
modified_base         6
                      mod_base = um
modified_base         7
                      mod_base = um
modified_base         8
                      mod_base = gm
modified_base         9
                      mod_base = OTHER
                      note = 2'-fluoroadenosine
```

| | |
|---|---|
| modified_base | 10<br>mod_base = OTHER<br>note = 2'-fluorocytidine |
| modified_base | 11<br>mod_base = OTHER<br>note = 2'-fluorocytidine |
| modified_base | 12<br>mod_base = um |
| modified_base | 13<br>mod_base = gm |
| modified_base | 14<br>mod_base = cm |
| modified_base | 15<br>mod_base = um |
| modified_base | 16<br>mod_base = OTHER<br>note = 2'-O-methyladenosine |
| modified_base | 17<br>mod_base = OTHER<br>note = 2'-O-methyladenosine |
| modified_base | 18<br>mod_base = um |
| modified_base | 19<br>mod_base = cm |
| modified_base | 20<br>mod_base = OTHER<br>note = 2'-O-methyladenosine |
| modified_base | 21<br>mod_base = OTHER<br>note = 2'-O-methyladenosine |
| source | 1..21<br>mol_type = other RNA<br>organism = synthetic construct |

SEQUENCE: 88
cacttttgac ctgctaatca a 21

| | |
|---|---|
| SEQ ID NO: 89 | moltype = RNA length = 21 |
| FEATURE | Location/Qualifiers |
| modified_base | 1<br>mod_base = cm |
| modified_base | 2<br>mod_base = OTHER<br>note = 2'-O-methyladenosine |
| modified_base | 3<br>mod_base = cm |
| modified_base | 4<br>mod_base = um |
| modified_base | 5<br>mod_base = um |
| modified_base | 6<br>mod_base = um |
| modified_base | 7<br>mod_base = um |
| modified_base | 8<br>mod_base = gm |
| modified_base | 9<br>mod_base = OTHER<br>note = 2'-fluoroadenosine |
| modified_base | 10<br>mod_base = OTHER<br>note = 2'-fluorocytidine |
| modified_base | 11<br>mod_base = OTHER<br>note = 2'-fluorocytidine |
| modified_base | 12<br>mod_base = um |
| modified_base | 13<br>mod_base = gm |
| modified_base | 14<br>mod_base = cm |
| modified_base | 15<br>mod_base = um |
| modified_base | 16<br>mod_base = OTHER<br>note = 2'-O-methyladenosine |
| modified_base | 17<br>mod_base = OTHER<br>note = 2'-O-methyladenosine |

-continued

```
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 89
cacttttgac ctgctaatca a                                            21

SEQ ID NO: 90          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 90
cacttttgac ctgctaatca a                                            21

SEQ ID NO: 91          moltype = RNA  length = 21
FEATURE                Location/Qualifiers
modified_base          1
                       mod_base = cm
```

-continued

```
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 91
cacttttgac ctgctaatca a                                                21

SEQ ID NO: 92          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
```

```
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 92
cacttttgac ctgctaatca a                                              21

SEQ ID NO: 93          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
```

-continued

```
modified_base         20
                      mod_base = OTHER
                      note = 2'-O-methyladenosine
modified_base         21
                      mod_base = OTHER
                      note = 2'-O-methyladenosine
source                1..21
                      mol_type = other RNA
                      organism = synthetic construct
SEQUENCE: 93
cacttttgac ctgctaatca a                                            21

SEQ ID NO: 94         moltype = RNA  length = 21
FEATURE               Location/Qualifiers
modified_base         1
                      mod_base = cm
modified_base         2
                      mod_base = OTHER
                      note = 2'-O-methyladenosine
modified_base         3
                      mod_base = cm
modified_base         4
                      mod_base = um
modified_base         5
                      mod_base = um
modified_base         6
                      mod_base = um
modified_base         7
                      mod_base = um
modified_base         8
                      mod_base = gm
modified_base         9
                      mod_base = OTHER
                      note = 2'-fluoroadenosine
modified_base         10
                      mod_base = OTHER
                      note = 2'-fluorocytidine
modified_base         11
                      mod_base = OTHER
                      note = 2'-fluorocytidine
modified_base         12
                      mod_base = um
modified_base         13
                      mod_base = gm
modified_base         14
                      mod_base = cm
modified_base         15
                      mod_base = um
modified_base         16
                      mod_base = OTHER
                      note = 2'-O-methyladenosine
modified_base         17
                      mod_base = OTHER
                      note = 2'-O-methyladenosine
modified_base         18
                      mod_base = um
modified_base         19
                      mod_base = cm
modified_base         20
                      mod_base = OTHER
                      note = 2'-O-methyladenosine
modified_base         21
                      mod_base = OTHER
                      note = 2'-O-methyladenosine
source                1..21
                      mol_type = other RNA
                      organism = synthetic construct
SEQUENCE: 94
cacttttgac ctgctaatca a                                            21

SEQ ID NO: 95         moltype = RNA  length = 21
FEATURE               Location/Qualifiers
modified_base         1
                      mod_base = cm
modified_base         2
                      mod_base = OTHER
                      note = 2'-O-methyladenosine
modified_base         3
                      mod_base = cm
```

-continued

```
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 95
cacttttgac ctgctaatca a                                                   21

SEQ ID NO: 96          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
```

-continued

```
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 96
cacttttgac ctgctaatca a                                            21

SEQ ID NO: 97          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
```

```
modified_base          21
                       mod_base = OTHER
                       note = 2'-O-methyladenosine
source                 1..21
                       mol_type = other RNA
                       organism = synthetic construct
SEQUENCE: 97
cacttttgac ctgctaatca a                                              21

SEQ ID NO: 98          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 98
cacttttgac ctgctaatca a                                              21

SEQ ID NO: 99          moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
```

-continued

```
modified_base         5
                      mod_base = um
modified_base         6
                      mod_base = um
modified_base         7
                      mod_base = um
modified_base         8
                      mod_base = gm
modified_base         9
                      mod_base = OTHER
                      note = 2'-fluoroadenosine
modified_base         10
                      mod_base = OTHER
                      note = 2'-fluorocytidine
modified_base         11
                      mod_base = OTHER
                      note = 2'-fluorocytidine
modified_base         12
                      mod_base = um
modified_base         13
                      mod_base = gm
modified_base         14
                      mod_base = cm
modified_base         15
                      mod_base = um
modified_base         16
                      mod_base = OTHER
                      note = 2'-O-methyladenosine
modified_base         17
                      mod_base = OTHER
                      note = 2'-O-methyladenosine
modified_base         18
                      mod_base = um
modified_base         19
                      mod_base = cm
modified_base         20
                      mod_base = OTHER
                      note = 2'-O-methyladenosine
modified_base         21
                      mod_base = OTHER
                      note = 2'-O-methyladenosine
source                1..21
                      mol_type = other RNA
                      organism = synthetic construct
SEQUENCE: 99
cacttttgac ctgctaatca a                                                21

SEQ ID NO: 100        moltype = RNA  length = 21
FEATURE               Location/Qualifiers
modified_base         1
                      mod_base = cm
modified_base         2
                      mod_base = OTHER
                      note = 2'-O-methyladenosine
modified_base         3
                      mod_base = cm
modified_base         4
                      mod_base = um
modified_base         5
                      mod_base = um
modified_base         6
                      mod_base = um
modified_base         7
                      mod_base = um
modified_base         8
                      mod_base = gm
modified_base         9
                      mod_base = OTHER
                      note = 2'-fluoroadenosine
modified_base         10
                      mod_base = OTHER
                      note = 2'-fluorocytidine
modified_base         11
                      mod_base = OTHER
                      note = 2'-fluorocytidine
modified_base         12
                      mod_base = um
modified_base         13
                      mod_base = gm
```

-continued

```
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 100
cacttttgac ctgctaatca a                                            21

SEQ ID NO: 101         moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
```

```
source                  1..21
                        mol_type = other RNA
                        organism = synthetic construct
SEQUENCE: 101
cacttttgac ctgctaatca a                                             21

SEQ ID NO: 102          moltype = RNA  length = 21
FEATURE                 Location/Qualifiers
modified_base           1
                        mod_base = cm
modified_base           2
                        mod_base = OTHER
                        note = 2'-O-methyladenosine
modified_base           3
                        mod_base = cm
modified_base           4
                        mod_base = um
modified_base           5
                        mod_base = um
modified_base           6
                        mod_base = um
modified_base           7
                        mod_base = um
modified_base           8
                        mod_base = gm
modified_base           9
                        mod_base = OTHER
                        note = 2'-fluoroadenosine
modified_base           10
                        mod_base = OTHER
                        note = 2'-fluorocytidine
modified_base           11
                        mod_base = OTHER
                        note = 2'-fluorocytidine
modified_base           12
                        mod_base = um
modified_base           13
                        mod_base = gm
modified_base           14
                        mod_base = cm
modified_base           15
                        mod_base = um
modified_base           16
                        mod_base = OTHER
                        note = 2'-O-methyladenosine
modified_base           17
                        mod_base = OTHER
                        note = 2'-O-methyladenosine
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 102
cacttttgac ctgctaatca a                                             21

SEQ ID NO: 103          moltype = RNA  length = 21
FEATURE                 Location/Qualifiers
modified_base           1
                        mod_base = cm
modified_base           2
                        mod_base = OTHER
                        note = 2'-O-methyladenosine
modified_base           3
                        mod_base = cm
modified_base           4
                        mod_base = um
modified_base           5
                        mod_base = um
modified_base           6
                        mod_base = um
```

-continued

```
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 103
cacttttgac ctgctaatca a                                          21

SEQ ID NO: 104         moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
```

-continued

```
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 104
cacttttgac ctgctaatca a                                             21

SEQ ID NO: 105         moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 105
cacttttgac ctgctaatca a                                             21
```

-continued

```
SEQ ID NO: 106          moltype = RNA  length = 21
FEATURE                 Location/Qualifiers
modified_base           1
                        mod_base = cm
modified_base           2
                        mod_base = OTHER
                        note = 2'-O-methyladenosine
modified_base           3
                        mod_base = cm
modified_base           4
                        mod_base = um
modified_base           5
                        mod_base = um
modified_base           6
                        mod_base = um
modified_base           7
                        mod_base = um
modified_base           8
                        mod_base = gm
modified_base           9
                        mod_base = OTHER
                        note = 2'-fluoroadenosine
modified_base           10
                        mod_base = OTHER
                        note = 2'-fluorocytidine
modified_base           11
                        mod_base = OTHER
                        note = 2'-fluorocytidine
modified_base           12
                        mod_base = um
modified_base           13
                        mod_base = gm
modified_base           14
                        mod_base = cm
modified_base           15
                        mod_base = um
modified_base           16
                        mod_base = OTHER
                        note = 2'-O-methyladenosine
modified_base           17
                        mod_base = OTHER
                        note = 2'-O-methyladenosine
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 106
cacttttgac ctgctaatca a                                              21

SEQ ID NO: 107          moltype = RNA  length = 21
FEATURE                 Location/Qualifiers
modified_base           1
                        mod_base = cm
modified_base           2
                        mod_base = OTHER
                        note = 2'-O-methyladenosine
modified_base           3
                        mod_base = cm
modified_base           4
                        mod_base = um
modified_base           5
                        mod_base = um
modified_base           6
                        mod_base = um
modified_base           7
                        mod_base = um
modified_base           8
                        mod_base = gm
```

-continued

```
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 107
cacttttgac ctgctaatca a                                            21

SEQ ID NO: 108         moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
```

-continued

```
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 108
cacttttgac ctgctaatca a                                            21

SEQ ID NO: 109         moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = gm
modified_base          4
                       mod_base = cm
modified_base          5
                       mod_base = OTHER
                       note = 2'-O-methyladenosine
modified_base          6
                       mod_base = um
modified_base          7
                       mod_base = cm
modified_base          8
                       mod_base = gm
modified_base          9
                       mod_base = OTHER
                       note = 2'-fluoroadenosine
modified_base          10
                       mod_base = cm
modified_base          11
                       mod_base = OTHER
                       note = 2'-fluoroadenosine
modified_base          12
                       mod_base = OTHER
                       note = 2'-fluorouridine
modified_base          13
                       mod_base = gm
modified_base          14
                       mod_base = gm
modified_base          15
                       mod_base = um
modified_base          16
                       mod_base = OTHER
                       note = 2'-O-methyladenosine
modified_base          17
                       mod_base = gm
modified_base          18
                       mod_base = OTHER
                       note = 2'-O-methyladenosine
modified_base          19
                       mod_base = cm
modified_base          20
                       mod_base = um
modified_base          21
                       mod_base = OTHER
                       note = 2'-O-methyladenosine
source                 1..21
                       mol_type = other RNA
                       organism = synthetic construct
SEQUENCE: 109
cagcatcgac atggtagact a                                            21

SEQ ID NO: 110         moltype = RNA  length = 21
FEATURE                Location/Qualifiers
```

-continued

```
modified_base          1
                       mod_base = OTHER
                       note = 2'-O-methyladenosine
modified_base          2
                       mod_base = gm
modified_base          3
                       mod_base = gm
modified_base          4
                       mod_base = cm
modified_base          5
                       mod_base = OTHER
                       note = 2'-O-methyladenosine
modified_base          6
                       mod_base = OTHER
                       note = 2'-O-methyladenosine
modified_base          7
                       mod_base = um
modified_base          8
                       mod_base = um
modified_base          9
                       mod_base = OTHER
                       note = 2'-fluorocytidine
modified_base          10
                       mod_base = OTHER
                       note = 2'-O-methyladenosine
modified_base          11
                       mod_base = OTHER
                       note = 2'-fluoroguanosine
modified_base          12
                       mod_base = um
modified_base          13
                       mod_base = OTHER
                       note = 2'-fluorocytidine
modified_base          14
                       mod_base = um
modified_base          15
                       mod_base = cm
modified_base          16
                       mod_base = gm
modified_base          17
                       mod_base = um
modified_base          18
                       mod_base = um
modified_base          19
                       mod_base = gm
modified_base          20
                       mod_base = um
modified_base          21
                       mod_base = OTHER
                       note = 2'-O-methyladenosine
source                 1..21
                       mol_type = other RNA
                       organism = synthetic construct
SEQUENCE: 110
aggcaattca gtctcgttgt a                                          21

SEQ ID NO: 111         moltype = RNA  length = 21
FEATURE                Location/Qualifiers
modified_base          1
                       mod_base = OTHER
                       note = 2'-O-methyladenosine
modified_base          2
                       mod_base = gm
modified_base          3
                       mod_base = gm
modified_base          4
                       mod_base = cm
modified_base          5
                       mod_base = OTHER
                       note = 2'-O-methyladenosine
modified_base          6
                       mod_base = OTHER
                       note = 2'-O-methyladenosine
modified_base          7
                       mod_base = um
modified_base          8
                       mod_base = um
```

```
modified_base          9
                       mod_base = OTHER
                       note = 2'-fluorocytidine
modified_base          10
                       mod_base = OTHER
                       note = 2'-O-methyladenosine
modified_base          11
                       mod_base = OTHER
                       note = 2'-fluoroguanosine
modified_base          12
                       mod_base = um
modified_base          13
                       mod_base = OTHER
                       note = 2'-fluorocytidine
modified_base          14
                       mod_base = um
modified_base          15
                       mod_base = cm
modified_base          16
                       mod_base = gm
modified_base          17
                       mod_base = um
modified_base          18
                       mod_base = um
modified_base          19
                       mod_base = gm
modified_base          20
                       mod_base = um
modified_base          21
                       mod_base = OTHER
                       note = 2'-O-methyladenosine
source                 1..21
                       mol_type = other RNA
                       organism = synthetic construct
SEQUENCE: 111
aggcaattca gtctcgttgt a                                            21

SEQ ID NO: 112         moltype = RNA  length = 21
FEATURE                Location/Qualifiers
modified_base          1
                       mod_base = cm
modified_base          2
                       mod_base = cm
modified_base          3
                       mod_base = OTHER
                       note = 2'-O-methyladenosine
modified_base          4
                       mod_base = um
modified_base          5
                       mod_base = gm
modified_base          6
                       mod_base = cm
modified_base          7
                       mod_base = OTHER
                       note = 2'-O-methyladenosine
modified_base          8
                       mod_base = OTHER
                       note = 2'-O-methyladenosine
modified_base          9
                       mod_base = OTHER
                       note = 2'-fluoroguanosine
modified_base          10
                       mod_base = OTHER
                       note = 2'-O-methyladenosine
modified_base          11
                       mod_base = OTHER
                       note = 2'-fluorocytidine
modified_base          12
                       mod_base = OTHER
                       note = 2'-fluorouridine
modified_base          13
                       mod_base = cm
modified_base          14
                       mod_base = OTHER
                       note = 2'-O-methyladenosine
modified_base          15
                       mod_base = cm
modified_base          16
                       mod_base = um
```

```
modified_base          17
                       mod_base = um
modified_base          18
                       mod_base = OTHER
                       note = 2'-O-methyladenosine
modified_base          19
                       mod_base = gm
modified_base          20
                       mod_base = um
modified_base          21
                       mod_base = OTHER
                       note = 2'-O-methyladenosine
source                 1..21
                       mol_type = other RNA
                       organism = synthetic construct
SEQUENCE: 112
ccatgcaaga ctcacttagt a                                            21

SEQ ID NO: 113         moltype = RNA  length = 21
FEATURE                Location/Qualifiers
modified_base          1
                       mod_base = cm
modified_base          2
                       mod_base = um
modified_base          3
                       mod_base = gm
modified_base          4
                       mod_base = gm
modified_base          5
                       mod_base = OTHER
                       note = 2'-O-methyladenosine
modified_base          6
                       mod_base = gm
modified_base          7
                       mod_base = cm
modified_base          8
                       mod_base = OTHER
                       note = 2'-O-methyladenosine
modified_base          9
                       mod_base = OTHER
                       note = 2'-fluoroadenosine
modified_base          10
                       mod_base = gm
modified_base          11
                       mod_base = OTHER
                       note = 2'-fluorouridine
modified_base          12
                       mod_base = um
modified_base          13
                       mod_base = OTHER
                       note = 2'-fluoroguanosine
modified_base          14
                       mod_base = OTHER
                       note = 2'-O-methyladenosine
modified_base          15
                       mod_base = OTHER
                       note = 2'-O-methyladenosine
modified_base          16
                       mod_base = um
modified_base          17
                       mod_base = gm
modified_base          18
                       mod_base = OTHER
                       note = 2'-O-methyladenosine
modified_base          19
                       mod_base = um
modified_base          20
                       mod_base = cm
modified_base          21
                       mod_base = OTHER
                       note = 2'-O-methyladenosine
source                 1..21
                       mol_type = other RNA
                       organism = synthetic construct
SEQUENCE: 113
ctggagcaag ttgaatgatc a                                            21

SEQ ID NO: 114         moltype = RNA  length = 21
FEATURE                Location/Qualifiers
```

```
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 114
cacttttgac ctgctaatca a                                                21

SEQ ID NO: 115         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
```

-continued

```
modified_base           7
                        mod_base = OTHER
                        note = 2'-fluoroadenosine
modified_base           8
                        mod_base = gm
modified_base           9
                        mod_base = cm
modified_base           10
                        mod_base = OTHER
                        note = 2'-O-methyladenosine
modified_base           11
                        mod_base = gm
modified_base           12
                        mod_base = OTHER
                        note = 2'-fluoroguanosine
modified_base           13
                        mod_base = um
modified_base           14
                        mod_base = OTHER
                        note = 2'-fluorocytidine
modified_base           15
                        mod_base = OTHER
                        note = 2'-O-methyladenosine
modified_base           16
                        mod_base = OTHER
                        note = 2'-fluoroadenosine
modified_base           17
                        mod_base = OTHER
                        note = 2'-O-methyladenosine
modified_base           18
                        mod_base = OTHER
                        note = 2'-O-methyladenosine
modified_base           19
                        mod_base = gm
modified_base           19^20
                        mod_base = OTHER
                        note = phosphorothioate linkage
modified_base           20
                        mod_base = um
modified_base           20^21
                        mod_base = OTHER
                        note = phosphorothioate linkage
modified_base           21
                        mod_base = gm
source                  1..21
                        mol_type = other RNA
                        organism = synthetic construct
SEQUENCE: 115
ttgattagca ggtcaaaagt g                                                21

SEQ ID NO: 116          moltype = RNA  length = 21
FEATURE                 Location/Qualifiers
modified_base           1
                        mod_base = OTHER
                        note = 5'-cyclopropyl phosphonate-2'-O-methyluridine
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = OTHER
                        note = 2'-fluoroadenosine
modified_base           8
                        mod_base = gm
```

-continued

```
modified_base         9
                      mod_base = cm
modified_base         10
                      mod_base = OTHER
                      note = 2'-O-methyladenosine
modified_base         11
                      mod_base = gm
modified_base         12
                      mod_base = OTHER
                      note = 2'-fluoroguanosine
modified_base         13
                      mod_base = um
modified_base         14
                      mod_base = OTHER
                      note = 2'-fluorocytidine
modified_base         15
                      mod_base = OTHER
                      note = 2'-O-methyladenosine
modified_base         16
                      mod_base = OTHER
                      note = 2'-fluoroadenosine
modified_base         17
                      mod_base = OTHER
                      note = 2'-O-methyladenosine
modified_base         18
                      mod_base = OTHER
                      note = 2'-O-methyladenosine
modified_base         19
                      mod_base = gm
modified_base         19^20
                      mod_base = OTHER
                      note = phosphorothioate linkage
modified_base         20
                      mod_base = um
modified_base         20^21
                      mod_base = OTHER
                      note = phosphorothioate linkage
modified_base         21
                      mod_base = gm
source                1..21
                      mol_type = other RNA
                      organism = synthetic construct
SEQUENCE: 116
ttgattagca ggtcaaaagt g                                              21

SEQ ID NO: 117        moltype = RNA  length = 21
FEATURE               Location/Qualifiers
modified_base         1
                      mod_base = OTHER
                      note = 5'-cyclopropyl phosphonate-2'-O-methyluridine
modified_base         1^2
                      mod_base = OTHER
                      note = phosphorothioate linkage
modified_base         2
                      mod_base = OTHER
                      note = 2'-fluorouridine
modified_base         2^3
                      mod_base = OTHER
                      note = phosphorothioate linkage
modified_base         3
                      mod_base = gm
modified_base         4
                      mod_base = OTHER
                      note = 2'-O-methyladenosine
modified_base         5
                      mod_base = um
modified_base         6
                      mod_base = um
modified_base         7
                      mod_base = OTHER
                      note = 2'-fluoroadenosine
modified_base         8
                      mod_base = gm
modified_base         9
                      mod_base = cm
modified_base         10
                      mod_base = OTHER
                      note = 2'-O-methyladenosine
```

```
modified_base           11
                        mod_base = gm
modified_base           12
                        mod_base = OTHER
                        note = 2'-fluoroguanosine
modified_base           13
                        mod_base = um
modified_base           14
                        mod_base = OTHER
                        note = 2'-fluorocytidine
modified_base           15
                        mod_base = OTHER
                        note = 2'-O-methyladenosine
modified_base           16
                        mod_base = OTHER
                        note = 2'-fluoroadenosine
modified_base           17
                        mod_base = OTHER
                        note = 2'-O-methyladenosine
modified_base           18
                        mod_base = OTHER
                        note = 2'-O-methyladenosine
modified_base           19
                        mod_base = gm
modified_base           19^20
                        mod_base = OTHER
                        note = phosphorothioate linkage
modified_base           20
                        mod_base = um
modified_base           20^21
                        mod_base = OTHER
                        note = phosphorothioate linkage
modified_base           21
                        mod_base = gm
source                  1..21
                        mol_type = other RNA
                        organism = synthetic construct
SEQUENCE: 117
ttgattagca ggtcaaaagt g                                            21

SEQ ID NO: 118          moltype = RNA  length = 21
FEATURE                 Location/Qualifiers
modified_base           1
                        mod_base = OTHER
                        note = 5'-cyclopropyl phosphonate-2'-O-methyluridine
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = OTHER
                        note = 2'-fluoroadenosine
modified_base           8
                        mod_base = gm
modified_base           9
                        mod_base = cm
modified_base           10
                        mod_base = OTHER
                        note = 2'-O-methyladenosine
modified_base           11
                        mod_base = gm
modified_base           12
                        mod_base = OTHER
                        note = 2'-fluoroguanosine
```

```
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 118
ttgattagca ggtcaaaagt g                                              21

SEQ ID NO: 119         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
```

```
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 119
ttgattagca ggtcaaaagt g                                            21

SEQ ID NO: 120         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
```

-continued

```
modified_base         17
                      mod_base = OTHER
                      note = 2'-O-methyladenosine
modified_base         18
                      mod_base = OTHER
                      note = 2'-O-methyladenosine
modified_base         19
                      mod_base = gm
modified_base         19^20
                      mod_base = OTHER
                      note = phosphorothioate linkage
modified_base         20
                      mod_base = um
modified_base         20^21
                      mod_base = OTHER
                      note = phosphorothioate linkage
modified_base         21
                      mod_base = gm
source                1..21
                      mol_type = other RNA
                      organism = synthetic construct
SEQUENCE: 120
ttgattagca ggtcaaaagt g                                            21

SEQ ID NO: 121        moltype = RNA  length = 21
FEATURE               Location/Qualifiers
modified_base         1
                      mod_base = OTHER
                      note = 5'-cyclopropyl phosphonate-2'-O-methyluridine
modified_base         1^2
                      mod_base = OTHER
                      note = phosphorothioate linkage
modified_base         2
                      mod_base = OTHER
                      note = 2'-fluorouridine
modified_base         2^3
                      mod_base = OTHER
                      note = phosphorothioate linkage
modified_base         3
                      mod_base = gm
modified_base         4
                      mod_base = OTHER
                      note = 2'-O-methyladenosine
modified_base         5
                      mod_base = um
modified_base         6
                      mod_base = um
modified_base         7
                      mod_base = OTHER
                      note = 2'-fluoroadenosine
modified_base         8
                      mod_base = gm
modified_base         9
                      mod_base = cm
modified_base         10
                      mod_base = OTHER
                      note = 2'-O-methyladenosine
modified_base         11
                      mod_base = gm
modified_base         12
                      mod_base = OTHER
                      note = 2'-fluoroguanosine
modified_base         13
                      mod_base = um
modified_base         14
                      mod_base = OTHER
                      note = 2'-fluorocytidine
modified_base         15
                      mod_base = OTHER
                      note = 2'-O-methyladenosine
modified_base         16
                      mod_base = OTHER
                      note = 2'-fluoroadenosine
modified_base         17
                      mod_base = OTHER
                      note = 2'-O-methyladenosine
modified_base         18
                      mod_base = OTHER
                      note = 2'-O-methyladenosine
```

-continued

```
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 121
ttgattagca ggtcaaaagt g                                        21

SEQ ID NO: 122         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
```

-continued

```
modified_base         20
                      mod_base = um
modified_base         20^21
                      mod_base = OTHER
                      note = phosphorothioate linkage
modified_base         21
                      mod_base = gm
source                1..21
                      mol_type = other RNA
                      organism = synthetic construct
SEQUENCE: 122
ttgattagca ggtcaaaagt g                                              21

SEQ ID NO: 123        moltype = RNA  length = 21
FEATURE               Location/Qualifiers
modified_base         1
                      mod_base = OTHER
                      note = 5'-cyclopropyl phosphonate-2'-O-methyluridine
modified_base         1^2
                      mod_base = OTHER
                      note = phosphorothioate linkage
modified_base         2
                      mod_base = OTHER
                      note = 2'-fluorouridine
modified_base         2^3
                      mod_base = OTHER
                      note = phosphorothioate linkage
modified_base         3
                      mod_base = gm
modified_base         4
                      mod_base = OTHER
                      note = 2'-O-methyladenosine
modified_base         5
                      mod_base = um
modified_base         6
                      mod_base = um
modified_base         7
                      mod_base = OTHER
                      note = 2'-fluoroadenosine
modified_base         8
                      mod_base = gm
modified_base         9
                      mod_base = cm
modified_base         10
                      mod_base = OTHER
                      note = 2'-O-methyladenosine
modified_base         11
                      mod_base = gm
modified_base         12
                      mod_base = OTHER
                      note = 2'-fluoroguanosine
modified_base         13
                      mod_base = um
modified_base         14
                      mod_base = OTHER
                      note = 2'-fluorocytidine
modified_base         15
                      mod_base = OTHER
                      note = 2'-O-methyladenosine
modified_base         16
                      mod_base = OTHER
                      note = 2'-fluoroadenosine
modified_base         17
                      mod_base = OTHER
                      note = 2'-O-methyladenosine
modified_base         18
                      mod_base = OTHER
                      note = 2'-O-methyladenosine
modified_base         19
                      mod_base = gm
modified_base         19^20
                      mod_base = OTHER
                      note = phosphorothioate linkage
modified_base         20
                      mod_base = um
modified_base         20^21
                      mod_base = OTHER
                      note = phosphorothioate linkage
```

```
modified_base          21
                       mod_base = gm
source                 1..21
                       mol_type = other RNA
                       organism = synthetic construct
SEQUENCE: 123
ttgattagca ggtcaaaagt g                                            21

SEQ ID NO: 124         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
```

```
SEQUENCE: 124
ttgattagca ggtcaaaagt g                                           21

SEQ ID NO: 125         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 125
ttgattagca ggtcaaaagt g                                           21

SEQ ID NO: 126         moltype = RNA  length = 21
FEATURE                Location/Qualifiers
```

-continued

```
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 126
ttgattagca ggtcaaaagt g                                              21

SEQ ID NO: 127         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
```

-continued

```
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 127
ttgattagca ggtcaaaagt g                                            21

SEQ ID NO: 128         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
```

-continued

```
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 128
ttgattagca ggtcaaaagt g                                        21

SEQ ID NO: 129         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
```

-continued

```
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 129
ttgattagca ggtcaaaagt g                                           21

SEQ ID NO: 130         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
```

```
modified_base         7
                      mod_base = OTHER
                      note = 2'-fluoroadenosine
modified_base         8
                      mod_base = gm
modified_base         9
                      mod_base = cm
modified_base         10
                      mod_base = OTHER
                      note = 2'-O-methyladenosine
modified_base         11
                      mod_base = gm
modified_base         12
                      mod_base = OTHER
                      note = 2'-fluoroguanosine
modified_base         13
                      mod_base = um
modified_base         14
                      mod_base = OTHER
                      note = 2'-fluorocytidine
modified_base         15
                      mod_base = OTHER
                      note = 2'-O-methyladenosine
modified_base         16
                      mod_base = OTHER
                      note = 2'-fluoroadenosine
modified_base         17
                      mod_base = OTHER
                      note = 2'-O-methyladenosine
modified_base         18
                      mod_base = OTHER
                      note = 2'-O-methyladenosine
modified_base         19
                      mod_base = gm
modified_base         19^20
                      mod_base = OTHER
                      note = phosphorothioate linkage
modified_base         20
                      mod_base = um
modified_base         20^21
                      mod_base = OTHER
                      note = phosphorothioate linkage
modified_base         21
                      mod_base = gm
source                1..21
                      mol_type = other RNA
                      organism = synthetic construct
SEQUENCE: 130
ttgattagca ggtcaaaagt g                                           21

SEQ ID NO: 131        moltype = RNA  length = 21
FEATURE               Location/Qualifiers
modified_base         1
                      mod_base = OTHER
                      note = 5'-cyclopropyl phosphonate-2'-O-methyluridine
modified_base         1^2
                      mod_base = OTHER
                      note = phosphorothioate linkage
modified_base         2
                      mod_base = OTHER
                      note = 2'-fluorouridine
modified_base         2^3
                      mod_base = OTHER
                      note = phosphorothioate linkage
modified_base         3
                      mod_base = gm
modified_base         4
                      mod_base = OTHER
                      note = 2'-O-methyladenosine
modified_base         5
                      mod_base = um
modified_base         6
                      mod_base = um
modified_base         7
                      mod_base = OTHER
                      note = 2'-fluoroadenosine
modified_base         8
                      mod_base = gm
```

```
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 131
ttgattagca ggtcaaaagt g                                            21

SEQ ID NO: 132         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
```

```
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 132
ttgattagca ggtcaaaagt g                                           21

SEQ ID NO: 133         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
```

-continued

```
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 133
ttgattagca ggtcaaaagt g                                              21

SEQ ID NO: 134         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
```

```
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 134
ttgattagca ggtcaaaagt g                                            21

SEQ ID NO: 135         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
```

```
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 135
ttgattagca ggtcaaaagt g                                            21

SEQ ID NO: 136         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
```

-continued

```
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 136
ttgattagca ggtcaaaagt g                                                21

SEQ ID NO: 137         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
```

```
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 137
ttgattagca ggtcaaaagt g                                            21

SEQ ID NO: 138         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
```

-continued

```
modified_base          21
                       mod_base = gm
source                 1..21
                       mol_type = other RNA
                       organism = synthetic construct
SEQUENCE: 138
ttgattagca ggtcaaaagt g                                              21

SEQ ID NO: 139         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
```

```
SEQUENCE: 139
ttgattagca ggtcaaaagt g                                           21

SEQ ID NO: 140          moltype = RNA  length = 21
FEATURE                 Location/Qualifiers
modified_base           1
                        mod_base = OTHER
                        note = 5'-cyclopropyl phosphonate-2'-O-methyluridine
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = OTHER
                        note = 2'-fluoroadenosine
modified_base           8
                        mod_base = gm
modified_base           9
                        mod_base = cm
modified_base           10
                        mod_base = OTHER
                        note = 2'-O-methyladenosine
modified_base           11
                        mod_base = gm
modified_base           12
                        mod_base = OTHER
                        note = 2'-fluoroguanosine
modified_base           13
                        mod_base = um
modified_base           14
                        mod_base = OTHER
                        note = 2'-fluorocytidine
modified_base           15
                        mod_base = OTHER
                        note = 2'-O-methyladenosine
modified_base           16
                        mod_base = OTHER
                        note = 2'-fluoroadenosine
modified_base           17
                        mod_base = OTHER
                        note = 2'-O-methyladenosine
modified_base           18
                        mod_base = OTHER
                        note = 2'-O-methyladenosine
modified_base           19
                        mod_base = gm
modified_base           19^20
                        mod_base = OTHER
                        note = phosphorothioate linkage
modified_base           20
                        mod_base = um
modified_base           20^21
                        mod_base = OTHER
                        note = phosphorothioate linkage
modified_base           21
                        mod_base = gm
source                  1..21
                        mol_type = other RNA
                        organism = synthetic construct
SEQUENCE: 140
ttgattagca ggtcaaaagt g                                           21

SEQ ID NO: 141          moltype = RNA  length = 21
FEATURE                 Location/Qualifiers
```

```
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 141
ttgattagca ggtcaaaagt g                                                 21

SEQ ID NO: 142         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
```

-continued

```
modified_base         2
                      mod_base = OTHER
                      note = 2'-fluorouridine
modified_base         2^3
                      mod_base = OTHER
                      note = phosphorothioate linkage
modified_base         3
                      mod_base = gm
modified_base         4
                      mod_base = OTHER
                      note = 2'-O-methyladenosine
modified_base         5
                      mod_base = um
modified_base         6
                      mod_base = um
modified_base         7
                      mod_base = OTHER
                      note = 2'-fluoroadenosine
modified_base         8
                      mod_base = gm
modified_base         9
                      mod_base = cm
modified_base         10
                      mod_base = OTHER
                      note = 2'-O-methyladenosine
modified_base         11
                      mod_base = gm
modified_base         12
                      mod_base = OTHER
                      note = 2'-fluoroguanosine
modified_base         13
                      mod_base = um
modified_base         14
                      mod_base = OTHER
                      note = 2'-fluorocytidine
modified_base         15
                      mod_base = OTHER
                      note = 2'-O-methyladenosine
modified_base         16
                      mod_base = OTHER
                      note = 2'-fluoroadenosine
modified_base         17
                      mod_base = OTHER
                      note = 2'-O-methyladenosine
modified_base         18
                      mod_base = OTHER
                      note = 2'-O-methyladenosine
modified_base         19
                      mod_base = gm
modified_base         19^20
                      mod_base = OTHER
                      note = phosphorothioate linkage
modified_base         20
                      mod_base = um
modified_base         20^21
                      mod_base = OTHER
                      note = phosphorothioate linkage
modified_base         21
                      mod_base = gm
source                1..21
                      mol_type = other RNA
                      organism = synthetic construct
SEQUENCE: 142
ttgattagca ggtcaaaagt g                                            21

SEQ ID NO: 143        moltype = RNA  length = 21
FEATURE               Location/Qualifiers
modified_base         1
                      mod_base = OTHER
                      note = 5'-cyclopropyl phosphonate-2'-O-methyluridine
modified_base         1^2
                      mod_base = OTHER
                      note = phosphorothioate linkage
modified_base         2
                      mod_base = OTHER
                      note = 2'-fluorouridine
modified_base         2^3
                      mod_base = OTHER
                      note = phosphorothioate linkage
```

```
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 143
ttgattagca ggtcaaaagt g                                            21

SEQ ID NO: 144         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
```

```
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
modified_base          19
                       mod_base = gm
modified_base          19^20
                       mod_base = OTHER
                       note = phosphorothioate linkage
modified_base          20
                       mod_base = um
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 144
ttgattagca ggtcaaaagt g                                           21

SEQ ID NO: 145         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluoroadenosine
modified_base          2^3
                       mod_base = OTHER
                       note = phosphorothioate linkage
modified_base          3
                       mod_base = gm
modified_base          4
                       mod_base = um
modified_base          5
                       mod_base = cm
modified_base          6
                       mod_base = um
modified_base          7
                       mod_base = OTHER
                       note = 2'-fluoroadenosine
```

```
modified_base          8
                       mod_base = cm
modified_base          9
                       mod_base = cm
modified_base          10
                       mod_base = OTHER
                       note = 2'-O-methyladenosine
modified_base          11
                       mod_base = um
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = gm
modified_base          16
                       mod_base = OTHER
                       note = 2'-fluoroadenosine
modified_base          17
                       mod_base = um
modified_base          18
                       mod_base = gm
modified_base          19
                       mod_base = cm
modified_base          20
                       mod_base = um
modified_base          20^21
                       mod_base = OTHER
                       note = phosphorothioate linkage
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 145
tagtctacca tgtcgatgct g                                            21

SEQ ID NO: 146         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluoroadenosine
modified_base          2^3
                       mod_base = OTHER
                       note = phosphorothioate linkage
modified_base          3
                       mod_base = cm
modified_base          4
                       mod_base = OTHER
                       note = 2'-O-methyladenosine
modified_base          5
                       mod_base = OTHER
                       note = 2'-fluoroadenosine
modified_base          6
                       mod_base = cm
modified_base          7
                       mod_base = gm
modified_base          8
                       mod_base = OTHER
                       note = 2'-O-methyladenosine
modified_base          9
                       mod_base = gm
modified_base          10
                       mod_base = OTHER
                       note = 2'-O-methyladenosine
```

```
modified_base          11
                       mod_base = cm
modified_base          12
                       mod_base = OTHER
                       note = 2'-fluorouridine
modified_base          13
                       mod_base = gm
modified_base          14
                       mod_base = OTHER
                       note = 2'-fluoroadenosine
modified_base          15
                       mod_base = OTHER
                       note = 2'-O-methyladenosine
modified_base          16
                       mod_base = OTHER
                       note = 2'-fluorouridine
modified_base          17
                       mod_base = um
modified_base          18
                       mod_base = gm
modified_base          19
                       mod_base = cm
modified_base          20
                       mod_base = cm
modified_base          20^21
                       mod_base = OTHER
                       note = phosphorothioate linkage
modified_base          20^21
                       mod_base = OTHER
                       note = phosphorothioate linkage
modified_base          21
                       mod_base = um
source                 1..21
                       mol_type = other RNA
                       organism = synthetic construct
SEQUENCE: 146
tacaacgaga ctgaattgcc t                                            21

SEQ ID NO: 147         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluoroadenosine
modified_base          2^3
                       mod_base = OTHER
                       note = phosphorothioate linkage
modified_base          3
                       mod_base = cm
modified_base          4
                       mod_base = OTHER
                       note = 2'-O-methyladenosine
modified_base          5
                       mod_base = OTHER
                       note = 2'-fluoroadenosine
modified_base          6
                       mod_base = cm
modified_base          7
                       mod_base = gm
modified_base          8
                       mod_base = OTHER
                       note = 2'-O-methyladenosine
modified_base          9
                       mod_base = gm
modified_base          10
                       mod_base = OTHER
                       note = 2'-O-methyladenosine
modified_base          11
                       mod_base = cm
modified_base          12
                       mod_base = OTHER
                       note = 2'-fluorouridine
modified_base          13
                       mod_base = gm
```

```
modified_base          14
                       mod_base = OTHER
                       note = 2'-fluoroadenosine
modified_base          15
                       mod_base = OTHER
                       note = 2'-O-methyladenosine
modified_base          16
                       mod_base = OTHER
                       note = 2'-fluorouridine
modified_base          17
                       mod_base = um
modified_base          18
                       mod_base = gm
modified_base          19
                       mod_base = cm
modified_base          20
                       mod_base = cm
modified_base          20^21
                       mod_base = OTHER
                       note = phosphorothioate linkage
modified_base          20^21
                       mod_base = OTHER
                       note = phosphorothioate linkage
modified_base          21
                       mod_base = um
source                 1..21
                       mol_type = other RNA
                       organism = synthetic construct
SEQUENCE: 147
tacaacgaga ctgaattgcc t                                            21

SEQ ID NO: 148         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluoroadenosine
modified_base          2^3
                       mod_base = OTHER
                       note = phosphorothioate linkage
modified_base          3
                       mod_base = cm
modified_base          4
                       mod_base = um
modified_base          5
                       mod_base = OTHER
                       note = 2'-O-methyladenosine
modified_base          6
                       mod_base = OTHER
                       note = 2'-O-methyladenosine
modified_base          7
                       mod_base = OTHER
                       note = 2'-fluoroguanosine
modified_base          8
                       mod_base = um
modified_base          9
                       mod_base = gm
modified_base          10
                       mod_base = OTHER
                       note = 2'-O-methyladenosine
modified_base          11
                       mod_base = gm
modified_base          12
                       mod_base = OTHER
                       note = 2'-fluorouridine
modified_base          13
                       mod_base = cm
modified_base          14
                       mod_base = OTHER
                       note = 2'-fluorouridine
modified_base          15
                       mod_base = um
```

-continued

```
modified_base          16
                       mod_base = OTHER
                       note = 2'-fluoroguanosine
modified_base          17
                       mod_base = cm
modified_base          18
                       mod_base = OTHER
                       note = 2'-O-methyladenosine
modified_base          19
                       mod_base = um
modified_base          20
                       mod_base = gm
modified_base          20^21
                       mod_base = OTHER
                       note = phosphorothioate linkage
modified_base          20^21
                       mod_base = OTHER
                       note = phosphorothioate linkage
modified_base          21
                       mod_base = gm
source                 1..21
                       mol_type = other RNA
                       organism = synthetic construct
SEQUENCE: 148
tactaagtga gtcttgcatg g                                            21

SEQ ID NO: 149         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluoroadenosine
modified_base          2^3
                       mod_base = OTHER
                       note = phosphorothioate linkage
modified_base          3
                       mod_base = cm
modified_base          3^4
                       mod_base = OTHER
                       note = phosphorothioate linkage
modified_base          4
                       mod_base = OTHER
                       note = 2'-fluoroadenosine
modified_base          5
                       mod_base = OTHER
                       note = 2'-O-methyladenosine
modified_base          6
                       mod_base = OTHER
                       note = 2'-fluorocytidine
modified_base          7
                       mod_base = gm
modified_base          8
                       mod_base = OTHER
                       note = 2'-O-methyladenosine
modified_base          9
                       mod_base = gm
modified_base          10
                       mod_base = OTHER
                       note = 2'-O-methyladenosine
modified_base          11
                       mod_base = cm
modified_base          12
                       mod_base = OTHER
                       note = 2'-fluorouridine
modified_base          13
                       mod_base = gm
modified_base          14
                       mod_base = OTHER
                       note = 2'-fluoroadenosine
modified_base          15
                       mod_base = OTHER
                       note = 2'-O-methyladenosine
```

```
modified_base          16
                       mod_base = OTHER
                       note = 2'-fluorouridine
modified_base          17
                       mod_base = um
modified_base          18
                       mod_base = OTHER
                       note = 2'-fluoroguanosine
modified_base          19
                       mod_base = cm
modified_base          20
                       mod_base = cm
modified_base          20^21
                       mod_base = OTHER
                       note = phosphorothioate linkage
modified_base          21
                       mod_base = um
source                 1..21
                       mol_type = other RNA
                       organism = synthetic construct
SEQUENCE: 149
tacaacgaga ctgaattgcc t                                              21

SEQ ID NO: 150         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = OTHER
                       note = 2'-fluoroadenosine
modified_base          8
                       mod_base = gm
modified_base          9
                       mod_base = cm
modified_base          10
                       mod_base = OTHER
                       note = 2'-O-methyladenosine
modified_base          11
                       mod_base = gm
modified_base          12
                       mod_base = OTHER
                       note = 2'-fluoroguanosine
modified_base          13
                       mod_base = um
modified_base          14
                       mod_base = OTHER
                       note = 2'-fluorocytidine
modified_base          15
                       mod_base = OTHER
                       note = 2'-O-methyladenosine
modified_base          16
                       mod_base = OTHER
                       note = 2'-fluoroadenosine
modified_base          17
                       mod_base = OTHER
                       note = 2'-O-methyladenosine
modified_base          18
                       mod_base = OTHER
                       note = 2'-O-methyladenosine
```

-continued

```
modified_base         19
                      mod_base = gm
modified_base         19^20
                      mod_base = OTHER
                      note = phosphorothioate linkage
modified_base         20
                      mod_base = um
modified_base         20^21
                      mod_base = OTHER
                      note = phosphorothioate linkage
modified_base         21
                      mod_base = gm
source                1..21
                      mol_type = other RNA
                      organism = synthetic construct
SEQUENCE: 150
ttgattagca ggtcaaaagt g                                            21

SEQ ID NO: 151        moltype = RNA  length = 21
FEATURE               Location/Qualifiers
modified_base         1
                      mod_base = cm
modified_base         2
                      mod_base = OTHER
                      note = 2'-O-methyladenosine
modified_base         3
                      mod_base = cm
modified_base         4
                      mod_base = um
modified_base         5
                      mod_base = um
modified_base         6
                      mod_base = um
modified_base         7
                      mod_base = um
modified_base         8
                      mod_base = gm
modified_base         9
                      mod_base = OTHER
                      note = 2'-fluoroadenosine
modified_base         10
                      mod_base = OTHER
                      note = 2'-fluorocytidine
modified_base         11
                      mod_base = OTHER
                      note = 2'-fluorocytidine
modified_base         12
                      mod_base = um
modified_base         13
                      mod_base = gm
modified_base         14
                      mod_base = cm
modified_base         15
                      mod_base = um
modified_base         16
                      mod_base = OTHER
                      note = 2'-O-methyladenosine
modified_base         17
                      mod_base = OTHER
                      note = 2'-O-methyladenosine
modified_base         18
                      mod_base = um
modified_base         19
                      mod_base = cm
modified_base         20
                      mod_base = OTHER
                      note = 2'-O-methyladenosine
modified_base         21
                      mod_base = OTHER
                      note = 2'-O-methyladenosine
source                1..21
                      mol_type = other RNA
                      organism = synthetic construct
SEQUENCE: 151
cacttttgac ctgctaatca a                                            21

SEQ ID NO: 152        moltype = RNA  length = 21
FEATURE               Location/Qualifiers
```

```
modified_base          1
                       mod_base = cm
modified_base          2
                       mod_base = OTHER
                       note = 2'-O-methyladenosine
modified_base          3
                       mod_base = cm
modified_base          4
                       mod_base = um
modified_base          5
                       mod_base = um
modified_base          6
                       mod_base = um
modified_base          7
                       mod_base = um
modified_base          8
                       mod_base = gm
modified_base          9
                       mod_base = OTHER
                       note = 2'-fluoroadenosine
modified_base          10
                       mod_base = OTHER
                       note = 2'-fluorocytidine
modified_base          11
                       mod_base = OTHER
                       note = 2'-fluorocytidine
modified_base          12
                       mod_base = um
modified_base          13
                       mod_base = gm
modified_base          14
                       mod_base = cm
modified_base          15
                       mod_base = um
modified_base          16
                       mod_base = OTHER
                       note = 2'-O-methyladenosine
modified_base          17
                       mod_base = OTHER
                       note = 2'-O-methyladenosine
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 152
cacttttgac ctgctaatca a                                            21

SEQ ID NO: 153         moltype = RNA  length = 21
FEATURE                Location/Qualifiers
modified_base          1
                       mod_base = OTHER
                       note = 5'-cyclopropyl phosphonate-2'-O-methyluridine
modified_base          1^2
                       mod_base = OTHER
                       note = phosphorothioate linkage
modified_base          2
                       mod_base = OTHER
                       note = 2'-fluorouridine
modified_base          2^3
                       mod_base = OTHER
                       note = phosphorothioate linkage
modified_base          3
                       mod_base = gm
modified_base          4
                       mod_base = OTHER
                       note = 2'-O-methyladenosine
modified_base          5
                       mod_base = um
modified_base          6
                       mod_base = um
```

-continued

```
modified_base        7
                     mod_base = OTHER
                     note = 2'-fluoroadenosine
modified_base        8
                     mod_base = gm
modified_base        9
                     mod_base = cm
modified_base        10
                     mod_base = OTHER
                     note = 2'-O-methyladenosine
modified_base        11
                     mod_base = gm
modified_base        12
                     mod_base = OTHER
                     note = 2'-fluoroguanosine
modified_base        13
                     mod_base = um
modified_base        14
                     mod_base = OTHER
                     note = 2'-fluorocytidine
modified_base        15
                     mod_base = OTHER
                     note = 2'-O-methyladenosine
modified_base        16
                     mod_base = OTHER
                     note = 2'-fluoroadenosine
modified_base        17
                     mod_base = OTHER
                     note = 2'-O-methyladenosine
modified_base        18
                     mod_base = OTHER
                     note = 2'-O-methyladenosine
modified_base        19
                     mod_base = gm
modified_base        19^20
                     mod_base = OTHER
                     note = phosphorothioate linkage
modified_base        20
                     mod_base = um
modified_base        20^21
                     mod_base = OTHER
                     note = phosphorothioate linkage
modified_base        21
                     mod_base = gm
source               1..21
                     mol_type = other RNA
                     organism = synthetic construct
SEQUENCE: 153
ttgattagca ggtcaaaagt g                                        21
```